United States Patent
Sohn et al.

(10) Patent No.: US 8,176,786 B2
(45) Date of Patent: May 15, 2012

(54) METHODS, APPARATUSES, AND SYSTEMS FOR DAMAGE DETECTION

(75) Inventors: Hoon Sohn, Pittsburgh, PA (US); Seungbum Kim, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 544 days.

(21) Appl. No.: 12/308,824

(22) PCT Filed: Jun. 29, 2007

(86) PCT No.: PCT/US2007/015090
§ 371 (c)(1),
(2), (4) Date: Mar. 26, 2009

(87) PCT Pub. No.: WO2008/005311
PCT Pub. Date: Jan. 10, 2008

(65) Prior Publication Data
US 2009/0301198 A1 Dec. 10, 2009

Related U.S. Application Data

(60) Provisional application No. 60/818,121, filed on Jun. 30, 2006, provisional application No. 60/858,111, filed on Nov. 10, 2006, provisional application No. 60/858,572, filed on Nov. 13, 2006, provisional application No. 60/931,391, filed on May 23, 2007.

(51) Int. Cl.
*G01N 29/04* (2006.01)

(52) U.S. Cl. ............... 73/602; 73/598; 73/600

(58) Field of Classification Search ............ 73/596, 73/597, 598, 599, 600, 602, 579, 620, 622, 73/627–628
See application file for complete search history.

(56) References Cited

U.S. PATENT DOCUMENTS

| | | | | |
|---|---|---|---|---|
| 2,889,705 | A | | 6/1959 | Hanysz et al. |
| 3,575,050 | A | * | 4/1971 | Lynnworth ............... 73/861.27 |
| 4,679,430 | A | * | 7/1987 | Scott-Kestin et al. ...... 73/290 V |
| 6,092,420 | A | | 7/2000 | Kimura et al. |
| 6,125,705 | A | * | 10/2000 | Johnson ........................ 73/622 |
| 6,276,209 | B1 | * | 8/2001 | Schafer et al. .................. 73/597 |
| 7,363,817 | B2 | * | 4/2008 | Bond et al. ..................... 73/598 |
| 7,513,160 | B2 | * | 4/2009 | Lynch et al. ................... 73/602 |
| 2002/0134161 | A1 | * | 9/2002 | Chinn ............................ 73/622 |
| 2005/0146433 | A1 | | 7/2005 | Waltermann |
| 2007/0068257 | A1 | * | 3/2007 | Belahcene et al. .............. 73/597 |

OTHER PUBLICATIONS

Ing, Ros K. and Fink, Mathias, Time recompression of dispersive lamb waves using a time reversal mirror—Application to flaw detection in thin plates, IEEE Ultrasonic Symposium, 1996, pp. 659-663.

(Continued)

*Primary Examiner* — Helen C. Kwok
(74) *Attorney, Agent, or Firm* — Fox Rothschild LLP; Dennis M. Carleton

(57) ABSTRACT

Methods, apparatuses, and systems for damage detection and for other detection of the state of a structure or material. Such damage detection and detection of the state of a structure may be performed and operated without the use of baseline data. The present invention may operate using time reversal acoustics or polarization characteristics of piezoelectric devices. The present invention may include a piezoelectric device including two or more piezoelectric transducers.

32 Claims, 70 Drawing Sheets

OTHER PUBLICATIONS

"PCT Notification of Transmittal of the International Search Report and the Written Opinion of the International Searching Authority, or the Declaration" for Intl. App. No. PCT/US2007/015090, Form PCT/ISA/220, mailed May 21, 2008.

"PCT International Search Report" for Intl. App. No. PCT/US2007/015090, Form PCT/ISA/210, mailed May 21, 2008.

"PCT Written Opinion of the International Searching Authority" for Intl. App. No. PCT/US2007/015090, Form PCT/ISA/237, mailed May 21, 2008.

"PCT Notification of Transmittal of the International Preliminary Report on Patentability" for Intl. App. No. PCT/US2007/015090, Form PCT/IPEA/416, mailed Sep. 15, 2008.

"PCT International Preliminary Report on Patentability" for Intl. App. No. PCT/US2007/015090, Form PCT/IPEA/409, mailed Sep. 15, 2008.

Babcock, R.A. et al., The use of 0-3 piezocomposite embedded Lamb wave sensors for detection of damage in advanced fibre composites, Smart Matter, Struct. 9: 291-297, 2000.

Beardsley, B. et al., A simple scheme for self-focusing of an array, Journal of Nondestructive Evaluation. 14(4): 169-179, 1995, abstract.

Cho, Younho, Estimation of ultrasonic guided wave mode conversion in a plate with thickness variation, IEEE Transactions on Ultrasonics, Ferroelectrics, and Frequency Control, 47(3): 591-603, 2000.

Draeger, C. et al., Theory of the time-reversal process in solids, J. Acoust. Soc. Am. 102(3): 1289-1295, 1997.

Discalea, F. et al., Propagation of ultrasonic guided waves in lap-shear adhesive joints: case of incident a0 Lamb wave, J. Acoust. Soc. Am. 115(1): 146-156, 2004.

Edelmann, G.F. et al., Underwater acoustic communications using time reversal, IEEE Journal of Oceanic Engineering, 30(4): 852-864, 2005.

Fink, M. et al., Time-reversal acoustics in biomedical engineering, Annu. Rev. Biomed. Eng. 5: 465-497, 2003.

Giurgiutiu, Victor, Embedded NDE with piezoelectric wafer-active sensors in aerospace applications, Journal of Materials, 2003.

Ing, R.K. et al., Time recompression of dispersive lamb waves using a time reversal mirror—application to flaw detection in thin plates, IEEE Ultrasonics Symposium, 659-663, 1996.

Ing, R.K. et al., Time-reversed lamb waves, IEEE Transactions on Ultrasonics, Ferroelectrics, and Frequency Control, 45(4): 1032-1043, 1998.

Ing, R.K. et al., Self-focusing and time recompression of Lamb waves using a time reversal mirror, Ultrasonics 36: 179-186, 1998.

Prada, C. et al., Separation of interfering acoustic scattered signals using the invariants of the time=reversal operator, application to Lamb waves characterization, J. Acoust. Soc. Am., 104(2): 801-807, 1998.

Lamb, Horace, On waves in an elastic plate, Proc. R. Soc. Lond. A, 93: 114-128, 1917, TOC.

Paget, C.A. et al., Damage assessment in composites by Lamb waves and wavelet coefficients, Smart Mater, Struct. 12: 393-402, 2003.

Park, Chul H., On the circuit model of piezoceramics, Journal of Intelligent Material Systems and Structures, 12: 515-522, 2001.

Park, H.W. et al., Time reversal active sensing for health monitoring of a composite plate, Journal of Sound and Vibration, 302: 50-66, 2007.

Park, H.W. et al., Understanding a time reversal process in Lamb wave propagation, Wave Motion 46: 451-467 (2009).

Rose, L.R.F. et al., Mindlin plate theory for damage detection: source solutions, J. Acoust. Soc. Am., 116(1): 154-171, 2004.

Sohn, H. et al., Damage detection in composite plates by using an enhanced time reversal method, Journal of Aerospace Engineering, 141-151, Jul. 2007.

Sohn, H. et al., Combination of a time reversal process and a consecutive outlier analysis for baseline-free damage diagnosis, Journal of Intelligent Material Systems and Structures, 18: 335-346, 2007.

Sohn, H. et al., Wavelet-based active sensing for delamination detection in composite structures, Smart Mater, Struct. 13: 153-160, 2004.

Su, Z. et al., Selective generation of Lamb wave modes and their propagation characteristics in defective composite laminates, Proc. Instn Mech. Engrs 218, Part L, 95-110, 2004.

Tan, K.S. et al., Comparison of Lamb waves and pulse echo in detection of near-surface defects in laminate plates. NDT&E International 28(4): 215-223, 1995.

Tan, K.S. et al., Experimental evaluation of delaminations in composite plates by the use of Lamb waves, Composites Science and Technology 53: 77-84, 1995.

Teknomo, Kardi, K-Mean clustering tutorials, http://people.revoledu.com/kardi/tutorial/kMean/index.html (copyright notice dated 2006).

Zhongqing, S. et al., Guided Lamb waves for identification of damage in composite structures: a review, Journal of Sound and Vibration, 295: 753-780, 2006.

COMSOL Multiphysics 3.3a, http://www.comsol.com/press/news/article/141 (article dated Feb. 2, 2007).

\* cited by examiner

AB-BA

AB-BA

METHODS, APPARATUSES, AND SYSTEMS FOR DAMAGE DETECTION

CROSS-REFERENCE TO RELATED APPLICATIONS

This application claims priority from International application number PCT/US2007/015090, filed Jun. 29, 2007, which claims priority from U.S. Provisional Patent Application No. 60/818,121, filed Jun. 30, 2006, U.S. Provisional Patent Application No. 60/858,111, filed Nov. 10, 2006, U.S. Provisional Patent Application No. 60/858,572, filed Nov. 13, 2006, and U.S. Provisional Patent Application No. 60/931,391, filed May 23, 2007, all of which are incorporated herein by reference.

STATEMENT REGARDING FEDERALLY-SPONSORED RESEARCH AND DEVELOPMENT

Not Applicable.

FIELD OF THE INVENTION

The present invention is directed generally to methods, apparatuses, and systems for damage detection, more specifically, to such methods, apparatuses, and systems which utilize autonomous baseline-free diagnosis.

BACKGROUND OF THE INVENTION

There are several ways in which damage detection is performed in the prior art. According to conventional time reversal acoustics, an input signal can be reconstructed at an excitation point if an output signal recorded at another point is reversed in the time domain and emitted back to the original source point (Fink M. Time-reversed acoustics. Scientific American 1999; 281(5):91-97). This time reversibility is based on the spatial reciprocity and time-reversal invariance of linear wave equations (Draeger C, Cassereau D, Fink M. Theory of the time-reversal process in solids. Journal of the Acoustical Society of America 1997; 102(3):1289-1295. DOI: 10.1121/1.420094).

Time reversal acoustics was first introduced by modern acoustics community and applied to many fields such as lithotripsy, and ultrasonic brain surgery, active sonar and underwater communications, medical imaging, hyperthermia therapy, bioengineering, and non-destructive testing (NDT) (Edelmann G, Song H C, Kim S, Hodgkiss W S, Kuperman W A, Akal T. Underwater acoustic communication using time reversal, IEEE J. Oceanic Eng. 30, 852-864, 2005; Fink M, Montaldo G, Tanter M, Time-reversal acoustics in biomedical engineering, Annual Review of Biomedical Engineering 5: 465-497 2003; Fink M. Time-reversed acoustics. Scientific American 1999; 281(5):91-97; Beardsley B, Peterson M, Achenbach J D, A Simple Scheme for Self-Focusing of an Array, Nondestructive Evaluation 14(4) 169-179, 1995). Then, Ing and Fink adopted the time reversal process (TRP) to Lamb waves based NDT in order to compensate the dispersion of Lamb waves and to detect defects in a pulse-echo mode (Ing R K, Fink M. Time recompression of dispersive Lamb waves using a time reversal mirror—Application to flaw detection in thin plates. IEEE Ultrasonics Symposium 1996; 1:659-663. DOI: 10.1109/ULTSYM.1996.584061; Prada C, Fink M. Separation of interfering acoustic scattered signals using the invariants of the time-reversal operator. Application to Lamb waves characterization. Journal of the Acoustical Society of America 1998; 104(2):801-807. DOI: 10.1121/1.423354; Ing R K, Fink M. Self-focusing and time recompression of Lamb waves using a time reversal mirror. Journal of the Acoustical Society of America, 104(2), 801-807, 1998(a); Ing R K, Fink M. Time-Reversed Lamb Waves. IEEE transactions on ultrasonics, ferroelectrics, and frequency control 1998(b); 45(4):1032-1043. DOI: 10.1109/58.710586). The main interest of these studies was refocusing energy in the time and spatial domain by compensating the dispersive characteristics of Lamb waves.

The application of a time reversal process to Lamb wave propagations is complicated due to many factors, such as velocity and amplitude dispersion characteristics of Lamb waves and reflections from the boundaries of a structure. As a result, prior art techniques require either a human to review the results and exercise considerable judgment in order to determine the results of the test, or they require comparison to baseline data to determine if a significant change has occurred in the object being tested.

In the case of prior art solutions requiring trained human operators, the prior art solution is expensive and slow, and it has limited applicability, particularly if frequent reports are desired. For example, if NDT is to be used in applications such as testing the integrity of airplane components between every flight, then this prior art system is not practical. This solution also can lead to inconsistent results because the decision making process includes a large subjective component, and the same data can be interpreted differently by different human operators.

In the case of prior art solutions requiring the use of baseline data, there is a significant chance for false positive results as a result of factors such as changing environmental conditions. As a results, those solutions also offer significant drawbacks.

The prior art also teaches the use of guided waves. The use of guided waves has been used in Structural Health Monitoring (SHM) and Nondestructive Testing (NDT) techniques for continuous monitoring of aging aircraft, civil infrastructure and mechanical systems that have driven maintenance costs to unprecedented levels. For SHM NDT, guided waves have received a great deal of attention and have been a topic of considerable interest, because they can propagate over considerable distances with little attenuation. Conventional guided wave studies have focused on schemes where baseline signals are measured so that changes from the baseline can be detected. However, there are significant technical challenges to realizing this pattern comparison. For instance, structural defects typically take place long after the initial baseline data are collected, and other operational and environmental variations of the system can produce significant changes in the measured response, masking any potential signal changes due to structural defects.

Additionally, as discussed above, some prior art solutions require the use of a trained human operator to review the results and exercise judgment in order to determine the results of the test. As a result, these prior art solutions are expensive and slow, and they have limited applicability, particularly if frequent reports are desired. This solution also can lead to inconsistent results because the decision making process includes a large subjective component, and the same data can be interpreted differently by different human operators.

Accordingly, there is a need for improved methods, apparatuses, and systems for diagnosis testing which is both autonomous and baseline-free. In particular, there is a need for methods, apparatuses, and systems which utilize a time reversal process for diagnosis testing which is both autonomous and baseline-free. In addition, there is a need for methods, apparatuses, and systems that are less vulnerable to operational and environmental variations that might occur throughout the life span of the structures being monitored. Those and other advantages of the present invention will be described in more detail hereinbelow.

BRIEF SUMMARY OF THE INVENTION

The present invention has many variations and embodiments. In some embodiments, the present invention is directed to a time reversal process (TRP). In other embodiments, the present invention utilizes polarization characteristics of piezoelectric materials. Other variations and embodiments of the present invention are also disclosed.

The present invention is directed to the applicability of the time reversal concept in modern acoustics to Lamb waves Theoretical investigations are presented to better understand the time reversibility of Lamb waves. First, reciprocity of elastic waves for Lamb wave propagations is introduced based on elastodynamics, and the concept of the TRP is extended for Lamb wave propagations. In particular, the effect of velocity and amplitude dispersion, the existence of multimodes, reflections from boundaries, the use of peizoceramic wafer transducers for the TRP are theoretically investigated. In addition, numerical simulations and experimental tests are conducted to validate the theoretical findings of the present invention and to further investigate the effects of defects and variations in wafer transducer size and bonding on the TRP.

The present invention advances this TRP concept to develop a NDT technique where defects can be identified without requiring direct comparison with previously obtained baseline data (Park H W, Sohn H, Law K H, Farrar C R. Time Reversal Active Sensing for Health Monitoring of a Composite Plate. Journal of Sound and Vibration 2006 (in press); Sohn H, Park H W, Law K H, Farrar C R. Damage detection in composite plates by using an enhanced time reversal method. Journal of Aerospace Engineering, ASCE 2006a (in press); Sohn H, Park H W, Law K H, Farrar C R. Combination of a time reversal process and a consecutive outlier analysis for baseline-free damage diagnosis. Journal of Intelligent Materials and Smart Structures 2006b (in press)). According to one embodiment of the present invention, the "shape" of the original input signal is reconstructed during the TRP. When nonlinearity is caused by a defect along a direct wave path, the shape of the reconstructed signal is reported to deviate from that of the original input signal. Therefore, examining the deviation of the reconstructed signal from the known initial input signal allows instantaneous identification of damage without requiring the baseline signal for comparison. However, the full reconstruction of the input signal is complicated due to dispersion and multimode characteristics of Lamb waves.

The time reversibility of Lamb waves is theoretically investigated, limitations in terms of full reconstruction of the input signal discussed, and techniques to enhance the Lamb time reversibility are developed. In particular, attention has been paid to understanding the effects of the following on the TRP: (1) velocity and amplitude dispersion characteristics of Lamb waves, (2) the existence of multiple Lamb wave modes, (3) reflections from structural boundaries, and (4) lead zirconate titanate (PZT) wafer transducers used for generating and measuring Lamb waves. In addition, numerical simulations and experimental tests are conducted to validate the theoretical findings of this study and to further examine the effects of defects and variations in PZT size and bonding condition on the TRP. Furthermore, reciprocity of elastic waves for Lamb wave propagation and the time reversibility of Lamb waves are shown experimentally. The effects of velocity and amplitude dispersion, the existence of multimodes, reflections from boundaries are also validated. Finally, the effects of defects and variations in piezoceramic wafer transducer size and bonding, and operational and environmental variations on the TRP are investigated.

The present invention also includes a new methodology of guided wave-based nondestructive testing (NDT) to detect damage, such as crack, corrosion, and delamination damage, in metallic and composite structures, without using prior baseline data or human operators. In conventional guided wave based techniques, damage is often identified by comparing the "current" data obtained from a potentially damaged condition of a structure with the "past" baseline data collected at the pristine condition of the structure. However, it has been reported that this type of pattern comparison with the baseline data can lead to increased false alarms due to its susceptibility to varying operational and environmental conditions of the structure. To develop a more robust damage diagnosis technique, a new concept of NDT is disclosed so that crack, corrosion, and delamination defects can be detected without direct comparison with the baseline data and without the use of human operators to review the data and determine the result of the test.

One embodiment of the present invention includes NDT techniques that utilize the polarization characteristics of the piezoelectric wafers attached on the both sides of the thin metal structure. During the operation of the present invention, certain types of defects in the structure create Lamb wave mode conversion due to a sudden change in the thickness of the structure. According to one embodiment, the present invention detects the presence of the defect by extracting the mode conversion from the measured Lamb waves even in the presence of changing operational and environmental conditions. Numerical and experimental results are presented to demonstrate the applicability of the proposed technique to crack detection. Similar approaches can be used to detect corrosion and delamination in metallic and composite structures.

In another embodiment, the present invention is a method for autonomous baseline-free diagnosis of a structure, comprising: generating a first acoustic signal from a first location on the structure, wherein the first acoustic signal has a main frequency and a bandwidth, and wherein the bandwidth is ten percent of the main frequency; receiving the first acoustic signal at a second location on the structure, wherein the first location and the second location are different; generating a second acoustic signal from the second location on the structure, wherein the second acoustic signal has a main frequency and a bandwidth, and wherein the bandwidth is ten percent of the main frequency; receiving the second acoustic signal at the first location on the structure; and identifying mode conversion in the first and second acoustic signals.

In another embodiment, the present invention is a system for autonomous baseline-free diagnosis of a structure, wherein the structure has a first surface and a second surface, wherein the first and second surfaces are on opposite sides of the structure, and comprising: a first piezoelectric device at a first location on the first surface of the structure; a second piezoelectric device at a second location on the first surface of the structure; a third piezoelectric device at the second location on the second surface of the structure; a fourth piezoelectric device at the first location on the second surface of the structure; a signal generator connected to at least two of the first, second, third, and fourth piezoelectric devices; a processor connected to the signal generator and connected to the first, second, third, and fourth piezoelectric devices; and computer readable memory connected to the processor. The memory includes computer-readable instructions which, when executed by the processor, cause: generating a first acoustic signal from the first location on the structure, wherein the first acoustic signal has a main frequency and a bandwidth, and wherein the bandwidth is ten percent of the main frequency; receiving the first acoustic signal at the second location on the structure, wherein the first location and the second location are different; generating a second acoustic signal from the second location on the structure, wherein the second acoustic signal has a main frequency and a bandwidth, and wherein the bandwidth is ten percent of the main frequency; receiving the second acoustic signal at the first location on the structure; and identifying mode conversion in the first and second acoustic signals.

In another embodiment, the present invention is a method for autonomous baseline-free diagnosis of a structure (30), comprising generating a first acoustic signal from a first location on the structure, wherein the first acoustic signal has a main frequency and a bandwidth, and wherein the bandwidth is ten percent of the main frequency; receiving the first acoustic signal at a second location on the structure, wherein the first location and the second location are different; reversing, in the time domain, the first acoustic signal received at the second location; truncating the first acoustic signal received at the second location; generating a second acoustic signal from the second location on the structure, wherein the second acoustic signal is the truncated, time domain reversed first acoustic signal received at the second location; receiving the second acoustic signal at the first location on the structure; and determining a diagnosis of the structure based on the second acoustic signal received at the first location.

In another embodiment, the present invention is a system for autonomous baseline-free diagnosis of a structure, comprising a first piezoelectric device at a first location on the structure, a second piezoelectric device at a second location on the structure, a signal generator connected to the first piezoelectric device, a processor connected to the signal generator and connected to the first and second piezoelectric devices, and computer readable memory connected to the processor. The memory includes computer-readable instructions which, when executed by the processor, cause generating a first acoustic signal from a first location on the structure, wherein the first acoustic signal has a main frequency and a bandwidth, and wherein the bandwidth is ten percent of the main frequency; receiving the first acoustic signal at a second location on the structure, wherein the first location and the second location are different; reversing, in the time domain, the first acoustic signal received at the second location; truncating the first acoustic signal received at the second location; generating a second acoustic signal from the second location on the structure, wherein the second acoustic signal is the truncated, time domain reversed first acoustic signal received at the second location; receiving the second acoustic signal at the first location on the structure; and determining a diagnosis of the structure (30) based on the second acoustic signal received at the first location.

In another embodiment, the present invention is a piezoelectric device comprising an excitation piezoelectric transducer for generating an acoustic signal and a sensing piezoelectric transducer (52) for receiving an acoustic signal.

In a thin elastic medium such as an aluminum plate, the formation of a crack causes the conversion of the propagation waves to other modes. The present invention includes a technique that can isolate this mode conversion using the poling directions of piezoelectric materials such as Lead Zirconate Titanate (PZT). The uniqueness of the proposed damage damage detection technique is that this mode conversion due to damage is instantly identified without using prior baseline data and without requiring a human operator to interpret the results. By removing the dependency on the prior baseline data and human operators, the proposed damage detection system becomes less vulnerable to operational and environmental variations that might occur throughout the life span of the structures being monitored.

The present invention can overcome the drawbacks of the prior art NDT methods because, for example, the present invention includes an NDT technique which does not rely on previously obtained baseline data and does not require a human operator to interpret the results. These and other teachings, variations, and advantages of the present invention will become apparent from the following detailed description of the invention.

Many variations are possible with the present invention, such as by combining and modifying the teachings and examples presented herein. These and other teachings, variations, and advantages of the present invention will become apparent from the following detailed description of the invention.

BRIEF DESCRIPTION OF THE SEVERAL VIEWS OF THE DRAWING

Embodiments of the present invention will now be described, by way of example only, with reference to the accompanying drawings for the purpose of illustrating the embodiments, and not for purposes of limiting the invention, wherein:

FIG. 10 illustrates a wavelet analysis procedure for wavelet based signal denoising, wherein FIG. 10(a) illustrates a response time signal, FIG. 10(b) illustrates a Morlet wavelet at 110 kHz, FIG. 10(c) illustrates Time-frequency response, and wherein FIG. 10(d) illustrates a time response at input frequency;

FIG. 11 illustrates a damage localization procedure using virtual grids according to one embodiment of the present invention wherein FIG. 11(a) illustrates actual damage simulated by placing industrial putties, FIG. 11(b) illustrates actuator-sensor paths affected by delamination, FIG. 11(c) illustrates identifying all boxes crossing the damage paths at least once, FIG. 11(d) illustrates excluding any boxes crossing the undamaged paths, FIG. 11(e) illustrates defining the first possible damage location, and FIG. 11(f) illustrates identifying damaged paths not crossing the selected box(es);

FIGS. 16 and 17 illustrate experimental verification of the reciprocity and time reversibility of Lamb wave propagation based on the test setup shown in FIG. 14, wherein FIG. 16 illustrates reciprocity paths A→B & B→A, and wherein FIG. 17 illustrates time reversibility for paths A→B→A & B→A→B;

FIGS. 18 and 19 illustrate a broadband Gaussian impulse signal wherein FIG. 18 illustrates a Gaussian impulse in the time domain and FIG. 19 illustrates a Gaussian impulse in the frequency domain;

FIGS. 20 and 21 illustrate a narrowband toneburst signal at 130 kHz, wherein FIG. 20 illustrates a toneburst signal in the time domain, and wherein FIG. 21 illustrates a toneburst signal in the frequency domain;

FIGS. 22 and 23 illustrate reconstructed signals after the TRP using broadband and narrowband input signals, wherein FIG. 22 illustrates the reconstructed signal using a narrowband input signal, and FIG. 23 illustrates the reconstructed signal using a broadband input signal;

FIGS. 24 and 25 illustrate experimental verification of the multimodal effects by truncating the forwarding signals at different time points for the TRP in which case I is truncated after the So mode and Case II is truncated after the So and Ao modes, in which FIG. 24 illustrates the forwarding signal A to B, and FIG. 25 illustrates the reconstructed signals;

FIGS. 28 and 29 illustrate the effect of PZT size on reciprocity and time reversibility in which PZT A is 1.0 cm×1.0 cm and PZT B is 0.7 cm×0.7 cm, and wherein FIG. 28 illustrates reciprocity for paths A→B & B→A, and wherein FIG. 29 illustrates time reversibility for paths A→B→A & B→A→B;

FIGS. 30 and 31 illustrate the effect of PZT size on reciprocity and time reversibility in which PZT A is 1.0 cm×1.0 cm and PZT B is 2.0 cm×2.0 cm, and wherein FIG. 30 illustrates reciprocity for paths A→B & B→A, and wherein FIG. 31 illustrates time reversibility for paths A→B→A & B→A→B;

FIGS. 33 and 34 illustrate the effect of PZT shape on reciprocity and time reversibility in Case I in which PZT A is 1.0 cm×1.0 cm and PZT B is 2.0 cm×0.5 cm, and wherein FIG. 33 illustrates reciprocity for paths A→B & B→A, and wherein FIG. 34 illustrates time reversibility for paths A→B→A & B→A→B;

FIGS. 35 and 36 illustrate the effect of PZT shape on reciprocity and time reversibility in Case 2 (PZT A: 1.0 cm×1.0 cm, PZT B: An equilateral triangle with 1.52 cm side), wherein FIG. 35 illustrates reciprocity for paths A→B & B→A→A, and wherein FIG. 36 illustrates time reversibility for paths A→B→A & B→A→B;

FIGS. 37 and 38 illustrate the effect of PZT Shape on reciprocity and time reversibility in Case 3 (PZT A, B: 1.0 cm×1.0 cm, PMT B is 45° rotated with respect to PZT A), wherein FIG. 37 illustrates reciprocity for paths A→B & B→A, and wherein FIG. 38 illustrates time reversibility for paths A→B→A & B→A→B;

FIGS. 39 and 40 illustrate the effect of PZT bonding material on reciprocity and time-reversibility (PZT A, B: 1.0 cm×1.0 cm, A: Cyanoacrylate, B: Conductive epoxy), wherein FIG. 39 illustrates reciprocity for paths A→B→B→A, and wherein FIG. 40 illustrates time reversibility for paths A→B→A & B→A→B;

FIGS. 41 and 42 illustrate the effect of PZT irregular bonding on reciprocity and time reversibility (PZT A, B: 1.0 cm×1.0 cm, 30% of PZT B is bonded on a folded vinyl layer), wherein FIG. 41 illustrates reciprocity for paths A→B & B→A, and wherein FIG. 42 illustrates time reversibility for paths A→B→A & B→A→B;

FIGS. 43 and 44 illustrate a comparison between medium and low temperature cases, wherein FIG. 43 illustrates a forwarding signal, and wherein FIG. 44 illustrates reconstructed signal after the TRP;

FIGS. 45 and 46 illustrate a comparison between medium and high temperature cases, wherein FIG. 45 illustrates a forwarding signal, and wherein FIG. 46 illustrates reconstructed signal after the TRP;

FIGS. 47 and 48 illustrate a comparison between no tapping and tapping cases, wherein FIG. 47 illustrates a forwarding signal, and wherein FIG. 48 illustrates a reconstructed signal after the TRP;

FIGS. 49 and 50 illustrate an aluminum bar specimen used for tests, wherein FIG. 49 illustrates the aluminum bar simply supported and wherein FIG. 50 illustrates the aluminum bar with one end fixed;

FIGS. 51 and 52 illustrate a comparison between no clamp and clamp cases, wherein FIG. 51 illustrates a forwarding signal and wherein FIG. 52 illustrates a reconstructed signal after the TRP;

FIGS. 54 and 55 illustrate a comparison between no silly putty and silly putty cases, wherein FIG. 54 illustrates a forwarding signal and wherein FIG. 55 illustrates a reconstructed signal after the TRP;

FIGS. 57 and 58 illustrates the effects of block attachment on the forward and the reconstructed signal (Exciting frequency: 90 kHz, 20 times averaging, LNP gain: 10), wherein FIG. 57 illustrates a forward signal measured at PZT B, and wherein FIG. 58 illustrates a reconstructed signal at PZT A;

FIGS. 60 and 61 illustrates mode conversion introduced by notch (Exciting frequency: 130 kHz, 20 times averaging, LNP gain: 10), wherein FIG. 60 illustrates a forward signal measured at PZT B, and wherein FIG. 61 illustrates a reconstructed signal at PZT A;

FIG. 62 illustrates the forwarding signal AB and FIG. 63 illustrates the reconstructed signals.

FIG. 64 illustrates the forwarding signal AB (the direct and reflected $A_0$ modes are saturated). FIG. 65 illustrates the reconstructed signal in Case I. FIG. 66 illustrates the reconstructed signal in Case II.

FIGS. 67-69 illustrate a poling process of an artificially polarized material, wherein FIG. 67 illustrates A crystalline material is heated up near its Curie temperature, FIG. 68 illustrates the applied electric field aligns the dipoles along the field lines, and FIG. 69 illustrates the polarization is permanently maintained after cooling;

FIGS. 70 and 71 illustrate the effect of the PZT poling directions on the phases of the S0 and A0 modes (Configuration I), wherein FIG. 70 illustrates test configuration I with collocated PZTs with the opposite poling directions, and wherein FIG. 71 illustrates the S0 mode produces the same bending for PZTs B and C while the A0 mode results in the opposite bending;

FIGS. 72 and 73 illustrate the effect of the PZT poling directions on the phases of the $S_0$ and $A_0$ modes (Configuration II), wherein FIG. 72 illustrates test configuration II with all PZTs with the same poling directions and wherein FIG. 73 illustrates the $S_0$ mode produces the opposite bending for PZTs B and C while the $A_0$ mode results in the same bending;

FIGS. 74 and 75 illustrate a schematic comparison of the $S_0$ and $A_0$ modes measured from Configurations I and II shown in FIG. 70 and FIG. 72, respectively: AB (a dash line) and AC (a solid line) denote the response signals measured at PZTs B and C when a tone burst input is applied at PZT A, wherein FIG. 74 illustrates $S_0$ and $A_0$ modes measured from configuration I in FIG. 70: $S_0$ modes in-phase & $A_0$ modes out-of-phase, and wherein FIG. 75 illustrates $S_0$ and $A_0$ modes measured from configuration II in FIG. 72: $S_0$ modes out-of-phase & $A_0$ modes in-phase;

FIGS. 77-80 illustrate extraction of the additional Lamb wave modes generated by a notch using the poling directionality of the PZT transducers ($A_0/S_0$ mode denotes an $A_0$ converted from $S_0$ when it passes through damage in the structure. $S_0/A_0$ is defined similarly), wherein FIG. 77 illustrates an intact plate with the PZT configuration II shown in FIG. 72, wherein FIG. 78 illustrates a comparison of signals AB and CD without a notch: the $S_0$ & $A_0$ modes are identical, wherein FIG. 79 illustrates a damaged plate with the PZT configuration II shown in FIG. 72, and wherein FIG. 80 illustrates a comparison of signals AB and CD with a notch: the S0 & A0 modes are identical, but the S0/A0 & A0/S0 modes are out-of-phase;

FIGS. 81-88 illustrate compensation of sensor misalignment using the proposed filtering process (AB*CD denote the point-by-point product (PPP) between signals AB and CD), wherein FIG. 81 illustrates signals AB and CD when PZT C is shifted 0.76 mm to the tight with respect to PZT B, wherein FIG. 82 illustrates a difference between signals AB and CD, wherein FIG. 83 illustrates the PPP values between signals AB and CD when PZT C is shifted 0.76 mm to the right with respect to. PZT B, wherein FIG. 84 illustrates a zoomed-in version of (c), indicating the durations of positive values and negative values due to misalignment, and wherein FIG. 85 illustrates a zoomed-in version of FIG. 83, highlighting the negative values of the PPP: a dash line before filtering, and a solid line after filtering;

FIG. 86 illustrates dimension of an aluminum plate used in numerical simulation according to the present invention;

FIGS. 87 and 88 illustrate simulated Lamb wave signals without notch, wherein FIG. 87 illustrates signals AB and CD without a notch, and wherein FIG. 88 illustrates difference between signals AB and CD;

FIGS. 89 and 90 illustrate simulated Lamb wave signals, with a notch of 3 mm depth and 1 mm width, wherein FIG. 89 illustrates signals AB and CD with a notch (3 mm depth, 1 mm width), and wherein FIG. 90 illustrates the difference between signals AB and CD with a notch (3 mm depth, 1 mm width);

FIGS. 91 and 92 illustrate the effect of PZT misalignment on the difference between signals AB and CD (PZT C shifted 1 mm to the right with respect to PZT B), wherein FIG. 91 illustrates signals AB and CD with PZT C shifted 1 mm to the right wrt PZT B, and wherein FIG. 92 illustrates the difference between signals AB and CD with PZT C shifted 1 mm to the right with respect to PZT B;

FIGS. 93 and 94 illustrate compensation of the PZT transducer misalignment using the proposed filtering technique (PZT C: shifted 1 mm to the right with respect to PZT B, without a notch), wherein FIG. 93 illustrates the PPP values between signals AB and CD when PZT C is shifted 1 mm to the right with respect to PZT B, and wherein FIG. 94 illustrates negative PPP values between signals AB and CD before and after applying the proposed filtering;

FIGS. 95 and 96 illustrate comparison of signals AB and CD with PZT transducer misalignment and a 3 mm depth notch, wherein FIG. 95 illustrates signals AB and CD with PZT C shifted 1 mm to the right and a 3 mm depth notch, and wherein FIG. 96 illustrates the difference between signals AB and CD with PZT C shifted 1 mm to the right and a 3 mm depth notch;

FIGS. 97 and 98 illustrate the extraction of the mode conversion using the proposed filtering technique at the presence of the PZT transducer misalignment (PZT C: shifted 1 mm to the right with respect to PZT B and a 3 mm depth notch), wherein FIG. 97 illustrates the PPP values between signals AB and CD with PZT C shifted 1 mm to the right and a 3 mm depth notch, and wherein FIG. 98 illustrates negative PPP values between signals AB and CD before and after applying the proposed filtering;

FIGS. 99 and 100 illustrate a testing configuration for detecting a crack on an aluminum plate, wherein FIG. 99 illustrates a data acquisition system, and wherein FIG. 100 illustrates a square aluminum plate;

FIGS. 101 and 102 illustrate comparison of signals AB and CD without notch, wherein FIG. 101 illustrates signals AB and CD without notch, and wherein FIG. 102 illustrates the difference between signals AB and CD;

FIGS. 103 and 104 illustrate comparison of signals AB and CD with a 3 mm depth notch, wherein FIG. 103 illustrates signals AB and CD with a 3 mm notch, and wherein FIG. 104 illustrates the difference between signals AB and CD; and FIGS. 105 and 106 illustrate the extraction of the mode conversion produced by a 3 mm depth notch using the proposed filtering technique at the presence of the PZT transducer misalignment, wherein FIG. 105 illustrates negative PPP values between signals AB and CD before and after applying the proposed filtering (without a notch), and wherein FIG. 106 illustrates negative PPP values between signals AB and CD before and after applying the proposed filtering (with a 3 mm depth notch).

FIGS. 108 and 109 illustrate a comparison between signals AB and BA without damage, wherein FIG. 108 illustrates an intact plate with two regular PZTs attached on a single surface, wherein FIG. 109 illustrates signals AB and BA and the difference between two signals: two signals are identical;

FIGS. 110 and 111 illustrate a comparison between signals AB and BA with a notch between PZT A and PZT B ($A_0/S_0$ mode denotes an $A_0$ converted from $S_0$ when it passes through damage in the structure. $S_0/A_0$ is defined similarly), wherein FIG. 10 illustrates a plate with a notch, wherein FIG. 11 illustrates signals AB and BA with a notch: even in the presence of a notch, two signals are identical; in-phase;

FIGS. 112 and 113 illustrate a schematic diagram of test sets to extract mode converted signals from measured Lamb wave signals, wherein FIG. 112 illustrates the main idea of the test sets: signal AB is obtained using a large PZT in set A as an actuator and a small PZT in set B as a sensor. Signal BA is also obtained in the same fashion, wherein FIG. 113 illustrates a comparison between signals AB and BA: only mode converted signals show deviation using test sets A and B;

FIGS. 116 and 117 illustrate simulated Lamb wave signals without notch, wherein FIG. 116 illustrates signals AB and BA without a notch, and wherein FIG. 117 illustrates difference between signals AB and BA;

FIGS. 118 and 119 illustrate simulated Lamb wave signals with a notch of 3 mm depth and 1 mm width, wherein FIG. 118 illustrates signals AB and BA with a notch. (3 mm depth, 1 mm width), and wherein FIG. 119 illustrates the difference between signals AB and BA with a notch (3 mm depth, 1 mm width);

DETAILED DESCRIPTION OF THE INVENTION

Figure 1:
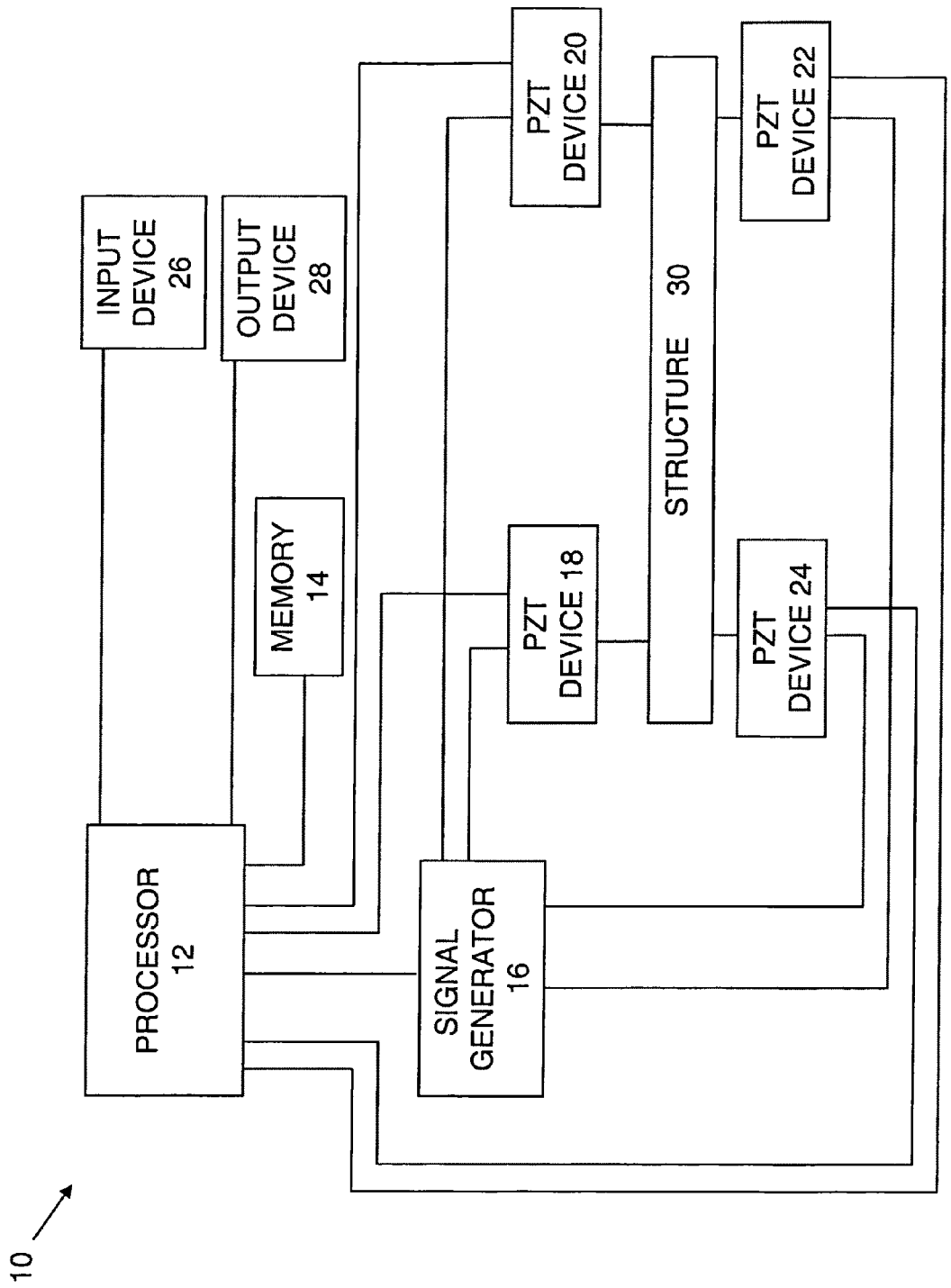
FIG. 1 illustrates one embodiment of a system according to the present invention.

FIG. 1 illustrates one embodiment of a system 10 according to the present invention. In that embodiment, the system 10 includes a processor 12, a computer readable memory 14, a signal generator 16, a plurality of piezoelectric transducer devices 18, 20, 22, 24, an input device 26, and an output device 28. Also shown in FIG. 1 is a material or structure 30 to be analyzed by the system 10 or in which damage is to be detected or the state is to be otherwise be determined.

The processor 12 controls the signal generator 16 and receives input from the input device 26 and provides signals to control the output device 28. The processor 12 is also connected to the memory 14. The processor 12 may be connected directly to the piezoelectric devices 18, 20, 22, 24, or the processor 12 may be connected indirectly to those devices, such as via the signal generator 16 or other devices. In some embodiments, the processor 12 is directly connected to some of the piezoelectric devices and indirectly connected to the remaining piezoelectric devices via the signal generator 16. For example, the processor 12 may be connected only to the piezoelectric devices that sense signals and provide data to the processor 12, and the signal generator 16 may be connected to only the piezoelectric devices that generate signals. In other embodiments, the signal generator 16 may be connected to all piezoelectric devices 18, 20, 22, 24 and pass signals to and from the processor 12. Other variations are also possible.

The memory 14 includes computer readable instructions which, when executed by the processor 12, cause the processor 12 to perform certain functions, as described herein. The memory 14 may be separate from the processor 12, or the memory 14 may be integrated with the processor 12. The memory 14 may also include more than one memory device, one or more of which may be integrated with the processor 12 and one or more may be separate.

The signal generator 16 receives input signals from the processor 12 and generates signals that are sent to the piezoelectric devices 18, 20, 22, 24. The signal generator 16 is illustrated as a device separate from the processor 12, although it may be integrated with the processor 12, such as when the processor 12 generates the signals sent to the piezoelectric devices 18, 20, 22, 24. Other variations are also possible, such as when the signal generator is integrated with the piezoelectric devices 18, 20, 22, 24, so that the processor 12 sends a control signal to the piezoelectric devices 18, 20, 22, 24, and the piezoelectric devices 18, 20, 22, 24 generate the necessary signals for their proper operation.

The piezoelectric devices 18, 20, 22, 24 are connected to the structure 30. The piezoelectric devices 18, 20, 22, 24 generate and sense signals in the structure 30. The piezoelectric devices 18, 20, 22, 24 may each includes a single piezoelectric transducer which both generates and senses the signals, or each of the piezoelectric devices 18, 20, 22, 24 may include a piezoelectric transducer to generate the signals and a separate piezoelectric transducer to sense signals in the structure 30. The piezoelectric devices 18, 20, 22, 24 may be, for example, lead zirconate titanate ("PZT") devices. Other forms of piezoelectric devices also exist and may be used with the present invention. Although the present invention will generally be described in terms of and with reference to PZT devices, the present invention is not limited to PZT piezoelectric devices, and the present invention may be used with other types of piezoelectric devices.

The input device 26 may be a keyboard, a touchscreen, a computer mouse, or other forms of inputting information from a user.

The output device 28 may be a video display or other forms of outputting information to a user.

Many variations are possible with the system 10 according to the present invention. For example, more than one processor 12, memory 14, signal generator 16, input device 26, and output device 28 may be present in the system 10. Also, four PZT devices 18, 20, 22, 24 are illustrated, although different numbers of PZT devices may be used with the present invention. For example, in some embodiments the system 10 may use fewer than four PZT devices, and in other embodiments the system 10 may use more than four PZT devices. Many other variations are possible. For example, devices not shown in FIG. 1 may also be included in the system 10, and devices shown in FIG. 1 may be combined or integrated together into a single device, or omitted.

The present invention will generally be described in terms of embodiments using a time reversal processes, followed by a description of embodiments utilizing polarization characteristics of piezoelectric materials, and finally by a description of embodiments utilizing dual piezoelectric transducers attached on a single surface. The descriptions provided herein are illustrative and not limiting, and other variations and embodiments of the present invention are also disclosed.

Introduction to Lamb Waves

All elastic waves including body and guided waves are governed by the same set of partial differential equations (Rose J L. Ultrasonic Waves in Solid Media, Cambridge University Press: Cambridge UK, 1999). The primary difference is that, while body waves are not constrained by any boundaries, guided waves need to satisfy the boundary conditions imposed by the physical systems as well as the governing equations. Lamb waves are one type of guided waves that exist in thin plate-like structures, and they are plane strain waves constrained by two free surfaces (Lamb, H. "On Waves in an Elastic Plate." Proc. Roy. Soc. London, Ser. A 93, 114-128, 1917). The advances in sensor and hardware technologies for efficient generation and detection of Lamb waves and the increased usage of solid composites in load-carrying structures has led to an explosion of studies that use Lamb waves for detecting defects in composite structures [Su Z Q, Ye L, Lu Y. Guided Lamb waves for identification of damage in composite structures: A review. Journal of sound and vibration 2006; 295 (3-5): 753-780; Di Scalea F L, Rizzo P, Marzani A. Propagation of ultrasonic guided waves in lap-shear adhesive joints: Case of incident A0 Lamb wave. Journal of the Acoustical Society of America 2004; 115(1):146-156. DOI: 10.1121/1.1630999; Paget C, Grondel S, Levin K, Delebarre C. Damage assessment in composites by Lamb waves and wavelet coefficients. Smart Materials and Structures 2003; 12:393-402. DOI: 10.1088/0964-1726112/3/310; Giurgiutiu V. Embedded NDE with Piezoelectric Wafer Active Sensors in Aerospace Applications. Journal of Materials 2003; Sohn H, Park G, Wait J, Limback N, Farrar C. Wavelet-Based Active Sensing for Delamination Detection in Composite Structures. Smart Materials and Structures 2004; 13:153-160. DOI: 10.1088/0964-1726/13/1/017; Sun Z, Rose J, Zaidi M. A Phased Array Guided Wave Approach to Adhesive Bonded Structural Integrity Analysis. Materials Evaluation 2002; Badcock R, Birt E. The use of 0-3 piezocomposite embedded Lamb wave sensors for detection of damage in advanced fiber composites. Smart Materials and Structures 1999; 9(3):291-297; Tan K, Guo N, Wong B, Tui C. Comparison of Lamb waves and pulse echo in detection of near-surface defects in laminate plates. NDT&E International 1995; 28(4):215-224; Tan K, Guo N, Wong B, Tui C. Experimental Evaluation of Delaminations in Composite Plates by the Use of Lamb Waves. Composites Science and Technology 1995; 53(1):77-84]. Because Lamb waves are guided and constrained by two free surfaces, the Lamb waves can propagate a relatively long distance without much attenuation. This long sensing range makes Lamb waves attractive for damage diagnosis.

Unlike body waves, the propagation of Lamb waves is, however, complicated due to their dispersive and multimode characteristics. Theoretically, the dispersion and multimodes of Lamb waves can be investigated by solving Rayleigh-Lamb equations defined for the symmetrical and anti-symmetrical modes on an infinite plate with a thickness 2h.

$$(k^2+s^2)^2 \cos h(qh)\sin h(sh) - 4k^2qs \sin h(qh)\cos h(sh) = 0 \quad (1)$$

$$(k^2+s^2)^2 \sin h(qh)\cos h(sh) - 4k^2qs \cos h(qh)\sin h(sh) = 0 \quad (2)$$

where $q^2=k^2-k_l^2$ and $s^2=k^2-k_t^2$. Furthermore, k denotes a wave number, and $k_l$ and $k_t$ are the wave numbers for the longitudinal and shear modes, respectively. It should be noted that there exist multiple wave modes that satisfy Equation (1) and (2). The dispersion curve can be expressed in terms of the product of the excitation frequency and the plate thickness versus the group velocity $C_g$, which is defined as:

$$C_g = \frac{d\omega}{dk} \quad (3)$$

where ω denotes an angular frequency. For a uniform plate with constant thickness, the dispersion curve can be represented as a function of the frequency as shown in FIG. 2.

Figure 2:
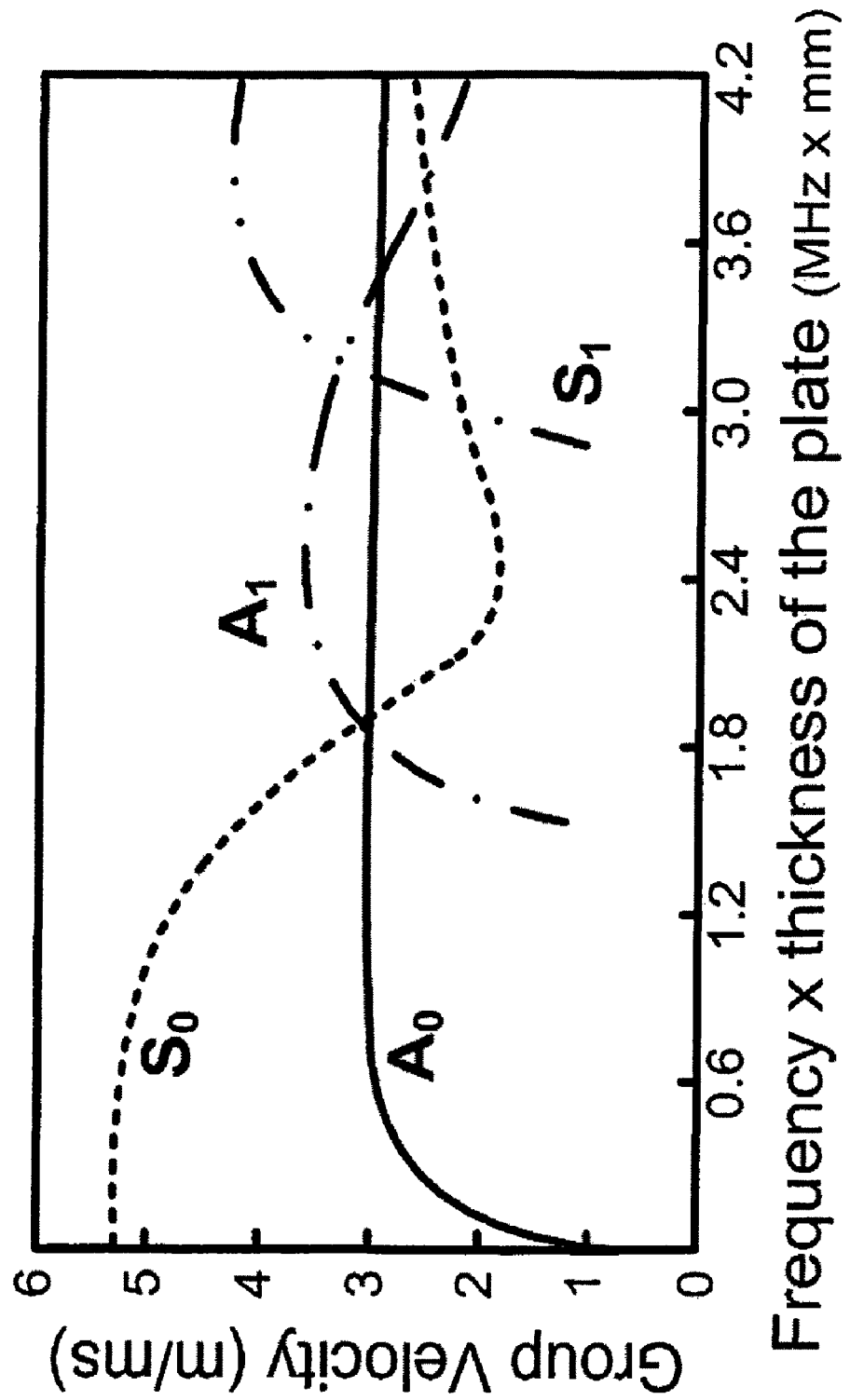
FIG. 2 illustrates a typical dispersion curve of Lamb waves in a thin plate.

FIG. 2 illustrates two distinct velocity dispersion characteristics of Lamb waves. The first dispersion is velocity dispersion within a single mode, and it is referred to as the within-mode dispersion (often referred to as group velocity dispersion) in this application. This within-mode dispersion is caused by the frequency dependency of a single Lamb wave mode. That is, the different frequency components in a single mode travel at different speeds, and this within-mode dispersion results in the spreading of the wave packet as it propagates. The second one is velocity dispersion among multiple modes and referred to as the multimode dispersion (often referred to as modal dispersion) hereafter. This multimode dispersion exists because different modes at a given frequency travel at different speeds. Therefore, when an input waveform with a discrete driving frequency is applied to a thin medium, it is separated into multiple modes, traveling at different speeds. Finally, the amplitude attenuation of a Lamb wave is also frequency dependent, and it is called amplitude dispersion. Due to these unique dispersion characteristics of Lamb waves, time reversibility of Lamb wave signals can be complicated.

Reciprocity of Elastic Waves

To fully appreciate the time reversibility of Lamb waves, it is necessary to understand the reciprocity of wave propagation first. The starting point of the reciprocity of wave propagation is the local reciprocity theorem that can be formulated from two elastodynamic states of a finite body denoted by subscripts I and II:

$$u_{II} \cdot (b_I - \rho \ddot{u}_I) = \nabla \cdot (\sigma_{II} \cdot u_I - \sigma_I \cdot u_{II}) \quad (4)$$

where u, b, ρ, σ, ∇ and ü denote a displacement field vector, a body force vector, material density, a stress tensor, divergence of a vector, and the second derivative of u with respect to time, respectively. When Eq. (4) is integrated over a structural domain V with a boundary S of the finite body, the global reciprocity equation can be obtained:

$$\int_V [u_{II} \cdot (b_I - \rho \ddot{u}_I) - u_I \cdot (b_{II} - \rho \ddot{u}_{II})] dV = \int_S (t_{II} \cdot u_I - t_I \cdot u_{II}) dS \quad (5)$$

where t denotes a traction boundary condition along the boundary S. Note that the volume integration of the right-hand side of Eq. (4) is replaced by the surface integral in Eq. (5) using the divergence theorem and Cauchy's formula. For a steady-state time-invariant system, u, b and t in Eq. (5) can be expressed as harmonic functions with the initial conditions of u, b, and t being zero:

$$u(x,t)=\hat{u}(x)e^{-i\omega t} b(x,t)=\hat{b}(x)e^{-i\omega t} t(x,t)=\hat{t}(x)e^{-i\omega t} \quad (6)$$

where x and the hat on a variable represent the location vector with respect to a reference point and the amplitude of each variable, respectively. Substituting Eq. (6) into Eq. (5) results in the following equation:

$$\int_V (\hat{u}_{II} \cdot \hat{b}_I - \hat{u}_I \cdot \hat{b}_{II}) dV = \int_S (\hat{t}_{II} \cdot \hat{u}_I - \hat{t}_I \cdot \hat{u}_{II}) dS \quad (7)$$

If there exist no body forces in the finite body at dynamic states I and II, the left-hand side of Eq. (7) vanishes and the global reciprocity of elastodynamics can be simplified as follows:

$$\int_S (\hat{t}_{II} \cdot \hat{u}_I - \hat{t}_I \cdot \hat{u}_{II}) dS = 0 \quad (8)$$

Eq. (8) indicates that the work done by traction force $\hat{t}_I$ on displacements $\hat{u}_{II}$ is equal to the work done by traction force $\hat{t}_{II}$ on displacements $\hat{u}_I$. Note that $\hat{u}_I$ and $\hat{u}_{II}$ are displacements produced by $\hat{t}_I$ and $\hat{t}_{II}$, respectively. This reciprocity can be viewed as an extension of the Betti's reciprocal relation in elastostatics to elastodynamics, and it constitutes the foundation for the following time reversal acoustics.

Introduction of Time Reversal Acoustics

The propagation of body waves in elastic media is a classical topic covered in many elasticity textbooks. By definition, the body waves propagate throughout a medium, which is not constrained by boundaries. Body wave characteristics are described by the Navier governing equations, and they can be further divided into pressure waves and shear waves. In time reversal acoustics, an input body wave can be refocused at the source location if a response signal measured at a distinct location is time-reversed (literally the time point at the end of the response signal becomes the starting time point) and reemitted to the original excitation location. This phenomenon is referred to as time reversibility of body waves, and this unique feature of refocusing has found applications in lithotripsy, ultrasonic brain surgery, NDT, and acoustic communications.

Extension of Time Reversal Acoustics to Lamb Waves

While the TRP for non-dispersive body waves has been well-established, the study of the TRP for Lamb waves is still relatively new. Because of dispersion and multimodal characteristics of Lamb waves, the time reversibility of Lamb waves becomes complicated and it has limited the applicability of the TRP to Lamb waves. This section intends to describe how the TRP works for Lamb wave propagations.

Figure 3:
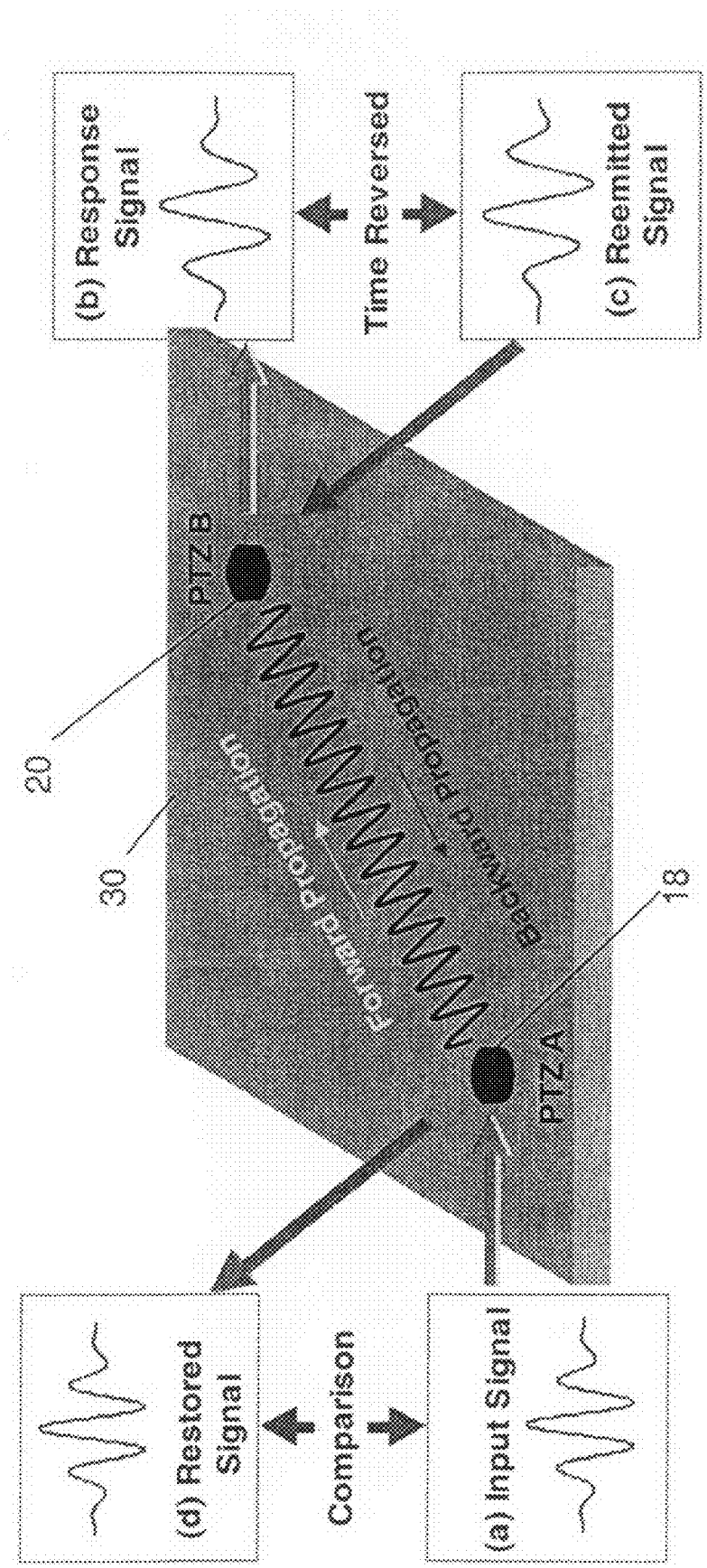
FIG. 3 illustrates a schematic outline of the time reversal process applied to a plate structure.

The TRP is first formulated in the frequency domain incorporating the PZTs used for exciting and measuring Lamb waves [FIG. 3]. Based on the piezoelectricity of PZT materials, an electrical voltage $V(\omega)$ applied to a PZT wafer is converted to a mechanical strain $\epsilon(\omega)$ through the following electro-mechanical efficiency coefficient $k_a(\omega)$:

$$\epsilon(\omega) = k_a(\omega) V(\omega) \quad (9)$$

On the other hand, a voltage is generated when a PZT wafer is subjected to a mechanical strain. This conversion from the mechanical strain to the voltage output is related by the other mechanical-electro efficient coefficient, $k_s(\omega)$. Note that all field variables in Eq. (9) are frequency dependent, and $\omega$ denotes an angular frequency. Hereafter, the angular frequency is omitted from the entire field variables for simplicity unless stated otherwise.

When an excitation voltage is applied to PZT A as shown in FIG. 3(a), the corresponding response voltage at PZT B can be represented by the following equation;

$$V_B = k_s G k_a V_A \quad (10)$$

where G is the structure's transfer function relating an input strain at PZT A to an output strain at PZT B. Here, the input voltage applied at PZT A, $V_A$, is first converted to a mechanical strain via $k_a$. Then, the corresponding response strain at PZT B is converted to the output voltage at PZT B, $V_B$ through $k_s$ [FIG. 3(b)].

In the second step of the TRP, the measured response voltage, $V_B$, is reversed in the time domain before it is reemitted back to PZT B [FIG. 3(c)]. This TRP in the time domain is equivalent to taking a complex conjugate of the signal in the frequency domain. In the final step, the reversed version of $V_B$ is applied back to PZT B, and the corresponding response is measured at PZT A. This final response at PZT A is referred to as the "reconstructed" signal in this application. The reconstructed voltage signal at PZT A, $V_R$, can be related to the response voltage, $V_B$, in the previous step as follows;

$$V_R = k_s G k_a V_B^* \quad (11)$$

where the superscript * denotes the complex conjugate operation. Note that the transfer function in Eq. (11) is assumed to be identical to the one in Eq. (10) based on the reciprocity previously described hereinabove. By inserting Eq. (10) into Eq. (11), the reconstructed signal, $V_R$, is related to the original input signal, $V_A$;

$$V_R = k_s G k_a V_B^* = k_s G k_a k_s^* G^* k_a^* V_A^* = \Gamma K K^* V_A^* \quad (12)$$

where $K = k_s k_a$, and $\Gamma$ is the time reversal operator defined as $\Gamma = GG^*$.

If the time reversal operator and the mechanical-electro coefficients are assumed to be constant over the frequency range of interest, Eq. (12) indicates that the reconstructed signal, $V_R$, is a "time reversed" and "scaled" version of the original input signal $V_A$ [FIG. 3(d)]. That is, the "shape" of the original input signal should be at least reproduced by the reconstructed signal during the TRP.

In reality, the time reversal operator and the mechanical-electro coefficients are frequency dependent for Lamb waves causing signal components at different frequencies to travel at different speeds and attenuation rates. Therefore, the shape of the reconstructed signal will not be identical to that of the original input signal for Lamb wave propagations.

Theoretical Understanding of the TRP for Lamb Waves

Frequency Dependency of the TRP

Figure 4:
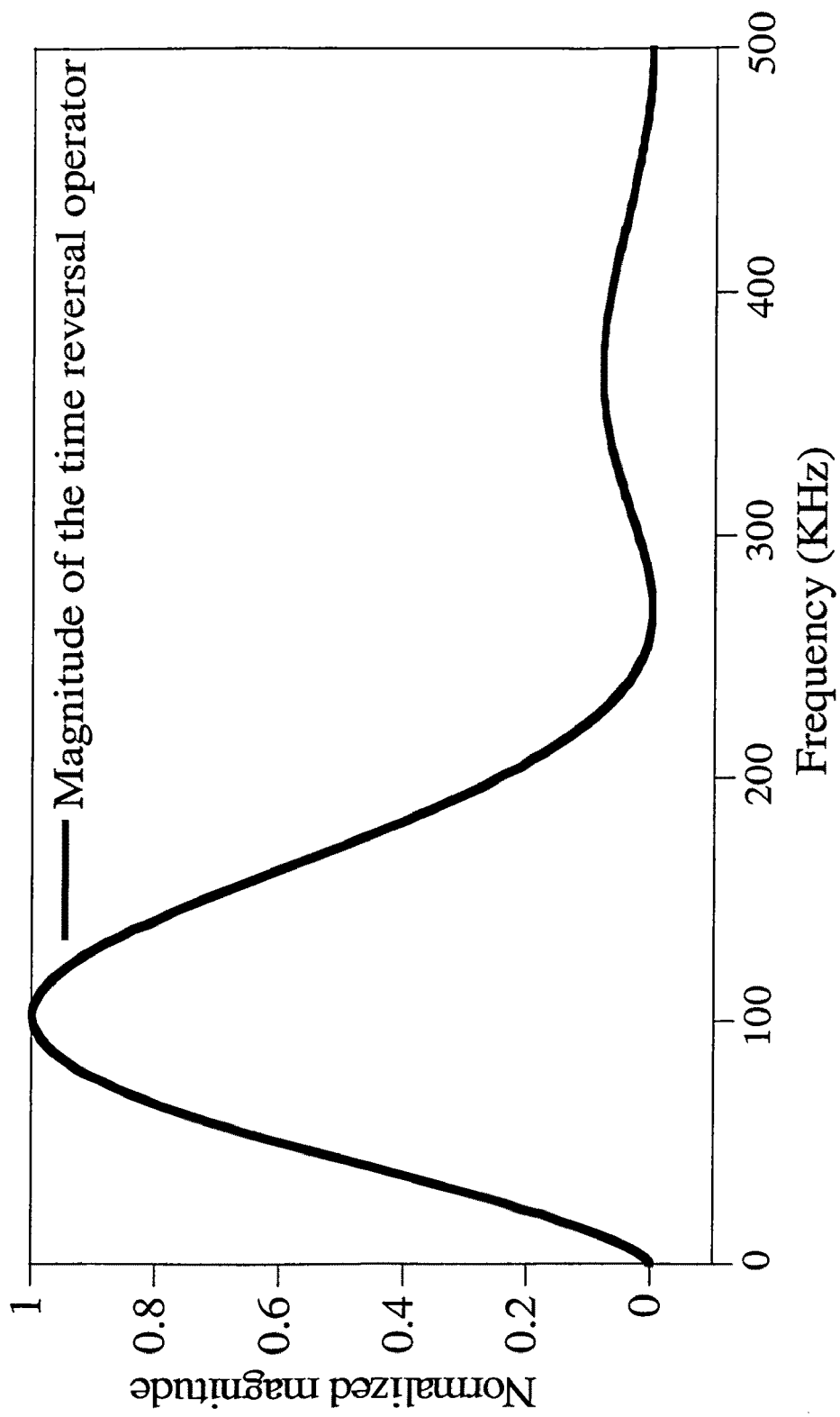
FIG. 4 illustrates a normalized time reversal operator of the A0 mode.

Park et al. (Park H W, Sohn H, Law K H, Farrar C R. Time Reversal Active Sensing for Health Monitoring of a Composite Plate. Journal of Sound and Vibration 2006 (in press)) investigated the time reversibility of Lamb waves on a composite plate and introduced the time reversal operator into the Lamb wave equation based on the Mindlin plate theory (Rose, L. R. F. and Wang, C. H., "Mindlin plate theory for damage detection: source solution," Journal of the Acoustical Society of America, 116, pp. 154-171, 2004). Because of the amplitude dispersion of Lamb waves, the time reversal operator varies with respect to frequency as shown in FIG. 4, and wave components at different frequency values are non-uniformly amplified during the TRP. Due to this amplitude dispersion of the TRP, the original input signal cannot be properly reconstructed if the input signal consists of multiple frequency components such as a broadband input signal. A narrowband excitation has been used to avoid this issue. Note that Park et al. (2006) considered only the fundamental anti-symmetric mode. In reality, the existence of multi-modes complicates the TRP of Lamb waves. The effects of within-mode dispersion, multimode dispersion, and reflections on time reversal are subsequently described.

The present invention will often be described in terms of utilizing a "narrowband" signal. "Narrowband" is often taken to mean a signal having only a single frequency component. However, as a practical matter, no signal is entirely a single frequency component, and "narrowband" can be further defined as a signal that is band limited around a main frequency. The "main frequency" means the frequency having the greatest amplitude and, it is to be expected, the signal intended to be generated. For example, in some embodiments the present invention utilizes a narrowband signal with a bandwidth that is limited to ten percent (10%) of the main frequency. For example, if the main frequency is 100 kHz, the bandwidth of the signal is 10 kHz or less. Other variations are also possible, such as different main frequencies and bandwidths greater than and less than ten percent (10%), and in which the bandwidth of the signal may or may not be centered around the main frequency. Also, in cases where signals are measured very precisely, "narrowband" may be further defined, such as wherein at least a predetermined percentage of the signal power must be within a certain bandwidth. For example, at least ninety percent (90%) of the signal power is within ten percent (10%) of the main frequency.

Figure 5:
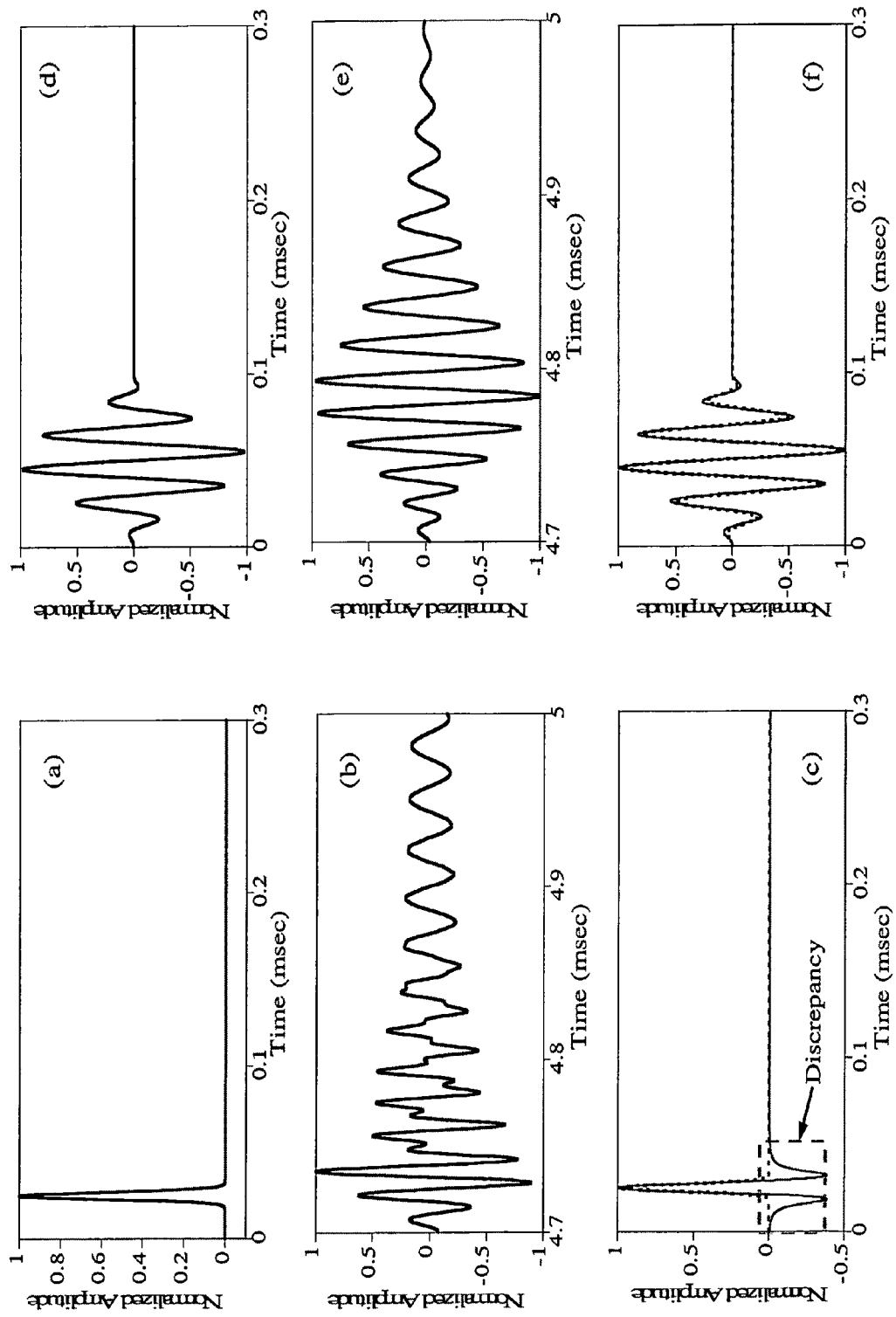
FIG. 5 illustrates a reconstruction of input signals using broadband and narrowband input signals through a numerically simulated time reversal process: (a) Original broadband input signal—Gaussian pulse. (b) Response signal—Gaussian pulse. (c) Original input (dotted) and reconstructed input (solid) signal—Gaussian pulse. (d) Original narrowband input signal—100 kHz toneburst. (e) Response signal-100 kHz toneburst. (f) Original input (dotted) and reconstructed input (solid) signal-100 kHz toneburst. (Park H W, Sohn H, Law K H, Farrar C R. Time Reversal Active Sensing for Health Monitoring of a Composite Plate. Journal of Sound and Vibration 2006 (in press))

To justify the use of a narrowband excitation for the TRP, a numerical example of the TRP based on the Mindlin plate theory is provided in FIG. 5. In particular, broadband (a Gaussian pulse [FIG. 5(a)]) and narrowband (a 100 kHz toneburst [FIG. 5(d)]) input signals are employed to numerically investigate the frequency dependency of the time reversal process. The specification of a composite plate and PZT wafers used in this numerical simulation are identical to those reported in Park et al. (2006). The distance between the PZT pair is assumed to be long enough (5 m) so that the within-mode dispersion of Lamb waves can be observed at the response PZT [FIGS. 5 (b) and (e)]. When the response signals are reversed in the time domain and reemitted to the input PZT, the within-mode dispersion of Lamb waves is compensated [FIGS. 5 (c) and (f)].

As demonstrated here, the within-mode dispersion can be compensated during the TRP. Some wave components within the single Lamb wave mode travel at higher speeds and arrive at a sensing point earlier than those traveling at lower speeds. However, during the TRP at the sensing location, the wave components, which travel at slower speeds and arrive at the sensing point later, are reemitted to the original source location first. Therefore, all wave components traveling at different speeds concurrently converge at the source point during the TRP, compensating the within-mode dispersion of Lamb waves.

Due to the amplitude dispersion, however, the shape of the original pulse is not fully recovered when the Gaussian input is used [FIG. 5(c)]. The various frequency components of the Gaussian input are non-uniformly scaled and superimposed during the TRP as indicated in FIG. 5 (c). On the other hand, the shape of the reconstructed tone burst waveform is practically identical to that of the original input tone burst because the amplification of the time reversal operator is almost uniform for a limited frequency band. [FIG. 5(f)].

This section illustrates that the frequency dependency of the TRP can be minimized by using a narrowband excitation signal rather than a broadband excitation. Although the use of a narrowband input can enhance the TRP, the shape of the reconstructed signal still will not be identical to that of the original input signal due to the multimode dispersion and reflections from the structure's boundaries. Their effects on the TRP are theoretically described in the following subsections.

Understanding the Effect of the within-Mode Dispersion on the TRP

Hereinabove, it is shown that the amplitude dispersion of the TRP can be minimized by using a narrowband excitation signal rather than a broadband excitation. In this section, the effect of within-mode dispersion on the TRP is mathematically described by considering a single symmetric or anti-symmetric mode induced by a narrowband input excitation. In the following section, this description is extended for general Lamb wave propagations where multiple symmetric and anti-symmetric modes exist.

Considering the amplitude and within-mode dispersion of a single symmetric/anti-symmetric mode, the transfer function G in Eq. (2) can be simplified as follows:

$$G = ce^{-ikr} \quad (13)$$

where c and k denote the amplitude dispersion function and the wave number of a specific mode while r denotes a distance between actuating and sensing PZT wafers, respectively. In turn, the time reversal operator $\Gamma$ in Eq. (12) can be expressed as follows:

$$\Gamma = GG^* = (ce^{-ikr})(c^*e^{ikr}) = cc^* \quad (14)$$

Eq. (14) shows that the within-mode dispersion in the forwarding process, $e^{-ikr}$, is automatically compensated during the time reversal operation, resulting in only amplitude attenuation at the end. By substituting Eq. (14) to Eq. (12), the relationship between the reconstructed signal and the original input signal can be simplified:

$$V_R = cc^*KK^*V_A^* \quad (15)$$

When a narrowband toneburst signal is applied around a central frequency $\bar{\omega}$, the amplitude dispersion (attenuation) function and electro-mechanical transduction coefficients can be assumed to be constant over the narrow frequency band. Then, the reconstructed input signal in the time domain can be obtained by taking the inverse Fourier transform of Eq. (15):

$$\begin{aligned} V_R(t) &= \frac{1}{2\pi}\int_{-\infty}^{\infty} V_R e^{i\omega t} dt \\ &= \frac{1}{2\pi}\int_{-\infty}^{\infty} cc^*KK^*V_A^* e^{i\omega t} d\omega \\ &= \bar{C}\bar{K} V_A(T-t) \end{aligned} \quad (16)$$

where $\bar{C} = c(\bar{\omega})c^*(\bar{\omega})$, $\bar{K} = K(\bar{\omega})K^*(\bar{\omega})$, and T denotes the total time duration of the measured reconstructed signal. Note that the complex conjugate of the input signal in the frequency domain is equivalent to the time reversed version of the original input in the time domain after the inverse Fourier transform.

Eq. (16) confirms again that, as long as a single Lamb wave mode is concerned, the reconstructed signal is simply a "time-reversed" and "scaled" version of the original input signal as previously described in Eq. (12). Note that the within-mode dispersion of a single mode is compensated during the TRP, and it does not affect the time reversibility. In the next subsection, the time reversibility is extended considering the multimode dispersion of multiple symmetric and anti-symmetric modes.

Understanding the Effect of Multimodes on the TRP

Figure 6:
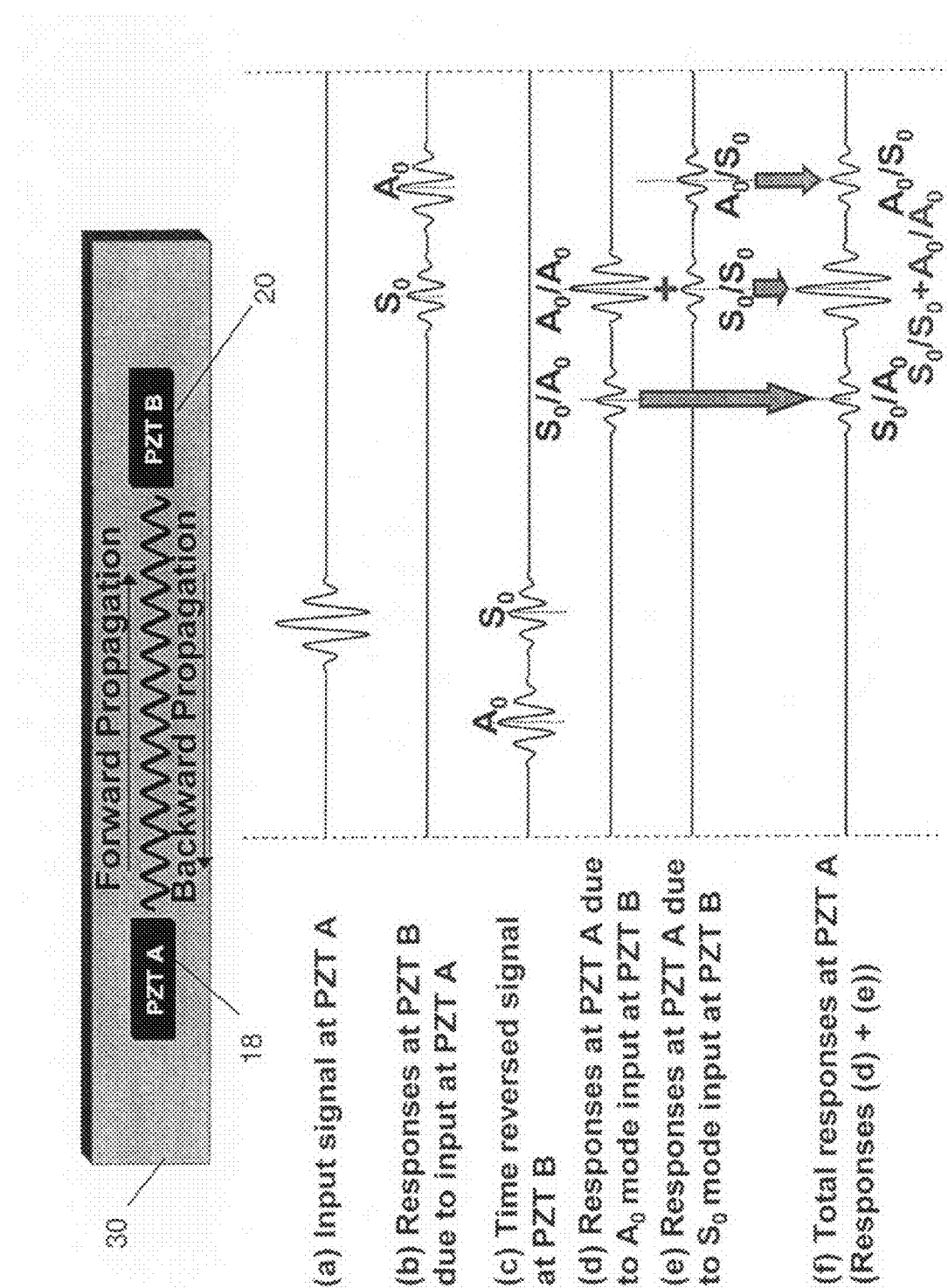
FIG. 6 illustrates the effect of multi-modes on the time reversal process (Note: S0/A0 denotes S0 mode produced at PZT A due to A0 mode input at PZT B. A0/S0, S0/S0, and A0/A0 are similarly defined)

As previously addressed, the multimodal characteristics of Lamb waves complicate the TRP. The effect of the multimode characteristic is schematically shown in FIG. 6. When a toneburst signal is exerted to PZT A [FIG. 6(a)], multimodes are generated at PZT B [FIG. 6(b)]. In FIG. 6, the narrowband input frequency is selected so that only the first symmetric ($S_0$) and anti-symmetric ($A_0$) modes are generated. When the response signal is reversed in the time domain and reemitted to PZT B [FIG. 6(c)], each of the $A_0$ or $S_0$ modes creates both $S_0$ and $A_0$ modes producing a total of four modes in the reconstructed signal [FIGS. 6 (d) and (e)]. In FIG. 6, $S_0/A_0$ denotes the $S_0$ mode measured at PZT A due to the $A_0$ mode input at PZT B. $A_0/S_0$, $S_0/S_0$, and $A_0/A_0$ are similarly defined. After superposition of signals in FIGS. 6 (d) and (e), the reconstructed signal consists of the main mode at the middle and two sidebands around the main mode [FIG. 6(f)]. Note that the main mode in the middle is the superposition of the $A_0/A_0$ and $S_0/S_0$ modes and "symmetric" side bands are produced as a result of $A_0$ and $S_0$ mode coupling. Finally, the shape of the main mode will be practically identical to that of the original input signal.

Considering this multimode effect on the TRP, the reconstructed signal will be composed of the following four mode groups:

$$V_R(t) = V_R^{SS}(t) + V_R^{AA}(t) + V_R^{SA}(t) + V_R^{AS}(t) \tag{17}$$

where $V_R^{SA}(t)$ represents the symmetric modes in the reconstructed signal generated by the anti-symmetric modes in the forward signal, and $V_R^{SS}(t)$, $V_R^{AA}(t)$, and $V_R^{AS}(t)$ are defined in a similar fashion. Consequently, the time reversal operator $\Gamma$ in Eq. (12) is also decomposed to those associated with symmetric and anti-symmetric modes.

$$\Gamma = \Gamma^{SS} + \Gamma^{AA} + \Gamma^{SA} + \Gamma^{AS} \tag{18}$$

Initially, the coupling effect among symmetric modes ($V_R^{SS}(t)$ and $\Gamma^{SS}$) is explained, and this description is extended for multiple symmetric and anti-symmetric modes. For brevity, the superscription "S" denoting the symmetric mode is omitted until all multiple modes are included at the end of this section. Considering the coupling among symmetric modes, Eq. (15) can be extended as follows:

$$\Gamma = \sum_{p=1}^{n_S} \sum_{q=1}^{n_S} g_p g_q^* \tag{19}$$

where $g_p$ denotes the transfer function of the pth symmetric mode, and $n_S$, represents the total number of symmetric modes at a given excitation frequency $\overline{\omega}$.

Similar to Eq. (14), $g_p$ can be expressed as a function of the amplitude and velocity dispersions $$g_p = c_p e^{-ik_p r} \tag{20}$$

where $c_p$ and $k_p$ denote the amplitude dispersion function and the wave number of the pth symmetric mode. Substituting Eq. (20) into Eq. (19) results in:

$$\Gamma = \sum_{p=1}^{n_S} \sum_{q=1}^{n_S} g_p g_q^* = \sum_{p=1}^{n_S} \sum_{q=1}^{n_S} c_p c_q^* e^{ir[k_p - k_q]} = \sum_{p=1}^{n_S} \sum_{q=1}^{n_S} C_{pq} e^{i\theta_{pq}} \tag{21}$$

where, $\theta_{pq} = r[k_p - k_q]$ and $C_{pq} = c_p c_q^*$. Subsequently, the reconstructed input signal associated with symmetric mode coupling can be expressed as follows:

$$V_R = \Gamma KK^* V_A^* = \sum_{p=1}^{n_S} \sum_{q=1}^{n_S} C_{pq} e^{i\theta_{pq}} KK^* V_A^* \tag{22}$$

Similar to Eq. (16), the reconstructed input signal in the time domain can be obtained by taking the inverse Fourier transform of Eq. (22) when an original input signal is a narrowband toneburst with a center frequency of $\overline{\omega}$:

$$V_R(t) = \sum_{p=1}^{n_S} \sum_{q=1}^{n_S} \frac{1}{2\pi} \int_{-\infty}^{\infty} \overline{C}_{pq} \overline{K} V_A^* e^{i(\theta_{pq} + \omega t)} d\omega \tag{23}$$

where. $\overline{C}_{pq} = c_p(\overline{\omega}) c_q^*(\overline{\omega})$ and $\overline{K} = K(\overline{\omega}) K^*(\overline{\omega})$. Because $\theta_{pq}$ in Eq. (23) equals to zero when p=q, Eq. (23) can be rewritten as follows:

$$V_R(t) = \tag{24}$$

$$V_A(T-t) \sum_{p=1}^{n_S} \overline{C}_{pp} \overline{K} + \sum_{p=1}^{n_S} \sum_{q=1}^{n_S} (1 - \delta_{ij}) \frac{1}{2\pi} \int_{-\infty}^{\infty} \overline{C}_{pq} \overline{K} V_A^* e^{i(\omega t + \theta_{pq})} d\omega$$

where $\delta_{pq} = 0$ if $p \neq q$ and $\delta_{pq} = 1$ if p=q.

Note that there is no closed form solution for the integral term in Eq. (24). To get an approximate solution of this integral, $\theta_{pq}$ is expanded using a Taylor series near the driving frequency $\overline{\omega}$ up to the first order term:

$$\theta_{pq} \approx \theta_{pq}(\overline{\omega}) + \left. \frac{d\theta_{pq}}{d\omega} \right|_{\omega = \overline{\omega}} (\omega - \overline{\omega}) \tag{25}$$

By using the relationships among the angular frequency $\omega$, the wave number k, the group velocity w, and the phase velocity v, Eq. (25) can be expressed as follows:

$$\theta_{pq} \overline{\omega} \tau_{pq} + \omega \overline{t}_{pq} \tag{26}$$

where $$\overline{\tau}_{pq} = \left[ \left\{ \frac{r}{v_p(\overline{\omega})} - \frac{r}{w_p(\overline{\omega})} \right\} - \left\{ \frac{r}{v_q(\overline{\omega})} - \frac{r}{w_q(\overline{\omega})} \right\} \right], \tag{27}$$

$$\overline{t}_{pq} = \left[ \frac{r}{w_p(\overline{\omega})} - \frac{r}{w_q(\overline{\omega})} \right]$$

and $$d\omega = w_p(\omega) dk_p, \quad \omega = v_p(\omega) k_p \tag{28}$$

Using Eqs. (26)-(28), Eq. (24) can be expressed as follows:

$$V_R(t) = \sum_{p=1}^{n_S} \overline{C}_{pp} \overline{K} V_A(T - t) + \tag{29a}$$

$$\sum_{p=1}^{n_S} \sum_{q=1}^{n_S} (1 - \delta_{pq}) \overline{C}_{pq} \overline{K} \cos(\overline{\omega} \tau_{pq}) V_A \{T - (t + \overline{t}_{pq})\} +$$

$$i \sum_{p=1}^{n_S} \sum_{q=1}^{n_S} (1 - \delta_{pq}) \overline{C}_{pq} \overline{K} \sin(\overline{\omega} \tau_{pq}) V_A \{T - (t + \overline{t}_{pq})\}$$

The first term on the right hand side of Eq. (29a) indicates that both within-mode and multimode dispersions are compensated and Lamb wave modes converge to the main mode as long as the identical mode travels in both forwarding and back propagation directions. On the other hand, the second term reveals that, when Lamb waves travel at two different group velocities in the forwarding and back propagation directions, the corresponding modes in the reconstructed input signal are shifted in the time domain by $\bar{t}_{pq}$, creating "side bands" around the main mode where the most of the energy converges. Note that the within-mode dispersion in the time domain is still fully compensated in the second term and the time shift $\bar{t}_{pq}$ depends only on the difference between the group velocities of the pth and qth modes. Contrast to the first and second terms in Eq. (29a), the third term represents the higher-order dispersive wave packets that do not converge on the corresponding side bands of the reconstructed input signal and there is no closed form solution for this integral. Finally, because $\bar{\tau}_{pq}=-\bar{\tau}_{qp}$ and $\bar{t}_{pq}=-\bar{t}qp$ in Eq. (27), it can be shown that the reconstructed signal in Eq. (28) is symmetric with respect to the main peak mode in the middle. Note that this symmetry of the reconstructed signal is valid regardless the symmetry of the structure or the PZT transducer layout as long as the input signal is symmetric.

In a similar manner, $V_R^{SA}$, $V_R^{AA}$, and $V_R^{AS}$ terms in Eq. (17) can be calculated as follows:

$$V_R^{SA}(t) = \sum_{p=1}^{n_S} \sum_{q=1}^{n_A} \overline{C}_{pq}^{SA} \overline{K} \cos(\overline{\omega}\tau_{pq}^{SA}) V_A\{T - (t + \bar{t}_{pq}^{SA})\} \quad (29b)$$

$$V_R^{AS}(t) = \sum_{p=1}^{n_A} \sum_{q=1}^{n_S} \overline{C}_{pq}^{AS} \overline{K} \cos(\overline{\omega}\tau_{pq}^{AS}) V_A\{T - (t + \bar{t}_{pq}^{AS})\} \quad (30)$$

$$V_R^{AA}(t) = \sum_{p=1}^{n_A} \overline{C}_{pq}^{AA} \overline{K} V_A(T-t) + \quad (31)$$
$$\sum_{p=1}^{n_A} \sum_{q=1}^{n_A} (1 - \delta_{pq}) \overline{C}_{pq}^{AA} \overline{K} \cos(\overline{\omega}\tau_{pq}^{AA}) V_A\{T - (t + \bar{t}_{pq}^{AA})\}$$

where superscripts S and A denote symmetric and anti-symmetric modes while $n_A$ denotes the total number of anti-symmetric modes at the excitation frequency $\overline{\omega}$. Eqs. (29b) and (30) reveal that the $V_R^{SA}$ and $V_R^{AS}$ terms in the reconstructed input signal do not converge to the main mode but only create additional side bands. The same can be said about $V_R^{AA}$ except that it converges on the main mode when p=q. However, it is noted that the symmetry of the reconstructed signal is still preserved even at the presence of multiple symmetric and anti-symmetric modes.

Understanding the Effect of Reflection on the TRP

Figure 7:
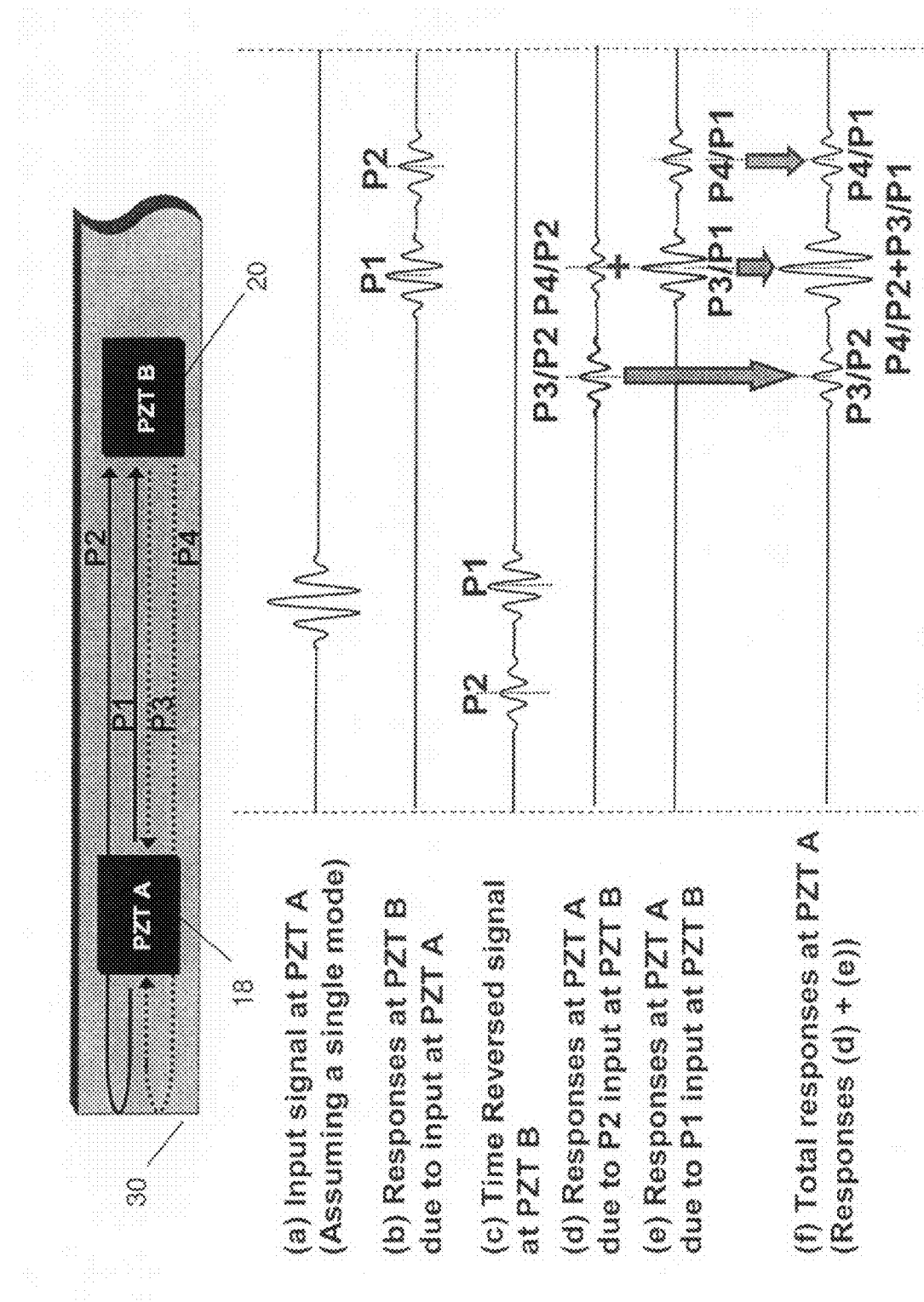
FIG. 7 illustrates the effect of reflections on the TRP (Note: P1 and P3 are waves propagating along the direct path between PZTs A and B, and P2 and P4 are waves reflected at one end of the plate in forward and backward directions. P3/P2 denotes a signal arrived at PZT A through a direct path, when the reflected signal, P2, is emitted back to PZT B after time-reversal. P4/P2, P3/P1, and P4/P1 are similarly defined)

Similar to the multiple Lamb wave modes, the Lamb waves reflected from the boundaries of a structure create additional side bands in the reconstructed signal. The effect of the reflections on the TRP is illustrated in FIG. 7. For simplicity, it is assumed that only a single mode travels unidirectionally and the structure has only one finite boundary where the Lamb wave is reflected. When a single Lamb mode is generated at PZT A and travels to PZT B [FIG. 7(a)], the wave will take two different paths to arrive at PZT B [FIG. 7(b)]. In FIG. 7, P1 and P2 denote modes traveled along direct and reflection paths in a forward propagation direction. P3 and P4 are defined in a similar fashion but in a backward propagation direction. When the P2 mode due to the reflection is emitted back to PZT A [FIG. 7(c)], this mode generates two modes, P3/P2 and P4/P2, in the reconstructed signal due to the two different wave propagation paths in the backward propagation direction [FIG. 7(d)]. Similarly, when P1 is reemitted, it creates additional two modes, P3/P1 and P4/P1 [FIG. 7(e)]. Finally, the reconstructed signal is composed of the main mode in the middle, which is the superposition of P3/P1 and P4/P2, and two symmetric sidebands due to P3/P2 and P4/P1 [FIG. 7(f)]. Note that the symmetry of the reconstructed signal is irrelevant to the symmetry of neither the structure, the PZT layout nor the boundary condition. In the example presented in FIG. 7, there is only one finite boundary where waves can be reflected, but the reconstructed signal is still symmetric. The number of sidebands will increase if there are additional wave reflections.

To examine the effect of the reflections in a more theoretical manner, the time reversal operator $\Gamma$ in Eq. (12) can be decomposed to those associated multiple wave propagation paths between the actuating and sensing PZT wafers. For brevity of description, the discussion is first limited to a single Lamb mode with multiple wave propagation paths:

$$\Gamma = GG^* = \sum_{p=1}^{n_R} \sum_{q=1}^{n_R} g_p g_q^* \quad (32)$$

where subscript p of a field variable denotes a specific wave propagation path, while $n_R$, and $g_p$ represent the total number of traveling paths and an individual transfer function associated with the pth traveling path, respectively.

Considering the amplitude and velocity dispersion of Lamb waves, $g_p$ can be simply expressed as follows:

$$g_p = ce^{-ikr_p} \quad (33)$$

where c, k, and $r_p$ denote the amplitude dispersion function, a wave number, and a traveling distance from the actuating PZT wafer to the sensing PZT wafer associated with the pth traveling path, respectively. Using Eq. (33), Eq. (32) can be expressed as follows:

$$\Gamma = \sum_{p=1}^{n_R} \sum_{q=1}^{n_R} g_i g_j^* = \sum_{p=1}^{n_R} \sum_{q=1}^{n_R} cc^* e^{ik[r_p - r_q]} = \sum_{p=1}^{n_R} \sum_{q=1}^{n_R} Ce^{i\theta_{ipq}} \quad (34)$$

where, $\theta_{ij} = k[r_i - r_j]$ and $C = cc^*$. From Eq. (34), the reconstructed input signal with multiple wave propagation paths can be calculated as follows:

$$V_R = \Gamma KK^* V_A^* = \sum_{p=1}^{n_R} \sum_{q=1}^{n_R} Ce^{i\theta_{pq}} KK^* V_A^* \quad (35)$$

Similar to Eq. (16), the reconstructed input signal in the time domain can be obtained by taking the inverse Fourier transform of Eq. (35) if an original input signal is a narrowband toneburst with a center angular frequency or:

$$V_R(t) = \quad (36)$$
$$V_A(T-t) \sum_{p=1}^{n_R} \overline{C}\overline{K} + \sum_{p=1}^{n_R} \sum_{q=1}^{n_R} (1 - \delta_{pq}) \frac{1}{2\pi} \int_{-\infty}^{\infty} \overline{C}\overline{K} V_A^*(\omega) e^{i(\omega t + \theta_{pq})} d\omega$$

Because the second term in Eq. (36) cannot be directly expressed in terms of $V_A(t)$, it is approximated by procedures similar to Eqs. (25)-(28):

$$V_R(t) = \quad (37)$$
$$\sum_{p=1}^{n_R} \overline{C}\overline{K} V(T-t) + \sum_{p=1}^{n_R} \sum_{q=1}^{n_R} (1 - \delta_{pq}) \overline{C}\overline{K} \cos(\overline{\omega}\tau_{pq}) V_A\{T - (t + \bar{t}_{pq})\}$$

where $$\tau_{pq} = (r_p - r_q)\left\{\frac{1}{v(\overline{\omega})} - \frac{1}{w(\overline{\omega})}\right\}, \quad (38)$$

$$\bar{t}_{pq} = \frac{(r_p - r_q)}{w(\overline{\omega})}$$

Note that Eq. (37) is identical to Eq. (29a) except that the summation is performed over the multiple reflection paths instead of the multiple symmetric modes. Therefore, the reflections create additional side bands similar to the ones created by the multiple modes, but do not change the symmetry of the reconstructed signal regardless of the symmetry of the structure's boundary conditions.

The Effect of PZT Wafer Transducers on the TRP

Figure 8:
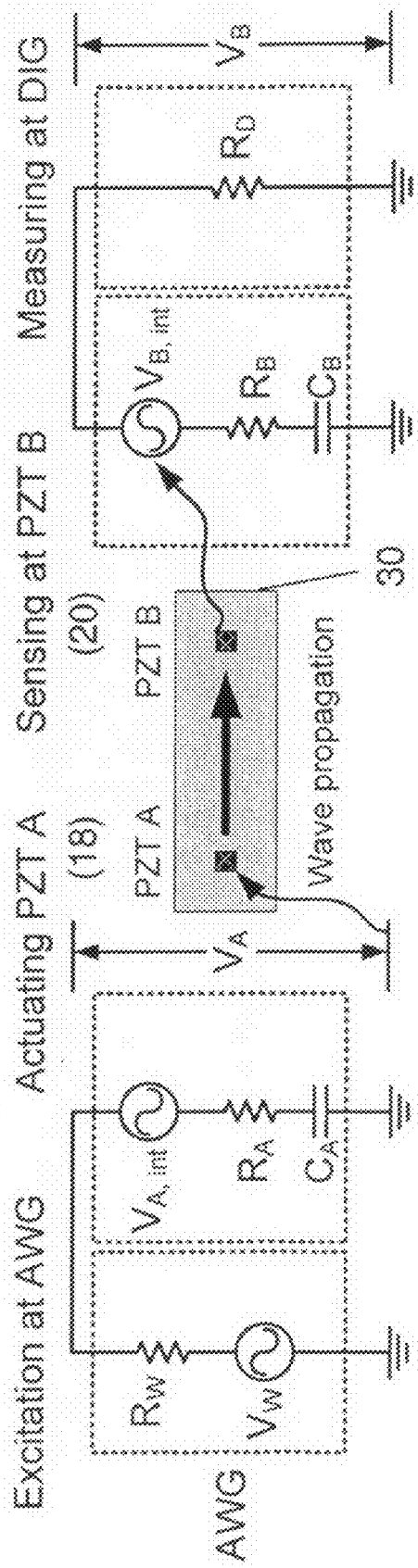
FIG. 8 illustrates an electrical representation of PZT transduces, an AWG, and a DIG.

So far, it has been assumed that the two PZT wafers used for actuating and sensing Lamb waves are identical. In practice, the impedance of each PZT wafer will vary depending on its size and bonding condition, affecting the TRP. In FIG. 8, schematic diagrams of the actuation and sensing PZT transducers or wafer transducers connected to either an arbitrary waveform generator (AWG) or a digitizer (DIG) are shown. The AWG is simulated as an AC voltage source, and its output impedance is denoted as $R_w$. An equivalent circuit model with a series connection between a capacitor ($C_A$ or $C_B$), a voltage source ($V_{A, int}$ or $V_{B, int}$), and in internal resister ($R_A$ or $R_B$) is used to substitute PZT A and PZT B [C. H. Park, "On the Circuit model of Piezoceramics", Journal of intelligent material systems and structures, Vol. 12—July 2001], and $R_D$ represents the impedance of a digitizer (DIG). Note that the proposed circuit model is valid when the exciting frequency is far below the resonant frequency of PZT transducers [C. H. Park]. In this section, the TRP is assumed to be conducted starting from the PZT A, and the reconstructed signal after the TRP will be compared to an original input.

When a cosine input signal is generated by the AWG, the voltage can be expressed as:

$$V_W(t) = A\cos(\omega t) \quad (39)$$

where, $\omega$ represents the angular velocity of the input signal. Then, $V_A(t)$, which is the voltage across the PZT A, can be calculated as follows:

$$V_A(t) = \frac{A\sqrt{(1+\omega^2 C_A^2 R_A(R_W+R_A))^2 + \omega^2 C_A^2 R_W^2}}{1+\omega^2 C_A^2(R_W+R_A)^2} \quad (40)$$

$$\cos\left\{\omega t - \tan^{-1}\left(\frac{\omega C_A R_W}{1+\omega^2 C_A^2 R_A(R_W+R_A)}\right)\right\}$$

$$= a(\omega)\cos(\omega t - \phi_A)$$

Note that the $V_{A, int}$ is assumed to be zero because the PZT A is not mechanically excited, and $\phi_A$ denotes the amount of a phase shift at the PZT A. Now, $V_A(\omega)$ in Eq. (9) is changed into $a(\omega)e^{-i\phi_A}V_A(\omega)$ using Eq. (40).

At the PZT B, the response voltage due to the excitation at the PZT A is derived as:

$$V_{B,int} = k_s G k_a a(\omega) V_A e^{-i\phi_A} \quad (41)$$

where $k_s$, $k_a$, and G represent mechanical-electro efficient coefficient, electro-mechanical efficient coefficient, and structure's transfer function relating an input strain at the PZT A to an output strain at the PZT B, respectively. The voltage measured by the DIG is not affected by the impedance of the PZT B much when $R_D$ value is large enough compared to the magnitude of PZT B's impedance. Therefore, the $V_{B, int}$ is almost identical to $V_B$. After signal $V_B$ is reversed in the time domain and resent to the PZT B, the new input signal is introduced as:

$$V_B = b(\omega)k_s^* G^* k_a^* a(\omega)^* V_A^* e^{-i(\phi_B - \phi_A)} \quad (42)$$

where the superscript * denotes the complex conjugate operation. Note that a phase shift $\phi_B$ is induced by the impedance of the PZT B and the AWG in the same manner as $\phi_A$ is introduced, and $b(\omega)$ is introduced similarly to the $a(\omega)$ in Eq. (40), as well.

Finally, by measuring response from the PZT A using the DIG, a reconstructed signal is obtained as follows:

$$V_R(t) = \frac{1}{2\pi}\int_{-\infty}^{\infty} V_R e^{i\omega t} dt \quad (43)$$

$$= \frac{1}{2\pi}\int_{-\infty}^{\infty} b(\omega)a(\omega)^* k_s k_a k_s^* k_a^* GG^* V_A^* e^{-i(\phi_B - \phi_A)} e^{i\omega t} d\omega$$

Note that Eq. (43) is almost identical to Eq. (16) except for amplitude change and a phase shift. The difference in amplitudes can be compensated by scaling the reconstructed signals. However, the effect of phase shift is still remaining after the scaling. It can be inferred from Eq. (43) that the reconstructed signal will be shifted by the amount of $|\phi_B - \phi_A|$ unless the impedance of the PZT B equals to that of the PZT A. The test results related to the time shift due to the impedance of the PZTs will be shown.

Definition of Time Reversal Related Indices

To measure the symmetry of the reconstructed signal and its closeness to the original input signal, two indices are formulated: time reversibility and symmetry indices.

Figure 9:
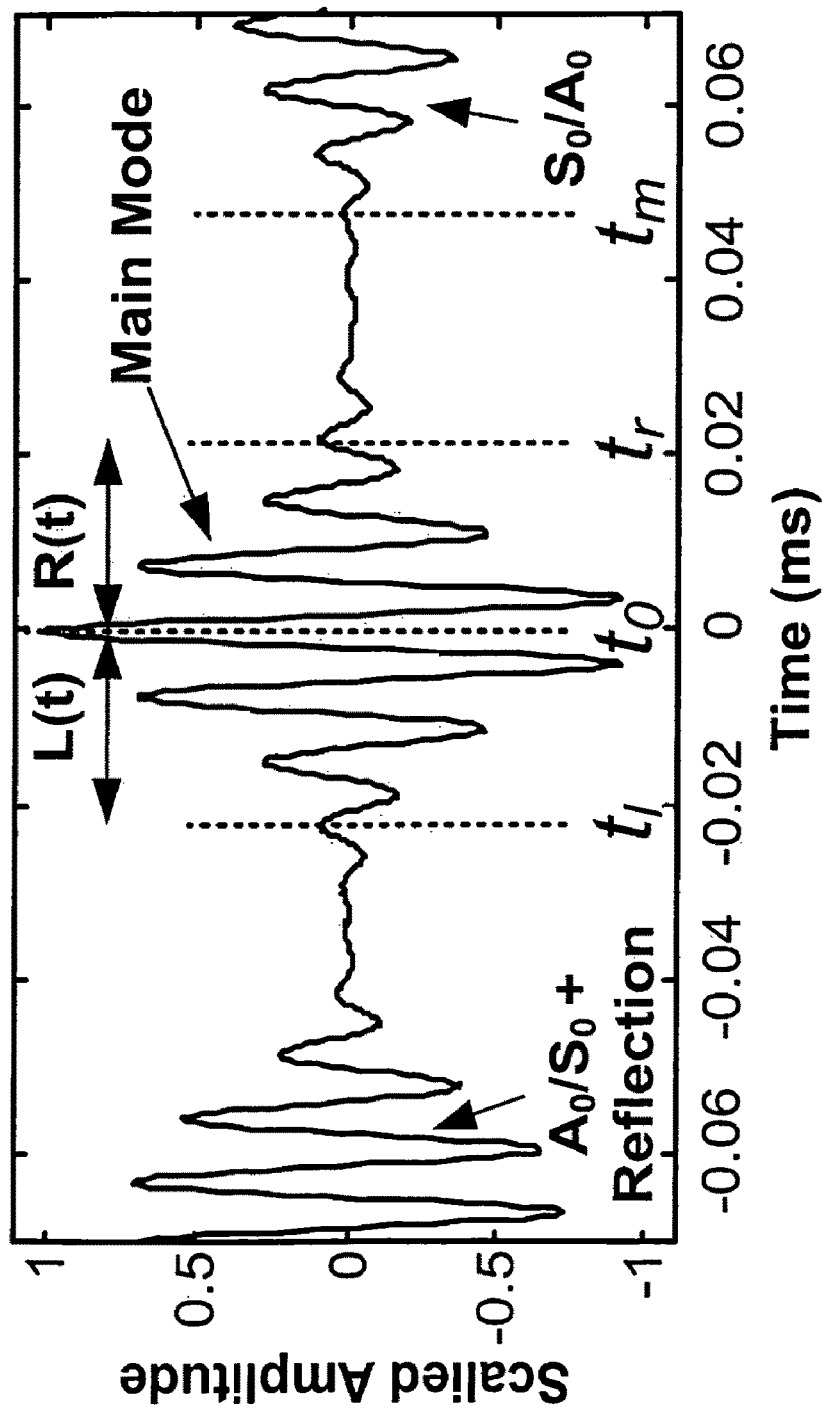
FIG. 9 illustrates the definition of L(t), R(t). t; and tr.

The time reversibility index (TI) is defined so that the shape of the reconstructed signal's main mode can be compared with that of the original input signal. If the shapes of the two signals are identical, TI becomes zero. As the difference between two signals increases, TI approaches to one.

$$TI = 1 - \sqrt{\left\{\int_{t_l}^{t_r} I(t)V(t)dt\right\}^2 / \left\{\int_{t_l}^{t_r} I^2(t)dt \int_{t_l}^{t_r} V^2(t)dt\right\}} \quad (45)$$

where I(t) and V(t) are denoting the input signal and the main mode of the reconstructed signal, respectively. $t_r$ and $t_l$ are the starting and ending points of the main mode [FIG. 9]. As shown in FIG. 9, $t_r$ and $t_l$ are time durations equivalent to three periods of the input signal from the main mode. Note that TI is independent of scaling of one signal with respect to the other. It is only a measure of closeness in terms of the shape.

Next, the symmetry index (SI) is proposed to measure the symmetry of the main mode in the reconstructed signal:

$$SI = 1 - \sqrt{\int_{t_0}^{t_r} \{R(t)L(-t)\}^2 dt} \bigg/ \sqrt{\int_{t_0}^{t_r} R^2(t)dt \int_{t_l}^{t_0} L^2(t)dt} \quad (46a)$$

where R(t) and L(t) are the right and left sides of the reconstructed signal with respect to the main peak at to as shown in FIG. 9. If the reconstructed signal is symmetric, SI becomes zero. As the difference between the right side and the left side of the reconstructed signal increases, SI approaches to one. It can be shown that when a symmetric input signal is applied, the reconstructed signal should be also symmetric. Therefore, the time reversibility along a wave path can be determined by checking the SI of the reconstructed signal. Hereinbelow, the time reversibility of each experiment is evaluated using TI and SI.

Extension of Time reversal acoustics to Lamb waves has a great potential in developing Lamb wave based damage detection methods because it can compensate the dispersive characteristics of Lamb waves and alleviate the difficulties of wave interpretation for damage assessment. Theoretical investigation was presented to better understand and implement the time reversibility of Lamb waves. The effects of Lamb wave velocity dispersion and amplitude dispersion characteristics, and wave reflections from boundaries on the TRP were fully investigated through mathematical formulation.

First, it was shown that the frequency dependancy of the time reversal operator associated with amplitude dispersion of Lamb waves deterred the full reconstruction of broadband input signals. In this respect, the use of narrowband input signal was justified to minimize the amplitude dispersion for full reconstruction of input signal. Second, the main mode of the original input signal was shown to appear in the reconstructed input signal due to compensation of within-mode dispersion via the TRP. Third, both the main mode and the side bands of the original input signal was proved to appear in the reconstructed input signal due to compensation of multi-mode dispersion and reflection from boundaries during the TRP. Here, it should be noted that the symmetry of the reconstructed signal is preserved at the presence of multiple symmetric and anti-symmetric modes and asymmetry of a structure's boundary conditions. Finally, the sensor effect on the TRP is examined for practical consideration and the time reversal related indices were introduced to quantify the degree of time reversibility.

Figure 10:
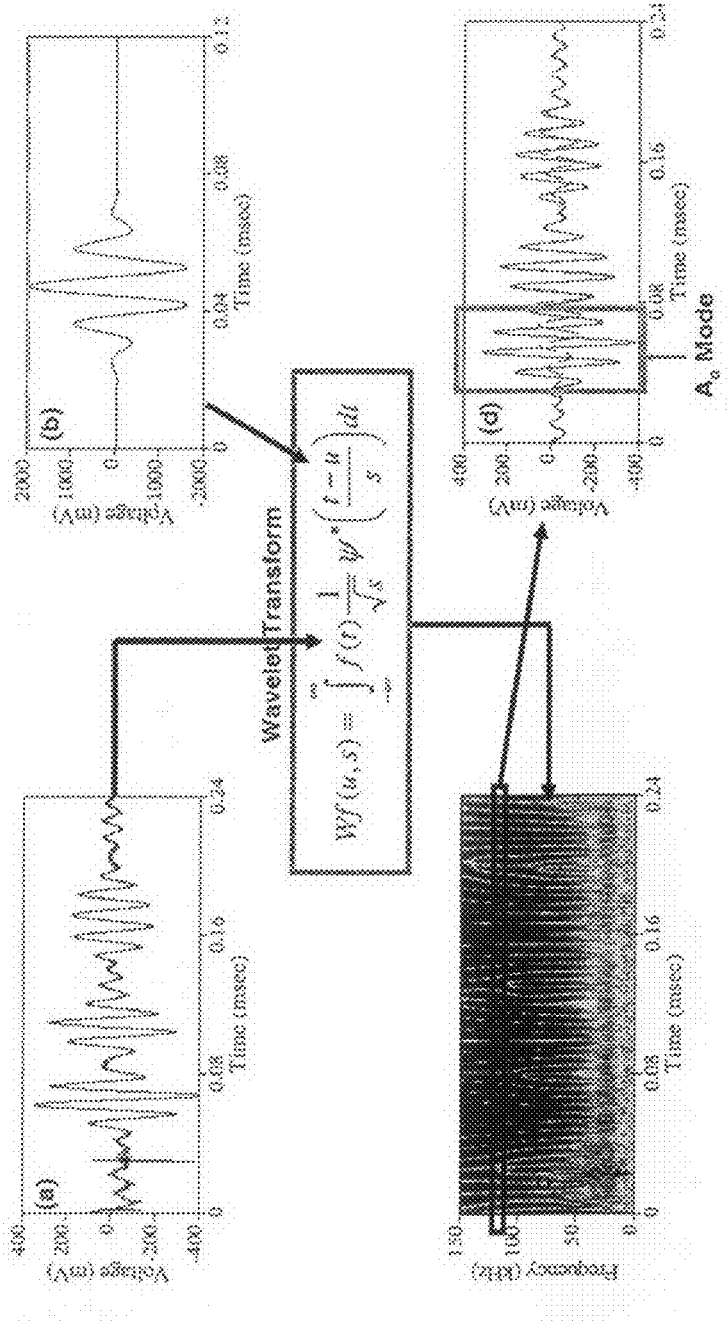

Based on the understanding of the time reversal process described above, one embodiment of the actual damage detection is preformed in the following manner: a) generating and tuning a narrowband toneburst signal, and applying the signal to the first PZT; b) receiving the signal at the second PZT; c) truncating the recorded time signal; c) receiving the transmitted guided waves at the second PZT; d) using a time reversal process to transmit a 'mirror image' of the received guided waves from the second PZT back to the first PZT; e) performing additional signal processing; f) denoising using wavelet analysis; g) computing multiple damage indices; h) applying damage identification algorithms; h-1) performing sequential outlier analysis; h-2) performing cluster analysis; and i) applying damage classification algorithms; j) identifying the location of damage. These steps will be described in more detail hereinbelow.

a) Generating, tuning, and applying. The process begins by generating and tuning a narrowband toneburst signal with the arbitrary signal generator. Thereafter, the signal is applied to the first PZT, transmitted through the structure.

b) Receiving. The transmitted guided wave signals are received at the second PZT and a response is measured at the second PZT.

c) Truncating. The recorded time signal is truncated in a manner so as to negate the effects of boundary reflections of the Lamb waves and multimodes so as to enhance the time reversibility of the Lamb waves.

d) Using a time reversal process. The time reversal process is used to transmit a 'mirror image' of the received guided waves from the second PZT back to the first PZT.

e) Performing additional signal processing. This additional signal processing is performed during the initial forwarding and the time reversal processes and is used to improve the time reversibility of Lamb waves. These include, for example, (1) applications of band-limited filtering, (2) proper scaling of the time reversed and the final reconstructed signals, (3) denoising using wavelet analysis.

f) Denoising using wavelet analysis. The denoising using wavelet analysis is unique in a sense that the basis function of the wavelet analysis is chosen to be identical to the original input signal. The basic concept of this denoising is as follows: If the signal shape that needs to be extracted for damage detection is known a priori, optimal extraction can be achieved using a matched mother wavelet that models the shape of the response signal component. The automated selection procedure is schematically shown in FIG. 10. First, the continuous wavelet transform of the signal, Wf(u,s), is obtained by convolving the signal f(t) with the translations (u) and dilations (s) of the mother wavelet:

$$Wf(u, s) = \int_{-\infty}^{\infty} f(t) \frac{1}{\sqrt{s}} \Psi_{u,s}^*(t) dt \qquad (46b)$$

where $$\Psi_{u,s}^*(t) = \frac{1}{\sqrt{s}} \Psi\left(\frac{t-u}{s}\right) \qquad (46c)$$

The Morlet wavelet, which is the same as the previously defined input signal, is used as a mother wavelet $\Psi(t)$ for wavelet transform. Then a complete set of daughter wavelets $\Psi^*_{u,s}(t)$ is generated from the mother wavelet by the dilation (s) and shift (u) operations. Note that each value of the wavelet coefficient Wf(u,s) is normalized by the factor $1/\sqrt{s}$ to ensure that the integral energy given by each wavelet is independent of the dilation s.

Because the Morlet wavelet is used as a mother wavelet for wavelet transform and the wavelet coefficient is the correlation between the signal and the mother wavelet by definition, the wavelet coefficient arrives at its maximum value when the shape of the response signal becomes closest to that of the Morlet wavelet. When this search of the maximum wavelet coefficient is performed at the input frequency, the Lamb wave modes can be easily detected by the temporal shift parameter u. Hence, this wavelet transform can be an effective way to reduce noise if the mother wavelet is chosen to be a good representation of the Lamb waves to be detected.

As described previously, the driving frequency of the narrowband excitation can be selected so that only two fundamental modes are generated for wave propagation. Then, different wave speeds of these two modes are compensated during the time reversal process when they are reversed in a time domain before being retransmitted. However, the frequency content of the traveling waves smears into nearby frequencies and is non-uniformly amplified during the time reversal process. Therefore, to enhance the time reversibility of the reconstructed signal at the original input point, the measured response signal needs to be processed before reemitting at the response point. In particular, for the time reversal analysis of Lamb waves, it is critical to retain the response components only at the original input frequency value, because of the frequency dependent nature of the time reversal operator. To achieve this goal, a multi-resolution analysis is adopted to filter out the measurement noise in response signals and to keep only the response component at the driving frequency value. Once the wavelet coefficients are computed from Eq. (46b), the original signal can be reconstructed via the following inverse continuous wavelet transform:

$$f(t) = \frac{1}{C_\varphi} \int_{-\infty}^{\infty} \int_0^\infty Wf(u,s) \frac{1}{\sqrt{s}} \psi\left(\frac{t-u}{s}\right) \frac{1}{s^2} ds\, du \qquad (46d)$$

where $C_\varphi$ is a constant determined by $$C_\psi = \int_0^\infty \frac{|\psi|}{\omega} d\omega \qquad (46e)$$

In this invention, the integration operation with respect to the scale parameter s in Eq. 46(d) is restricted only to near the driving frequency in order to filter out frequency components outside the driving frequency before transmitting the response signal back to the original input location:

$$f(t) = \frac{1}{C_\varphi} \int_{-\infty}^{\infty} \int_a^b Wf(u,s) \frac{1}{\sqrt{s}} \psi\left(\frac{t-u}{s}\right) \frac{1}{s^2} ds\, du \qquad (46f)$$

where a and b are the lower and upper limits of the narrowband excitation frequency. The choice of the frequency limits is dictated by the fact that the filter must cover the frequency range of interest so that useful information is not lost. In fact, the wavelet transform is used as a matched filter to improve the signal-to-noise ratio without any loss in time resolution or accuracy and in many cases with improvements. This filtering processing is repeated for the reconstructed input signal obtained by the time reversal process. This filtering process tends to minimize the measurement noise in the response signal and keep the response-component only at the driving frequency. It is observed that this filtering process improves the time reversibility of Lamb waves.

g) Computing multiple damage indices. This may include, for example, computing multiple damage indices such as time reversal and symmetric indices. Note that these are only two examples of many possible different reference-free damage indices. When we use these indices, the range and scaling of the signal needs to be adjusted based on the structure's configuration, sensor layout, boundary conditions and so on.

h) Applying damage identification algorithms. This may be done to determine the existence of defects without using any previously established threshold values. There may be many different reference-free classification algorithms including sequential outlier analysis and cluster analysis.

h-1) Performing sequential outlier analysis. The objective of outlier analysis is to identify a new pattern that differs from previously obtained patterns in some significant respect. For this invention, this concept of outlier analysis is extended so that the outlier analysis can be performed without using previously established threshold values.

One example of outlier analysis according to the present invention is as follows. First, the damage index values are instantaneously computed from a questionable state of a structure. Second, the damage index values from all the paths are sorted in an ascending order. Third, the largest damage index value is tested for discordance against the remaining damage index values. This last step is repeated for the second largest outlier, the third and so on until all outliers are identified or a predetermined number of damage index values are tested for discordance. It should be noted that each damage index value is tested for discordance with respect to the other simultaneously obtained damage index values rather than with respect to those obtained from the baseline condition of the structure. Therefore, the damage index values corresponding to the damaged paths have been identified without referencing to the baseline damage index values. In this way, the dependence on baseline data has been removed both in the feature extraction procedure (using the time reversal process) and in the decision-making procedure (using consecutive outlier analysis).

Hereafter, details of the outlier analysis will be described. First, consecutive outlier analysis is formulated for exponential samples. Then, data transformation is introduced so that consecutive outlier analysis can be used for the general extreme value (GEV) distributions. An exponential distribution with a scale parameter b and an origin at a has the following probability density distribution:

$$\psi(x) = \begin{cases} \frac{1}{b}\exp[-(x-a)/b] & \text{for } x > a \\ 0 & \text{for } x < a \end{cases} \qquad (46g)$$

There are a wide range of discordant (outlier) tests that can be used with exponential data. In this invention, one of the most common tests is presented for demonstration rather than exhaustively comparing different types of available tests. A test statistic for the smallest potential outlier is defined as:

$$T = Y_1/\Sigma Y_i \qquad (46h)$$

where samples $Y_1, Y_2, \ldots, Y_n$ are sorted in an ascending order, and n is the size of the samples. Some outlier analysis tests for exponential samples require the origin of the distribution to be at zero. For example, the outlier analysis based on the statistic $Y_1/\Sigma Y_i$ assumes that the origin is zero. When the exponential samples have a non-zero origin a, then a new statistic $(Y_1-a)/(\Sigma Y-na)$ can be used. However, in most tests, the scale parameter b is assumed unknown. Then, it can be shown that this test statistic has a probability density function $\Psi_n(t)$:

$$\psi_n(t) = \begin{cases} n(n-1)(1-nt)^{n-1} & \text{for } 0 \le t \le \frac{1}{n} \\ 0 & \text{for } t \ge \frac{1}{n} \end{cases} \qquad (46i)$$

and has a recurrence relationship with the cumulative density function $\Psi_{n-1}(t)$:

$$\Psi_n(t) = nb(t)_{1,(n-1)}(1-\Psi_{n-1}[t/(1-t)]) \qquad (46j)$$

where $b(t)_{r,s}$ is a beta density function with parameters r and s and defined as $[B(r,s)]^{-1}t^{r-1}(1-t)^{s-1}$, and $B(r,s)$ is a binomial distribution with parameters r and s.

Finally, the significance probability associated with an observed value t of a discordance statistic T is denoted by SP(t):

$$SP(t) < nF_{2,2(n-1)}[(n-1)t/(1-t)] \qquad (46k)$$

where $F_{v,u}[x]$ is a F-cumulative distribution function with v and u degrees of freedom. SP(t) is the probability that T takes values more discordant than t. In other words, SP(t) is the probability that there will be other smaller outliers more discordant than t. That means when the SP(t) is small for an observed value of t, the smallest value $X_1$ associated with t is most likely an outlier. Therefore, we define an outlier probability OP(t) as:

$$OP(t) > 1 - nF_{2,2(n-1)}[(n-1)t/(1-t)] \quad (46l)$$

This outlier analysis is consecutively conducted starting from the smallest value to the second smallest value, the third and so on until all outliers are identified or the maximum number of samples specified by a user is reached.

If X is a sample from the GEV for maxima, then the following transformed sample Y has an exponential distribution with origin 0 and mean 1:

$$Y = \left[1 + \gamma\left(\frac{x-\mu}{\sigma}\right)\right]^{-1/\gamma} \quad (46m)$$

As γ approaches zero, the GEV for maxima converges to the Gumbel distribution for maxima and the above transformation is simplified as follows:

$$Y = \exp[-(x-\mu)/\sigma] \quad (46n)$$

The largest value $X_n$ in the original sample of the GEV for maxima is converted to the smallest value $Y_1$ in the transformed sample. Therefore, the test on the Y values must be chosen accordingly. This is why the consecutive outlier test is initially formulated for the minimum value of the exponential distribution in the previous section. Once extreme value samples are transformed to exponential samples, the rest of consecutive outlier analysis is identical to that of the exponential samples.

Note that for the outlier test of a sample $X_i$, the best-fit GEV and the associated σ, μ, and γ parameters need to be estimated for the remaining data set $\{X_1, X_2, \ldots, X_{i-1}\}$. In addition, the procedure is repeated in a consecutive manner for i=n, n–1, ..., n–k. Here, k is the maximum number of possible outliers that will be tested for discordance. Because the best-fit GEV and the associated parameters need to be sequentially estimated multiple times, an automated procedure for parameter estimation of the GEV has been developed in this invention as well.

h-2) Performing cluster analysis. The sequential outlier analysis described above is more suitable when only a few outliers are expected while clustering analysis is better suited when equally populated data are expected from different classes.

Cluster analysis seeks to divide a set of data (damage sensitive features) into several classes (undamaged or damaged conditions in the current application) so that data samples more similar to one another than they are to those in a different group can be grouped together. Cluster analysis is one particular case of unsupervised learning because the algorithm automatically classifies each sample based only on the distance measure provided. That is, the algorithm does not need any supervised learning with prior training data sets, and it is solely based on the current data set fed to the algorithm. Some of the algorithms that can be used for clustering include k-means, Gaussian mixture models, hierarchical clustering, self-organized mapping, subspace clustering, density-based algorithms, and graphic-based algorithms. The differences among these clustering techniques are how the distance between data samples is computed and how a data point is assigned to a specific cluster. For instance, k-means clustering uses the Euclidean distance as the underlying distance measure and assigns a data point into the cluster that has the shortest distance from its centroid. In this claim, this k-means cluster analysis is adopted for demonstration purposes. It is possible that this reference-free damage classification be accomplished using different clustering techniques.

K-means clustering is an algorithm that classifies data sets into k number of groups based on their attributes or features. This grouping is performed by minimizing the Euclidian distance of each data point from the centroid of the corresponding group. Basically, the following three steps are iterated until no further change in clustering appears. To assist the understanding of the k-means clustering, a simple numerical example is provided here (Teknomo, K. (2005). *K-Mean Clustering Tutorials*. Retrieved Jul. 25, 2006, from http://people.revoledu.com/kardi/tutorial/kMean/index.html).

Suppose there are four data points and each data point has two attributes/features as shown in Table 1. The objective of the k-means clustering is to group these data points into k=2 groups based on these features. For instance, it can be assumed that each data point has the TR and SYM indices as its features, and the goal is to assign them either to "undamaged" and "damaged" classes.

Step 1—Estimation of class centroids: For a given number of k classes, the centroid of each class is arbitrarily assumed at the beginning. Often a subset of the available data points is designated as the centroids. Note that the final clustering is affected by this initial estimate of the centroids. Therefore, multiple iterations are repeated with different initial centroid positions. Suppose samples A and B are used as the initial centroids, and let C1 and C2 denote the coordinate of the centroids. Then, C1=[0.1, 0.1] and C2=[0.2, 0.1].

Step 2—Estimation of distance measures: Next, the Euclidean distance from the cluster centroids to each sample point is computed as shown in Table 2. For instance, the Euclidean distance from the Cluster 1 centroid to Sample C is $\sqrt{(0.4-0.1)^2 + (0.3-0.1)^2} = 0.361$.

Step 3—Cluster Assignment: Each sample is assigned to a cluster based on the minimum distance. For instance, Sample A is assigned to Cluster 1, and the rest are assigned to Cluster 2 as shown in Table 3. The ultimate goal is to minimize the sum of sample-to-centroid distances over all clusters. This is achieved in two steps. In the first step, all samples are assigned to their nearest cluster centroid all at once, and the cluster centroids are reevaluated for the next step. Then, more subtle tuning is performed by reassigning an individual sample to the other cluster. If this reassignment reduces the total sum of the distances, then the affected cluster centroid is recomputed after each reassignment. The new centroid for each cluster is assumed to be the average value of all sample data points assigned to the specific cluster. For instance, the new centroids for the next iteration become C1=[0.1, 0.1] and C2=[(0.2+0.4+0.5)/3, (0.1+0.3+0.44)/3] for the example presented in Table 3. The second step passes through all the samples for this reassignment. This iteration is repeated until its stability, meaning that switching of any additional sampling points does not minimize the sum of each cluster's Euclidean distances, is reached.

TABLE 1

An example data set for k-means clustering

|  | Sample A | Sample B | Sample C | Sample D |
|---|---|---|---|---|
| Feature 1 | 0.1 | 0.2 | 0.4 | 0.5 |
| Feature 2 | 0.1 | 0.1 | 0.3 | 0.4 |

TABLE 2

Euclidean distance of sample points from each cluster centroid

| | Sample A | Sample B | Sample C | Sample D |
|---|---|---|---|---|
| Cluster 1 | 0.000 | 0.100 | 0.361 | 0.500 |
| Cluster 2 | 0.100 | 0.000 | 0.283 | 0.424 |

TABLE 3

Clustering of sampling points based on k-means algorithm

Figure 11:
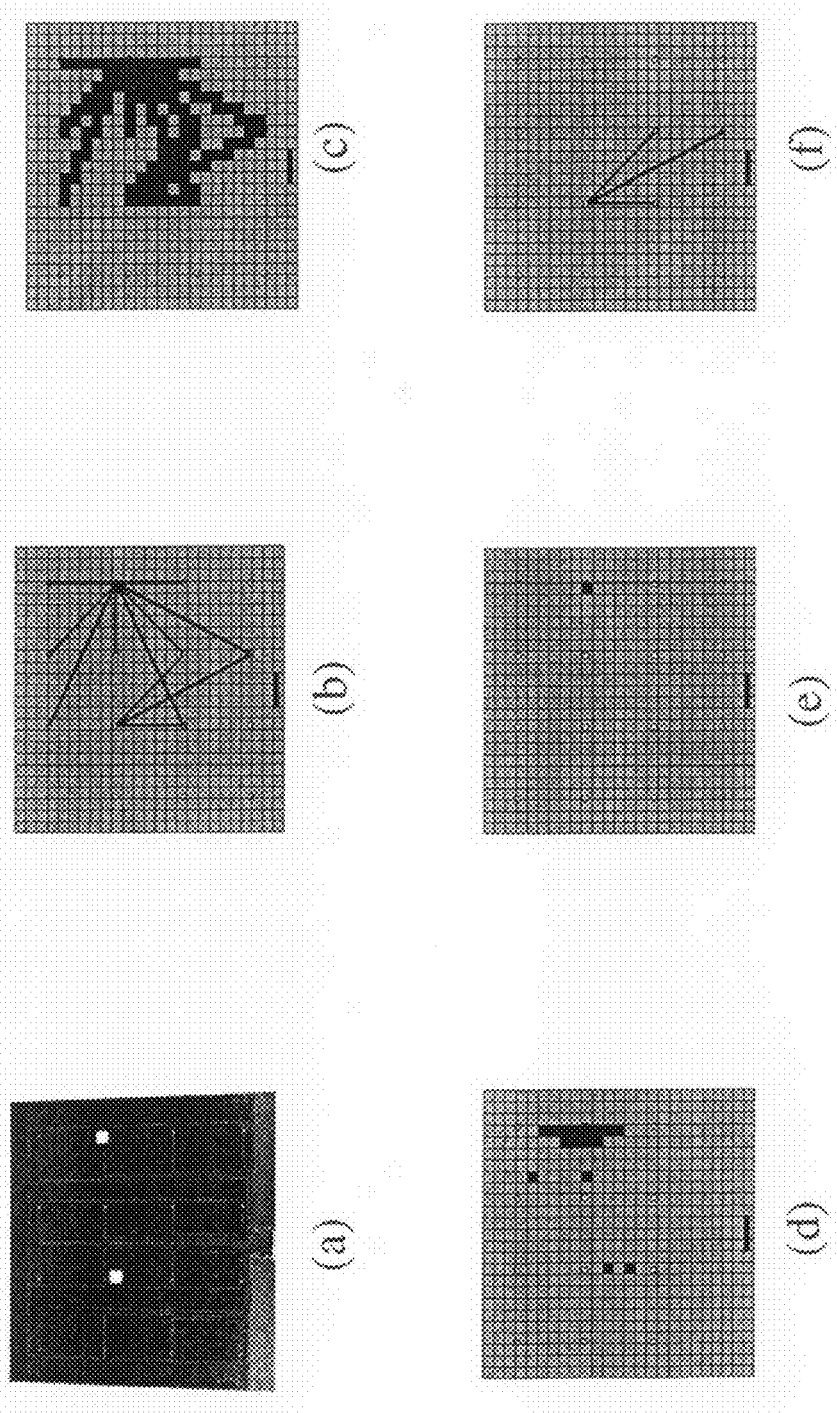

| | Sample A | Sample B | Sample C | Sample D |
|---|---|---|---|---|
| Cluster 1 | Assigned | | | |
| Cluster 2 | | Assigned | Assigned | Assigned | i) Applying damage classification algorithms. The damage classification algorithms are used to identify different types of detects. For instance, a nonlinear damage such as delamination changes the time reversal and symmetric indices. On the other hand, notch and corrosion damage create mode conversions and create additional sidebands in the reconstructed signal.

j) Identifying the location and area of damage using damage localization algorithms. To identify the location and area of the defect, the test specimen in FIG. 11(*a*) is divided into 25-by-25 virtual grids as shown in FIG. 11(*b*). The size of each grid is 2.44 cm×2.44 cm (0.96 in×0.96 in). The defect shown in FIG. 11(*a*) can be identified from the damaged paths previously detected in FIG. 11(*b*) based on the following rules:

(1) All boxes that are crossing the damage paths at least once are identified [FIG. 11(*c*)].

(2) Any boxes crossing the undamaged paths, identified from the previous reference-free damage classification algorithms, are excluded from possible damage locations [FIG. 11(*d*)].

(3) The box that has the largest number of the damaged paths crossing and zero number of the undamaged paths crossing is selected as the first possible damage location [FIG. 11(*e*)].

(4) If there are any damaged paths left that are not crossing the damaged box(es) selected in the previous step, find a subset of the boxes that is crossing these remaining damaged paths and repeat steps (1)-(4) until there are no damaged paths left that are not crossing the selected boxes at least once [FIG. 11(*f*)].

Note that this last step (4) is necessary to detect multiple damage locations. In addition, a damage area larger than one virtual grid size will be indicated by multiple boxes.

Hereinbelow, numerical simulation and experimental studies are described to validate the theoretical findings and to illustrate the effects of the size difference and bonding condition of the PZT sensors and defects on the TRP.

Figure 14:
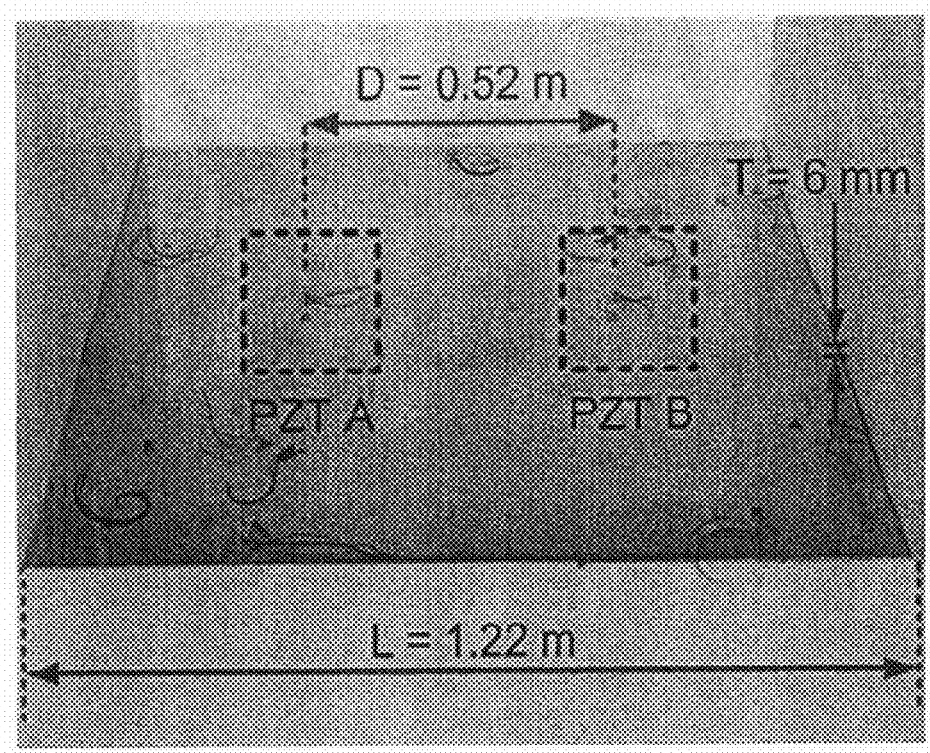
FIGS. 14 and 15 illustrate an aluminum plate specimen and an aluminum bar specimen, respectively, used in test bed according to the present invention.

The present invention will now be described in terms of experiments conducted according to the present invention and in terms of the corresponding experimental results. To examine various characteristics of the TRP, two different types of test specimens are employed in this study. The first specimen shown in FIG. 14 is a 122 cm×122 cm×0.6 cm aluminum plate with two PZT patches mounted in the middle. The PZTs are placed in the middle so that direct signals can be clearly separated from reflected signals due to plate boundaries, and the two PZTs are 0.52 m apart each other. For the second specimen shown in FIG. 15, an aluminum beam (199 cm×5.08 cm×0.6 cm) is instrumented with two PZT wafer transducers. To avoid the effect of multimodes in Lamb wave propagation, the size of each PZT transducer and the driving frequency are determined for generating only $S_0$ and $A_0$ modes. The size of the PZTs is 1 cm×1 cm in an aluminum bar, and various sizes of PZTs are mounted on the aluminum plate for checking the effect of PZT size on reciprocity and time reversibility in Lamb wave propagation. In both experiments, a PSI-5A4E type of PZT sheet (thickness=0.0508 cm) is cut to various sizes and attached to the substrate with commercial cyanoacrylate adhesive.

Figure 12:
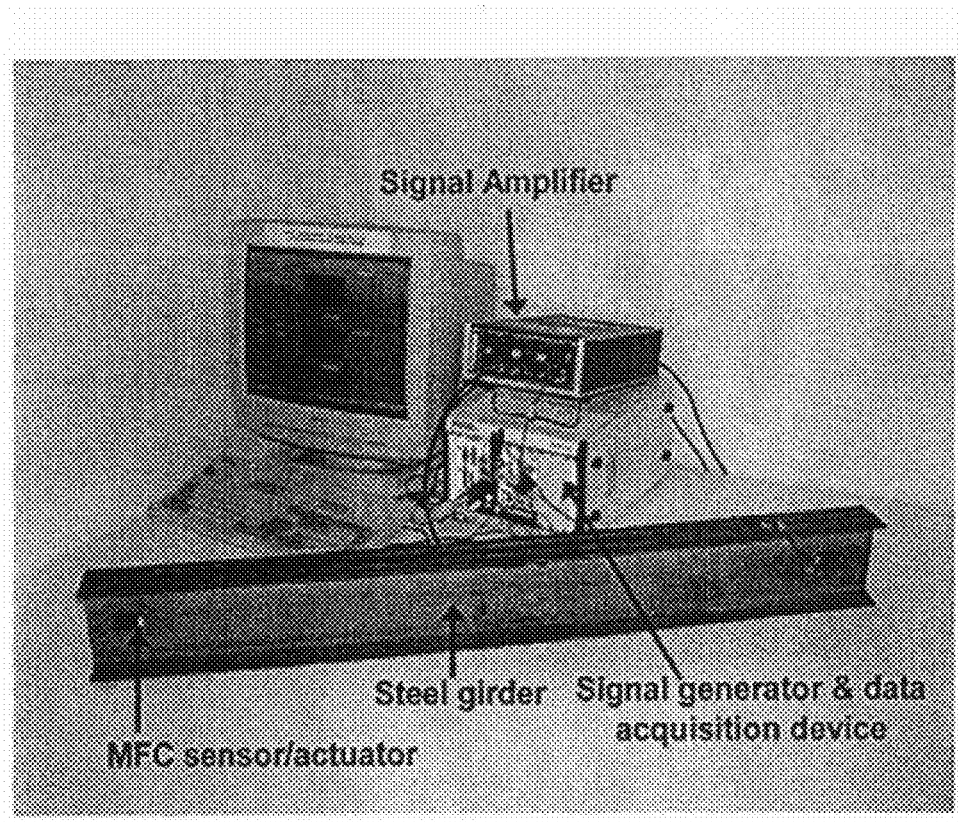
FIGS. 12 and 13 illustrate an image and a block diagram, respectively, of a testing configuration for reciprocity and time reversibility in Lamb wave propagation.
Figure 13:
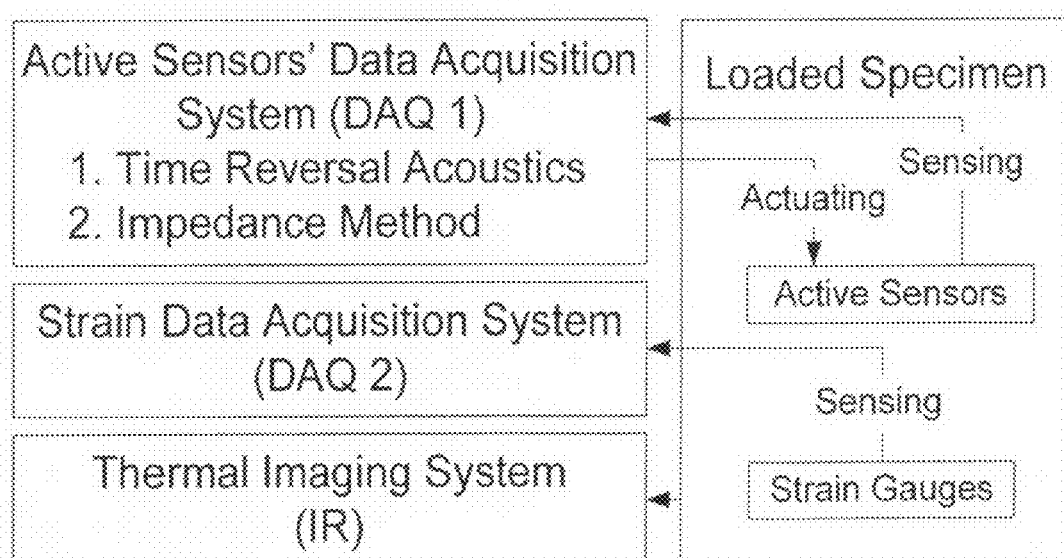

The overall configuration of the data acquisition system used for this experimental study is shown in FIGS. 12 and 13. The data acquisition system consists of an arbitrary waveform generator (AWG), a high-speed signal digitizer (DIG), two multiplexers, and a low noise preamplifier (LNP). An AWG is one of electronic devices used to generate electrical waveforms. Unlike ordinary function generators, AWGs can create any arbitrary defined waveform as their output. A DIG measures analog voltage signal and turns the signal into digital signal. A LNP magnifies the amplitude of a signal and filters the signal using its built-in analog filters. Therefore, a signal whose signal to noise ratio is relatively low can be conditioned using the LNP.

A narrowband toneburst signal is generated using the AWG, and the signal amplitude is scaled so that the peak-to-peak voltage is 20 V. The exciting frequency is varied from 90 kHz to 150 kHz. First, the input waveform is applied to PZT A. PZT A generates elastic waves, and the corresponding response is measured at PZT B. When the waves arrive at PZT B, the output from PZT B is amplified by the LNP and measured by DIG with 16 bits resolution. Once the response is recorded, the signal is reversed in the time domain and applied back to PZT B after proper scaling. Finally, the corresponding response is measured at PZT A and compared with the original toneburst input signal.

In the following section, reciprocity in Lamb wave propagation and time reversibility are demonstrated using recorded signal at the PZT B and finally reconstructed signal at the PZT A, respectively.

Demonstration of Reciprocity and Time Reversibility

The starting point for the time reversibility is the following reciprocity of elastodynamic system:

$$\int_S (\hat{t}_{II} \cdot \hat{u}_I - \hat{t}_I \cdot \hat{u}_{II}) dS = 0 \quad (47)$$

Eq. (47) indicates that the work done by traction force $\hat{t}_I$ on displacements $\hat{u}_{II}$ is equal to the work done by traction force $\hat{t}_{II}$ on displacements $\hat{u}_I$. Note that $\hat{u}_I$ and $\hat{u}_{II}$ are displacements produced by $\hat{t}_I$ and $\hat{t}_{II}$, respectively. This reciprocity can be viewed as an extension of the Betti's reciprocal relation to elastodynamics.

Figure 16:
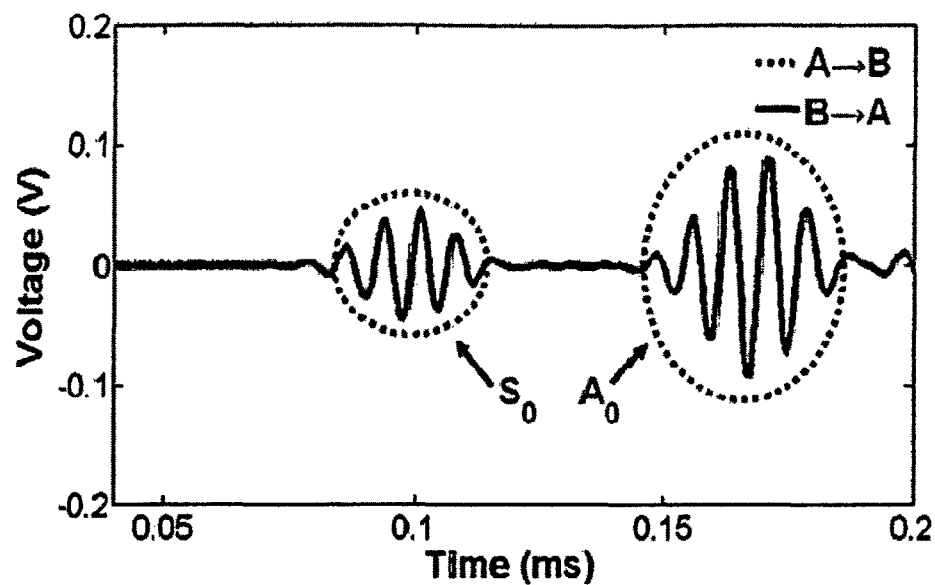

In the current example, this reciprocity is translated such that signal AB is identical to signal BA. Here, signal AB is the response signal measured at PZT B when the input signal is applied to PZT A. Signal BA is defined in a similar manner when the identical input signal is applied to PZT B. This reciprocity is demonstrated using a pair of PZT patches attached to the aluminum plate shown in FIG. 14. Here, two rectangular PZTs with the same size (1.0 cm×1.0 cm) are attached to locations A and B, and it is assumed that the variations in the PZT size and bonding condition are negligible. The effects of the PZT size and bonding conditions are further examined hereinbelow. The exciting frequency of the narrowband toneburst signal, the number of time-averaging, and the LNP gain were set to 130 kHz, 20 times, and 10, respectively. The forwarding signal AB or BA was truncated at 1 ms before it was reversed and resent to the original location. FIG. 16 shows that signals AB and BA are almost identical.

Figure 17:
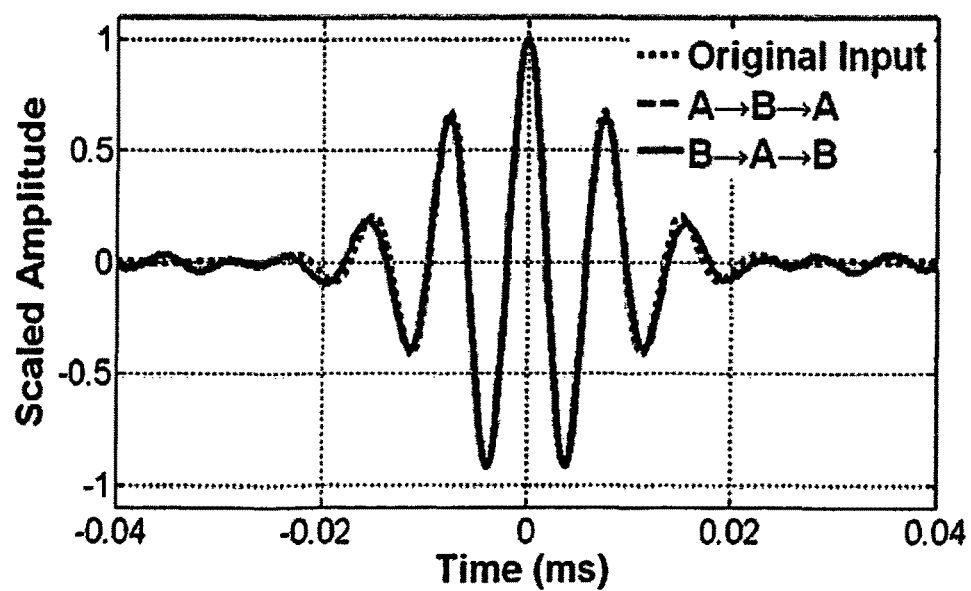

Next, the time reversibility is examined for two different wave propagation paths: A→B→A and B→A→B. The shapes of the main modes from both paths are shown almost identical to that of the original input [FIG. 17]. This experiment demonstrates that the shape of the original input signal is successfully restored at the main mode in the reconstructed signal through the TRP. Note that only the main mode is shown in this figure. Additional side-bands are created by multi-modes and reflections, and their effects are investigated later. The deviation of the reconstructed signal from the original input signal can be quantified using the time reversal index (TI) and symmetric index (SI). The results in Table 4 show that the TRP is successfully conducted for the two different wave paths. Later, the effects of the multimodes and reflections will be discussed.

TABLE 4

TI and SI values for signal paths A → B → A and B → A → B

| Path | TI | SI |
|---|---|---|
| A → B → A | 0.00350117 | 0.999843 |
| B → A → B | 0.00351698 | 0.999764 |

The Frequency Dependency of the TRP

It has been shown that the reconstructed signal, $V_R$, is related to the original input signal, $V_A$ as follows;

$$V_R = k_s G k_a V_B^* = k_s G k_a k_s^* G^* k_a^* V_A^* = \Gamma K K^* V_A^* \quad (48)$$

where $K = k_s k_a$, and $\Gamma$ is the time reversal operator defined as $\Gamma = GG^*$. Eq. (48) indicates that the reconstructed signal, $V_R$, is a "time reversed" and "scaled" version of the original input signal $V_A$ if the time reversal operator and the mechanical-electro coefficients are constant over the frequency range of interest. However, the time operator is frequency dependent for Lamb waves. Because of the amplitude dispersion of Lamb waves, the time reversal operator varies with respect to frequency, and wave components at different frequency values are non-uniformly amplified during the TRP. Due to this amplitude dispersion of the TRP, the original input signal cannot be properly reconstructed if the input signal consists of multiple frequency components such as a broadband input signal.

Figure 18:
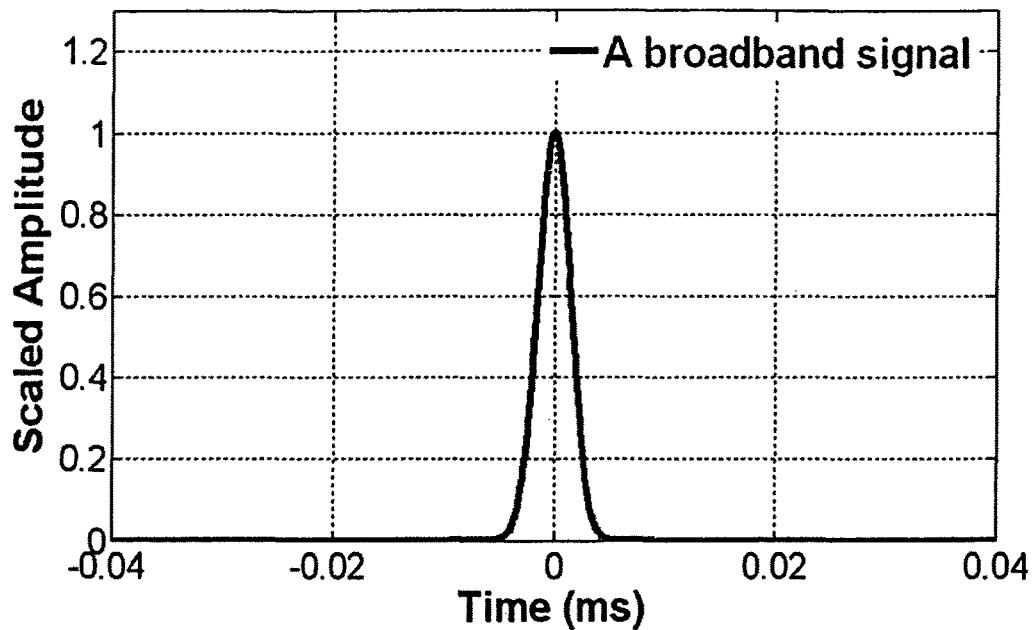
Figure 19:
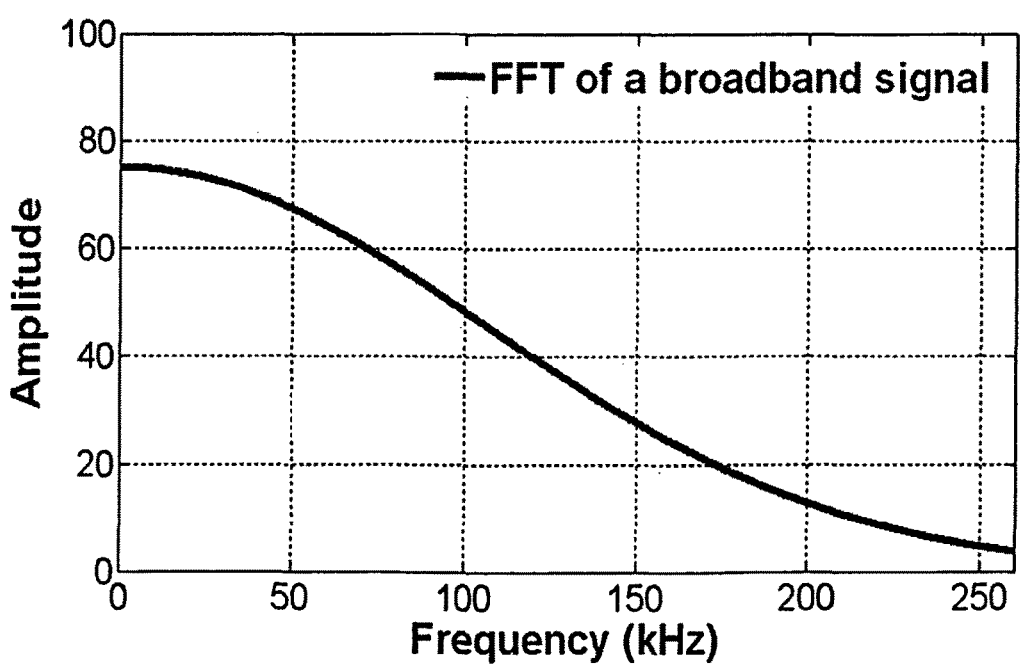
Figure 20:
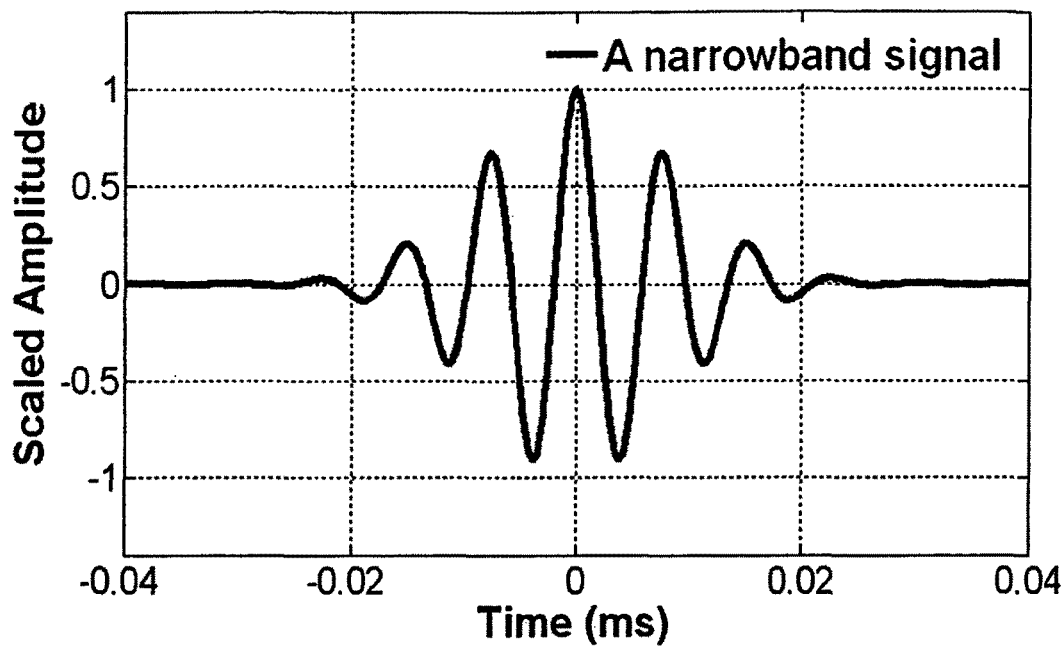
Figure 21:
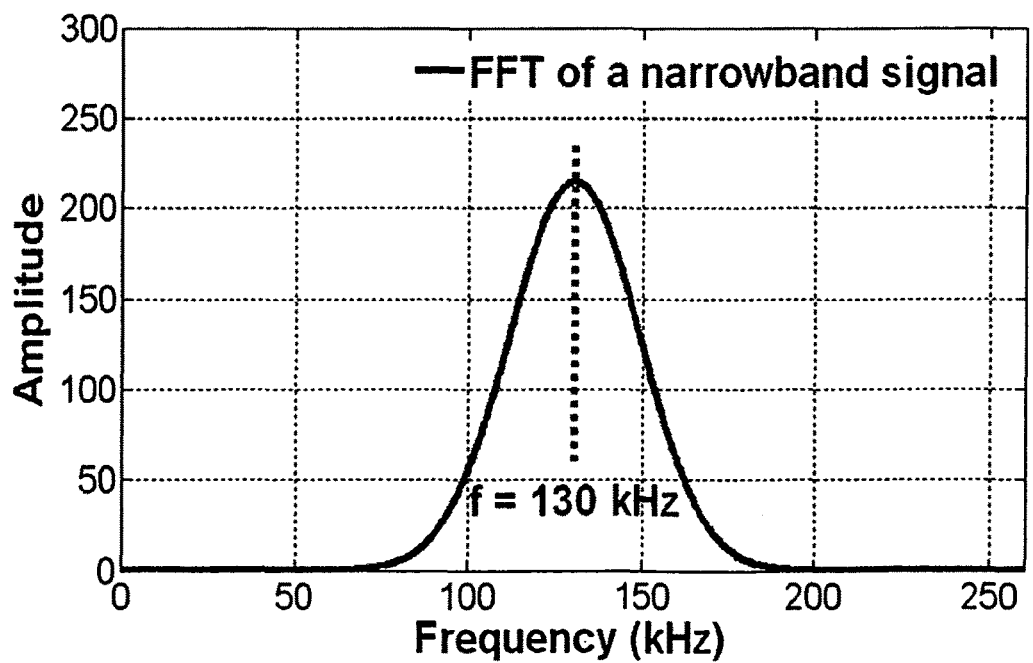

In this section, the frequency dependency of the TRP is experimentally investigated by using two different types of input signals; a broadband Gaussian impulse shown in FIG. 18 and a narrowband toneburst signals shown in FIG. 20. Using these two different input waveforms, the TRP described in the previous section was repeated. The other test configurations were identical to those described hereinabove except for the distance between two PZTs (40 cm). FIGS. 19 and 21 illustrate FFT of the signals in FIGS. 18 and 20, respectively.

Figure 22:
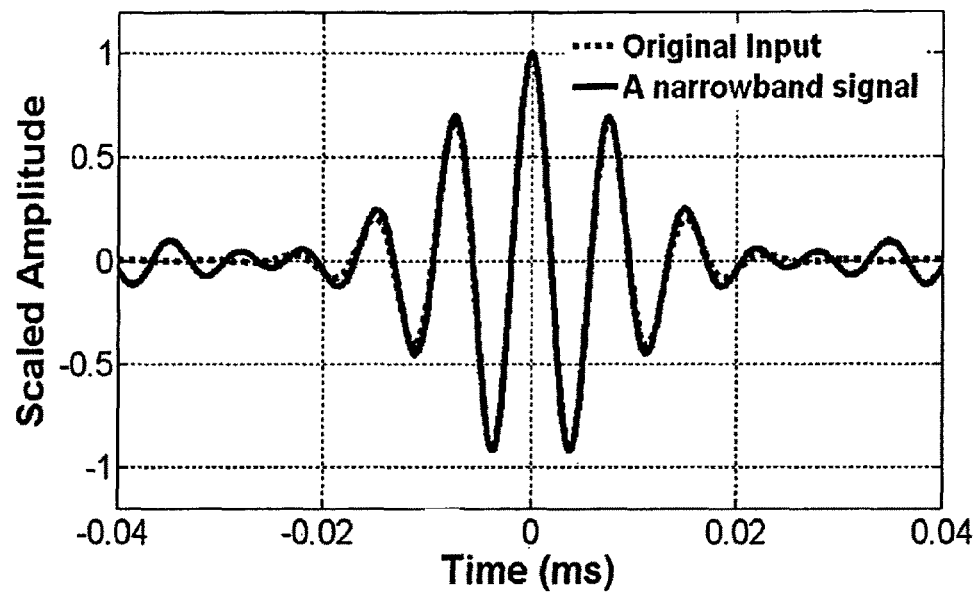
Figure 23:
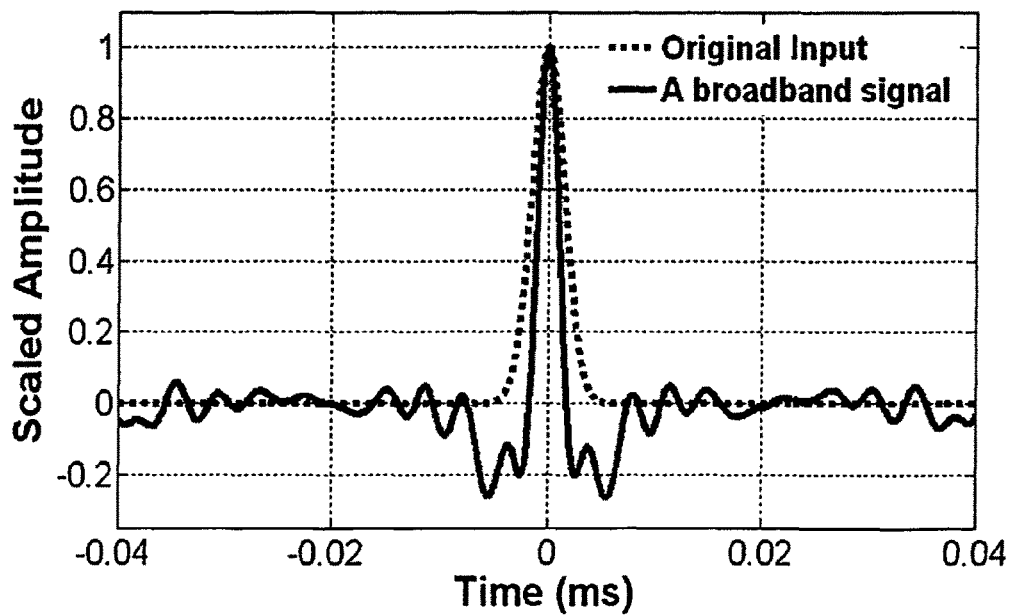

FIGS. 22 and 23 illustrate the reconstructed signals when these input waveforms were used for the TRP. As shown in FIG. 22, the shape of the reconstructed signal significantly deviated from the shape of the original impulse when the broadband signal was used. However, it can be seen that the energy refocusing was successfully accomplished, and the symmetricity of the reconstructed signal was preserved. When the narrowband excitation was used in FIG. 23, the shape of the original input signal was successfully restored. A more quantitative comparison between the reconstructed signals and the input signals is provided in Table 5. Although the TI value significantly increased, the SI value remained close to zero when the broadband excitation was employed. It has been shown that this symmetry of the reconstructed signal is valid regardless the frequency content of the input signal as long as its shape is symmetric. For the narrowband excitation, both TI and SI values stayed near zero.

This section demonstrates that the use of a narrowband input signal can minimize the frequency dependency of the TRP and enhance the time reversibility of Lamb waves. However, the shape of the reconstructed signal is still not identical to that of the original input signal due to the multimode dispersion and reflections from the structure's boundaries. Their effects on the TRP are experimentally investigated in the next section.

Table 5 Illustrates the TI and SI Indices in Different Input Signal Cases

| | TI | SI |
|---|---|---|
| Signal type | | |
| Narrowband | 0.00224322 | 0.000351 |
| Input signal type | | |
| Broadband | 0.2586 | 0.0008 |
| Narrowband | 0.0022 | 0.0004 |

The Effects of Multiple Modes and Reflections on the TRP
The Effect of Multiple Modes The multimodal characteristics of Lamb waves complicate the TRP. Although the use of a narrowband excitation can improve the time reversibility of Lamb waves, the reconstructed signal is still different from the original input signal due to the sidebands generated by the multiple Lamb wave modes and reflections. Here the effect of the multi modes is investigated first.

Considering this multimode effect on the TRP, the reconstructed signal will be composed of the following four mode groups:

$$V_R(t) = V_R^{SS}(t) + V_R^{AA}(t) + V_R^{SA}(t) + V_R^{AS}(t) \quad (49)$$

where $V_R^{SA}(t)$ represents the symmetric modes in the reconstructed signal generated by the anti-symmetric modes in the forward signal, and $V_R^{SS}(t)$, $V_R^{AA}(t)$, and $V_R^{AS}(t)$ are defined in a similar fashion. To simplify the experimental verification process, the driving frequency of the toneburst input signal was selected to generate only the first symmetric ($S_0$) and anti-symmetric modes ($A_0$). In this case, Eq. (29a), (29b), (30) and (31) can be combined into a single equation.

$$V_R(t) = (\overline{C}^{SS} + \overline{C}^{AA})\overline{\kappa}V_A(T-t) + \overline{C}^{SA}\overline{\kappa}V_A\{T-(t+\overline{t}^{SA})\} + \quad (50)$$

$$\overline{C}^{AS}\overline{\kappa}V_A\{T-(t+\overline{t}^{AS})\} + \frac{1}{2\pi}\overline{C}^{SA}\overline{\kappa}\int_{-\infty}^{\infty} e^{i\omega\tau^{SA}} V_A^*(\omega)e^{i\omega t}d\omega +$$

$$\frac{1}{2\pi}\overline{C}^{AS}\overline{\kappa}\int_{-\infty}^{\infty} e^{i\omega\tau^{AS}} V_A^*(\omega)e^{i\omega t}d\omega$$

Here, $(\overline{C}^{SS}+\overline{C}^{AA})\overline{\kappa}V_A(T-t)$ is the main mode created by the convergence of the $S_0$ and $A_0$ modes. $\overline{C}^{SA}\overline{\kappa}V_A\{T-(t+\overline{t}^{SA})\}$ and $\overline{C}^{AS}\overline{\kappa}V_A\{T-(t+\overline{t}^{AS})\}$ are the additional sidebands created by the coupling of the $S_0$ and $A_0$ modes. They are shifted from the main mode by $\bar{t}^{SA}$ and $\bar{t}^{AS}$, respectively. It can be shown that the arrival time of the sidebands are related to each other as follows:

$$\bar{t}^{SA} = \left[\frac{r}{w_S(\bar{\omega})} - \frac{r}{w_A(\bar{\omega})}\right] = -\bar{t}^{AS} \quad (51)$$

where, $w_S$ and $w_A$ denote the group velocity of $S_0$ and $A_0$ modes, and r and $\bar{\omega}$ represent the distance between an actuator and a sensor, and an exciting frequency, respectively. Therefore, two sidebands should be symmetric along the main mode. The remaining two terms in Eq. (50) represent the higher-order dispersive wave packets that do not converge on to the corresponding side bands of the reconstructed signal. There is no closed form solution for this integral, and this effect is not experimental verified in this experiment. Therefore, this higher-order terms are ignored in this experiment.

In this section, the existence of the sidebands due to the $S_0$ and $A_0$ mode coupling (($\overline{C}^{SA}\overline{\kappa}V_A\{T-(t+\bar{t}^{SA})\}$ and $\overline{C}^{AS}\overline{\kappa}V_A\{T-(t+\bar{t}^{AS})\}$ terms in Eq. 50)) is demonstrated. In addition, the arrival times of the sidebands are verified, and the symmetry of the reconstructed signal is shown. The test is conducted using a pair of PZT patches attached to the aluminum plate shown in FIG. 14. Here, two rectangular PZTs with the same size (1.0 cm×1.0 cm) are attached in the middle of the plates with 40 cm distance. Each PZT is 41 cm away from the boundaries. The variations in the PZT size and bonding condition are ignored in this test. The exciting frequency of the narrowband toneburst signal, the number of averaging, and the LNP gain were set to 130 kHz, 20 times, and 50, respectively.

Figure 24:
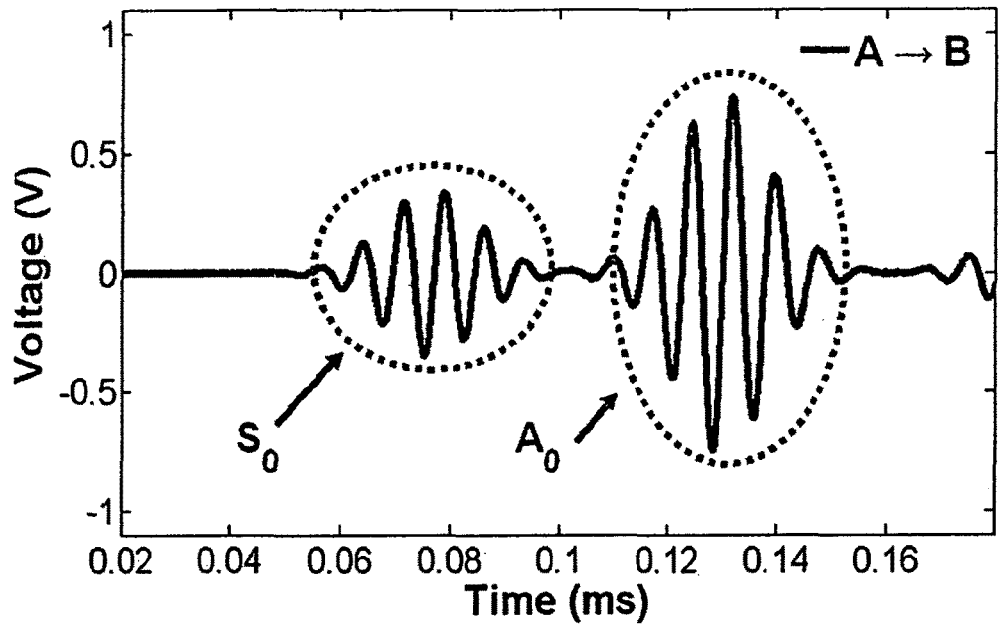

First, the forwarding signal AB in FIG. 24 was truncated at 0.105 ms so that only the $S_0$ mode can be reversed and resent to the original location during the TRP. Because only the $S_0$ mode from the forwarding signal was included in the TRP, the reconstructed signal in Eq. 50 consisted of only the following two terms.

$$V_R(t) = \overline{C}^{SS}\overline{\kappa}V_A(T-t) + \overline{C}^{SA}\overline{\kappa}V_A\{T-(t+\bar{t}^{SA})\} \quad (52)$$

Figure 25:
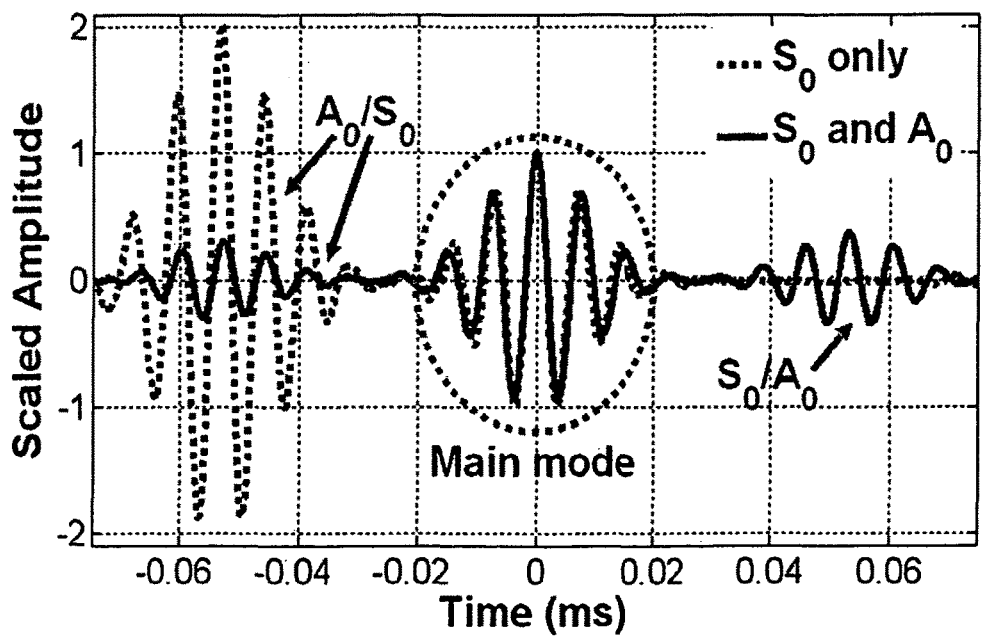

In this case, only the $S_0$ mode contributed to the main mode, and there was only one side-band as shown in FIG. 25.

Next, the TRP was repeated by truncating the forwarding signal AB at 0.160 ms so that both the $S_0$ and $A_0$ modes could be included in the TRP. In this example, the main mode were composed of the contributions from both the $S_0$ and $A_0$ modes, and two side-bands were created as shown in the following equation.

$$V_R(t) = (\overline{C}^{SS} + \overline{C}^{AA})\overline{\kappa}V_A(T-t) + \overline{C}^{SA}\overline{\kappa}_A\{T-(t+\bar{t}^{SA})\} + \overline{C}^{AS}\overline{\kappa}_A\{T-(t+\bar{t}^{AS})\} \quad (53)$$

Since $\overline{C}^{SA} = \overline{C}^{SA}$ and $\bar{t}^{SA} = -\bar{t}^{AS}$, the sidebands should be symmetric along the main mode as illustrated in FIG. 25.

Finally, the time shift value between the main mode and the side-bands were estimated from FIG. 25 and compared with the theoretical $\bar{t}^{SA}$ in Eq. 51. To compute the theoretical $\bar{t}^{SA}$ value, the group velocities of the $S_0$ and $A_0$ modes were first estimated from FIG. 22 to be 5.316 m/ms, and 3.115 m/ms, respectively. These values well correspond to the theoretical values estimated from a dispersion curve obtained from the plate properties ($V_S$=5.163 m/ms, $V_A$=3.025 m/ms). Then, the $\bar{t}_{SA}$ value was computed from Eq. (2) ($\bar{t}^{SA}$= 0.4/5.316−0.4/3.115=−0.0053 ms). This $\bar{t}_{SA}$ value agreed well with the time gap between the main mode and one of the side-bands observed from FIG. 25 (about 5.31 ms). Therefore, it is experimentally demonstrated that Eq. 53 properly described the side-bands created by multi-modes.

According to the test result, it can be inferred that the shape of the main mode in the reconstructed signal is not affected by the existence of the multiple modes, and the multiple Lamb wave modes influence the TRP by generating additional symmetric sidebands. This symmetry of the reconstructed signal is preserved as long as a symmetric input signal is used and both symmetric and anti-symmetric modes are included in the TRP. In the next section, the effect of reflections on the TRP is investigated.

The Effect of Reflections

Similar to the multiple Lamb wave modes, the Lamb waves reflected from the boundaries of a structure create additional side bands in the reconstructed signal. Although only a single mode travels and the structures has only one finite boundary where the Lamb wave is reflected, the reconstructed signal is composed of the main mode in the middle and two symmetric sidebands.

In this section, the existence of the sidebands due to boundaries is shown. Also, the symmetry of the reconstructed signal is shown. The test is conducted using a pair of PZT patches attached to the aluminum plate shown in FIG. 14. For the test, two rectangular PZTs with the same size (1.0 cm×1.0 cm) are attached in the middle of the plates. PZT A is mounted 15 cm away from a left boundary and PZT B locates 41 cm away from a right boundary of the plate. In this configuration, direct $S_0$ signal arrives at a sensor first followed by $S_0$ reflection from the left boundary. Because the arrival time of $A_0$ mode is much later than that of $S_0$ reflection, it is possible to truncate Lamb wave signal for the TRP neglecting the effect of multiple modes. The exciting frequency of a narrowband toneburst signal, the number of averaging, and the LNP gain were set to 130 kHz, 20 times, and 100, respectively.

Figure 26:
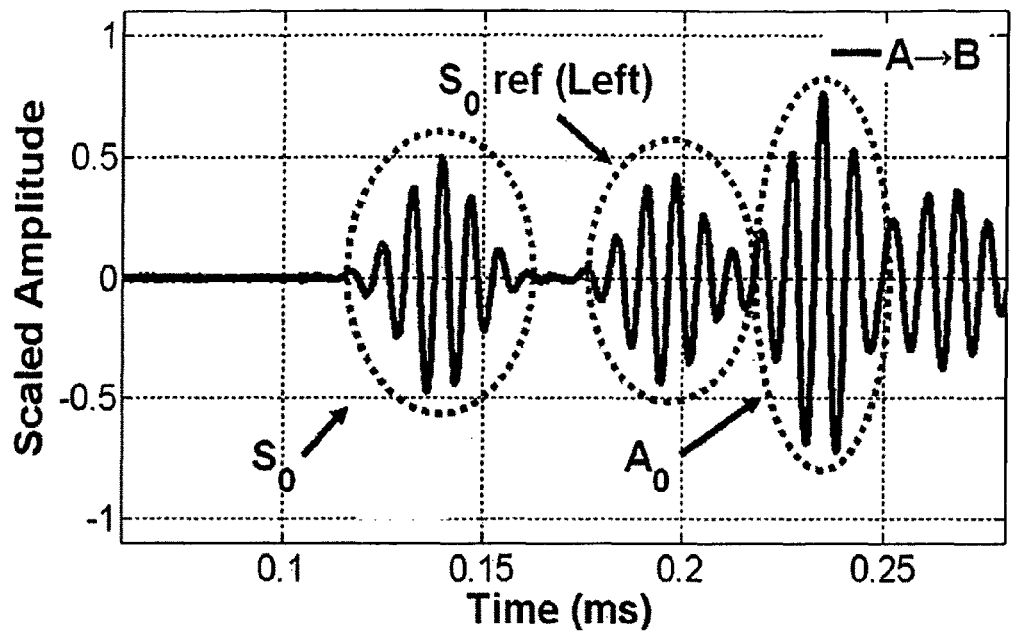
FIGS. 26 and 27 illustrate reciprocity and time reversibility of Lamb wave propagation in which PZT A and PZT B are 1.0 cm×1.0 cm.
Figure 27:
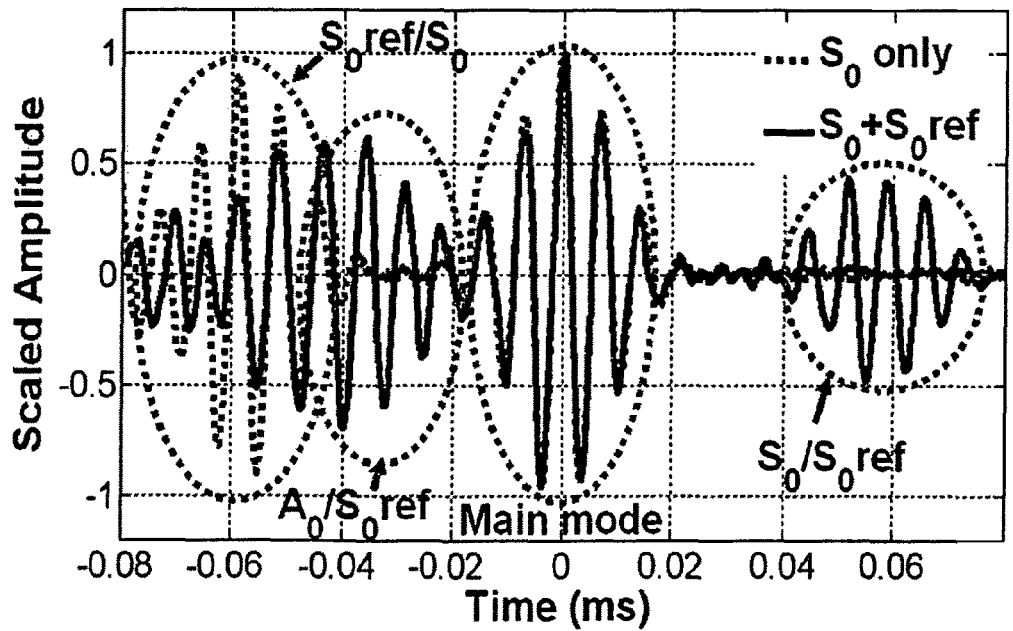

First, a signal in FIG. 26 is truncated at 0.1675 ms so that only a direct $S_0$ mode can be reversed and resent to the original location. Next, the TRP is conducted using same Lamb wave signal truncated at 0.215 ms. According to the graph in FIG. 26, the group velocities of $S_0$ mode is estimated to be 4.834 m/ms, which is slower than the velocity measured in the previous section. In FIG. 27, the sidebands due to reflections are shown. When the TRP is conducted including the direct $S_0$ mode as well as the $S_0$ reflection, a sideband appears around the main mode. The arrival time of the sideband which is in the right side of the main mode is 0.0587 ms, and it is close to the theoretical value of $\bar{t}_{DR}$. ($\bar{t}_{DR}=(r_D-t_R)/w(\bar{\omega})=(0.66-0.96)/4.834=0.062$ ms, where, w denotes the group velocity of a Lamb wave mode, and $r_D$, $r_R$ and $\bar{\omega}$ represent the wave traveling distance of a direct signal and a reflection, and an exciting frequency, respectively.) However, in the left side of the reconstructed signal, the sideband due to reflection is combined with an $A_0$ sideband by the reflection such that its symmetry is not fully shown. According to the test result, it is shown that the shape of the main mode in the reconstructed signal is hardly affected by the reflections, and the symmetric sidebands are produced by the effect of reflections. Again, the symmetry of the whole reconstructed signal can is preserved after the TRP by increasing the amount of signals reversed.

The Effects of PZT Size, Orientation, Shape and Bonding Condition on the TRP

The Effect of PZT Size

Figure 28:
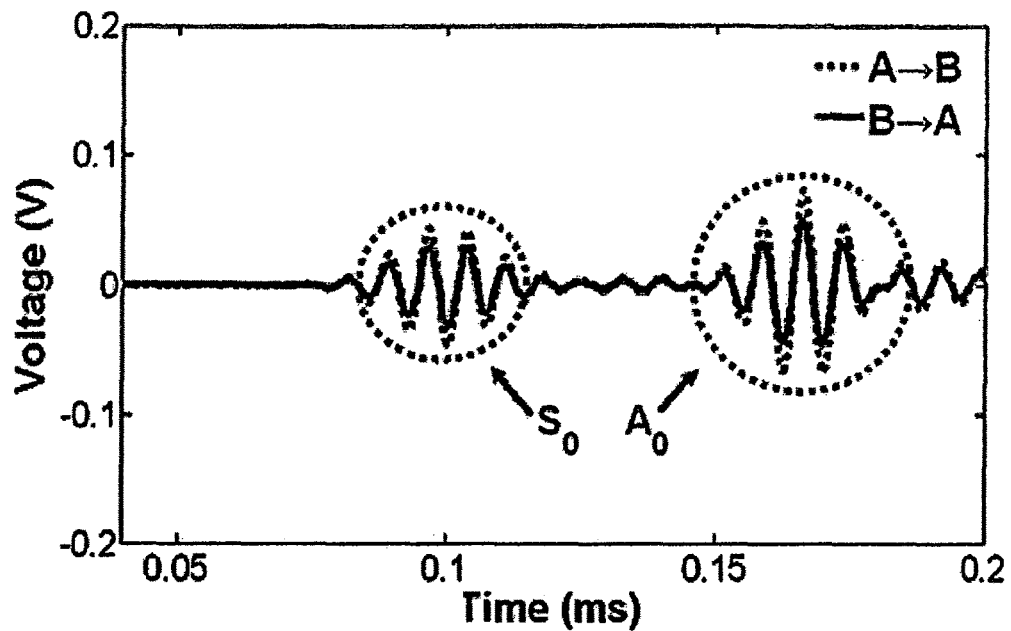
Figure 29:
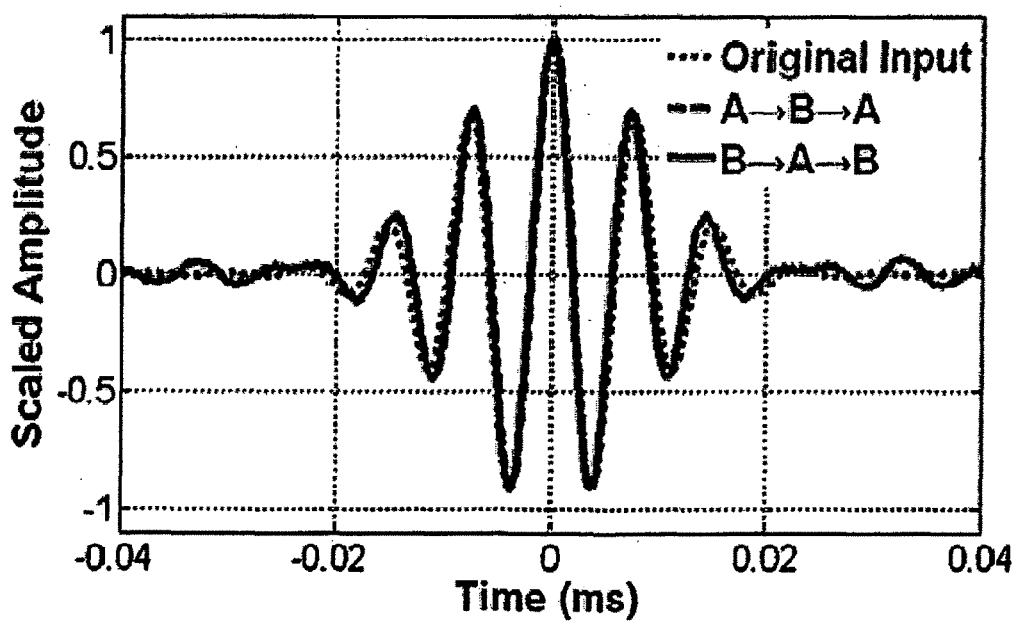

The effect of the PZT size difference on reciprocity and time reversibility is examined. In this section, the exciting frequency of the narrowband toneburst signal, the number of averaging, and the LNP gain were set to 130 kHz, 20 times, and 10, respectively. The forwarding signal A→B (signal AB) or B→A (signal BA) was truncated at 1 ms before it was reversed and resent to the original location. For the reciprocity and time reversal results presented in FIGS. 28 and 29, a 1.0 cm×1.0 cm PZT is used at location A and a 0.7 cm×0.7 cm PZT is attached at location B of the plate in FIG. 15. The observation of FIG. 28 reveals that the amplitude of the signal AB and signal BA are different although the shapes are still very similar. In particular, the amplitude of the response signal is bigger when the input is applied to the bigger PZT (PZT A) than the smaller one (PZT B). However, the different sizes of the PZTs do not affect time reversibility much as illustrated in FIG. 29.

Figure 30:
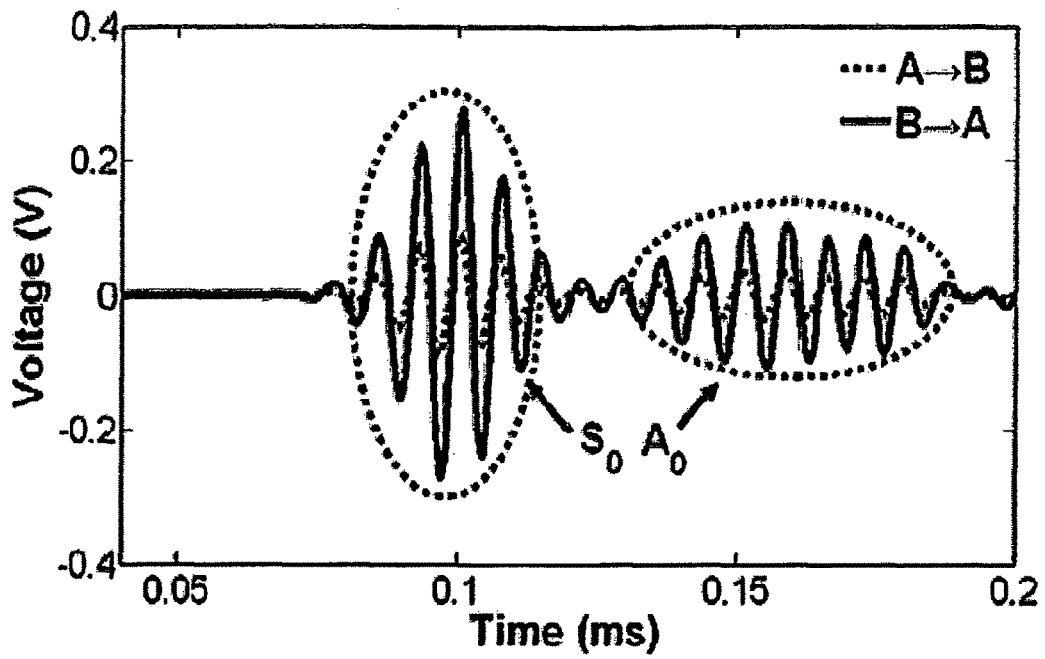

Next, the size difference between PZT A and B has been increased. In the experiment shown in FIGS. 30 and 31, the size of PZT B is increased to 2.0 cm×2.0 cm while keeping the size of PZT A to be 1.0 cm×1.0 cm. Patterns similar to FIGS. 28 and 29 are observed. However, the amplitude of signal AB is bigger than that of signal BA in FIG. 28 because a bigger PZT is used at location B. In addition, the time shift of the time reversal signal is noticeable in FIG. 31. It is speculated that this time shift is due to the size difference of the PZTs.

As described hereinabove, the amount of time delay in an excitation signal is estimated as:

$$t_D = \frac{\tan^{-1}\left(\frac{\omega C R_W}{1+\omega^2 C^2 R(R_W+R)}\right)}{\omega} \quad (54)$$

where, $\omega$, $R_W$, C, R denote an exciting frequency, the impedance of a AWG, and the capacitance and resistance of a PZT in an equivalent series circuit, respectively. Using impedance analyzer, the C and R values for PZT A and PZT B are measured, and the amount of time delay introduced by each PZT are calculated in Table 6.

Figure 31:
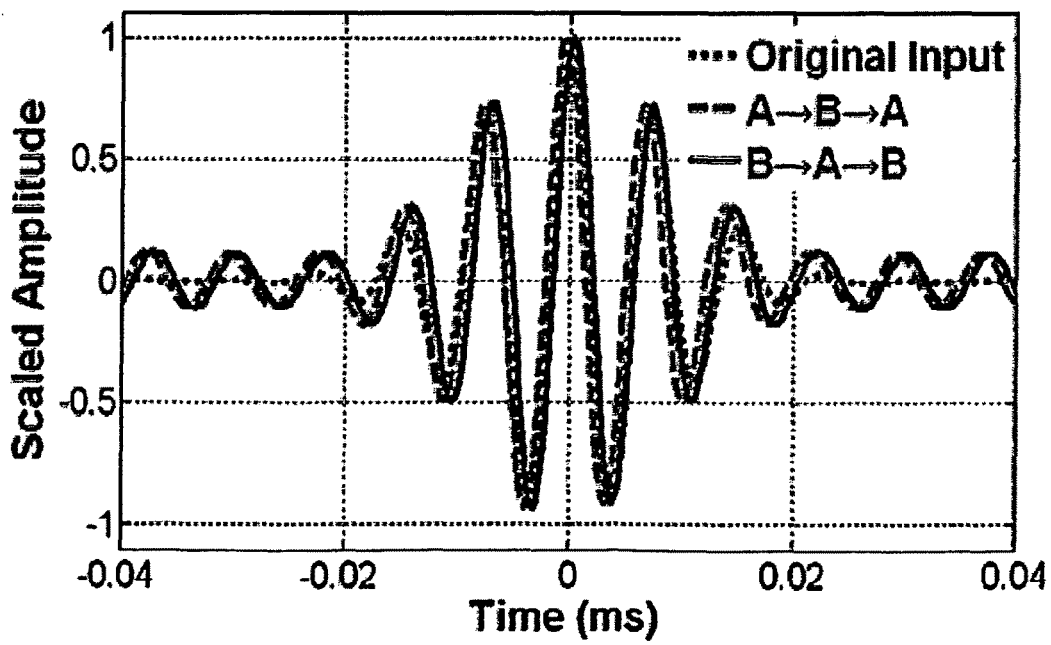

In FIG. 31, a reconstructed signal following path A→B→A is shifted 0.4 μs to the left, and a signal from path B→A→B is moved same amount to the right. This shows that the time delay induced by the PZT B is larger than that of PZT A. When the reconstructed signals are obtained at higher sampling rate, the difference between theoretical calculation and observed time delay will be minimized.

According to the test result, it can be concluded that the TRP can be affected by the size difference of two transducers, and the location of the main mode is shifted either to the left or to the right. Therefore, the sizes of the PZTs in the TRP should be almost identical to minimize their effects on the TRP.

TABLE 6

The equivalent capacitance, resistance, and the time delay of the PZT A and B

| | Equivalent Capacitance | Equivalent Resistance | Time delay at each PZT |
|---|---|---|---|
| PZT A | 2.1326 ηF | 47.50 Ω | 0.10489 μs |
| PZT B | 8.2011 ηF | 12.35 Ω | 0.38332 μs |

The Effect of PZT Orientation and Shape

Figure 32:
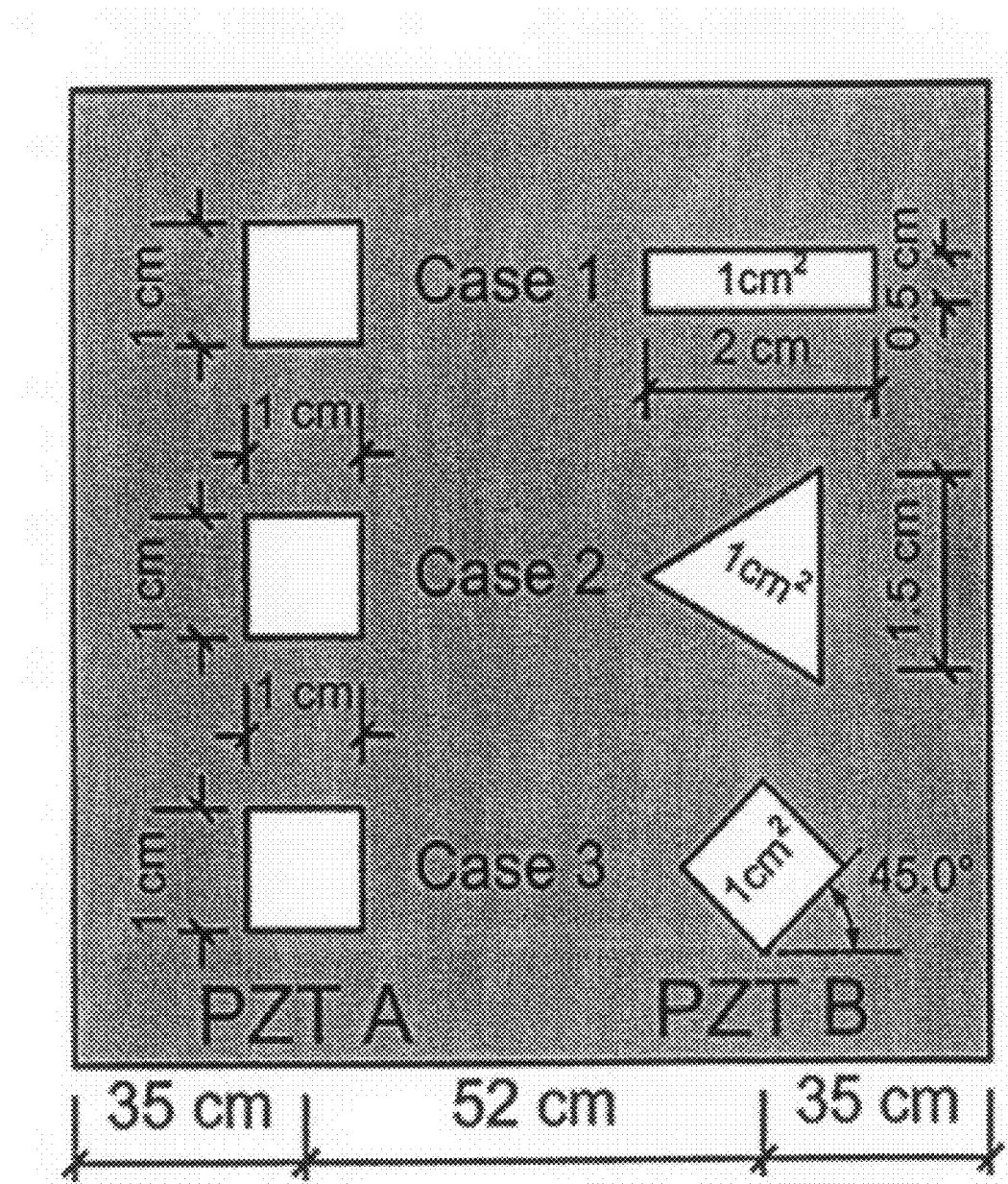
FIG. 32 illustrates PZT transducers with different shape and orientations used in the experiments described herein.
Figure 33:
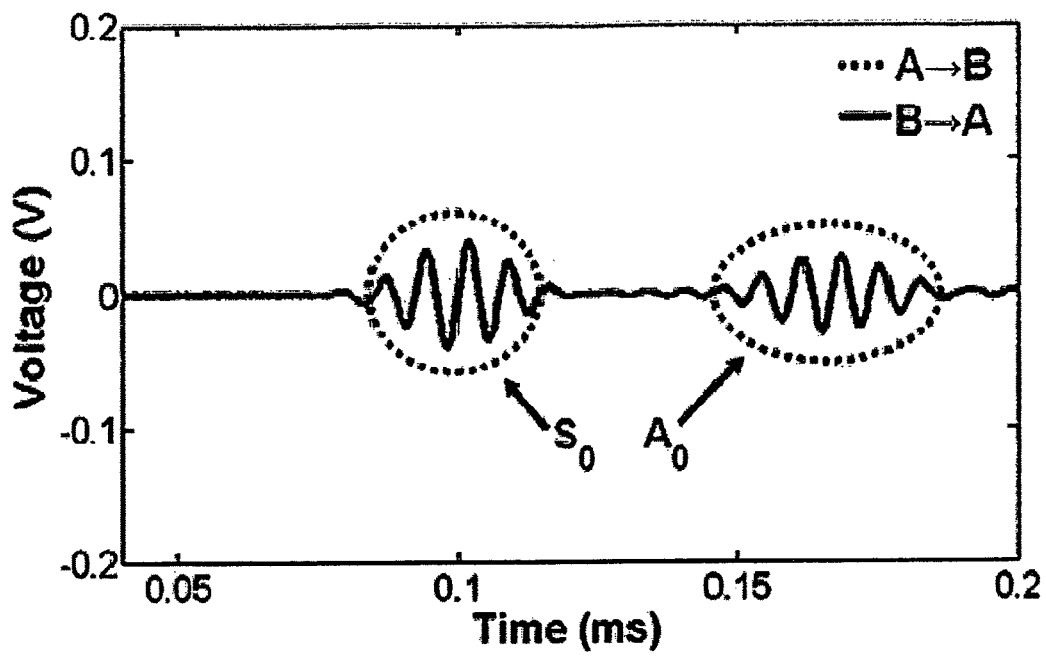
Figure 34:
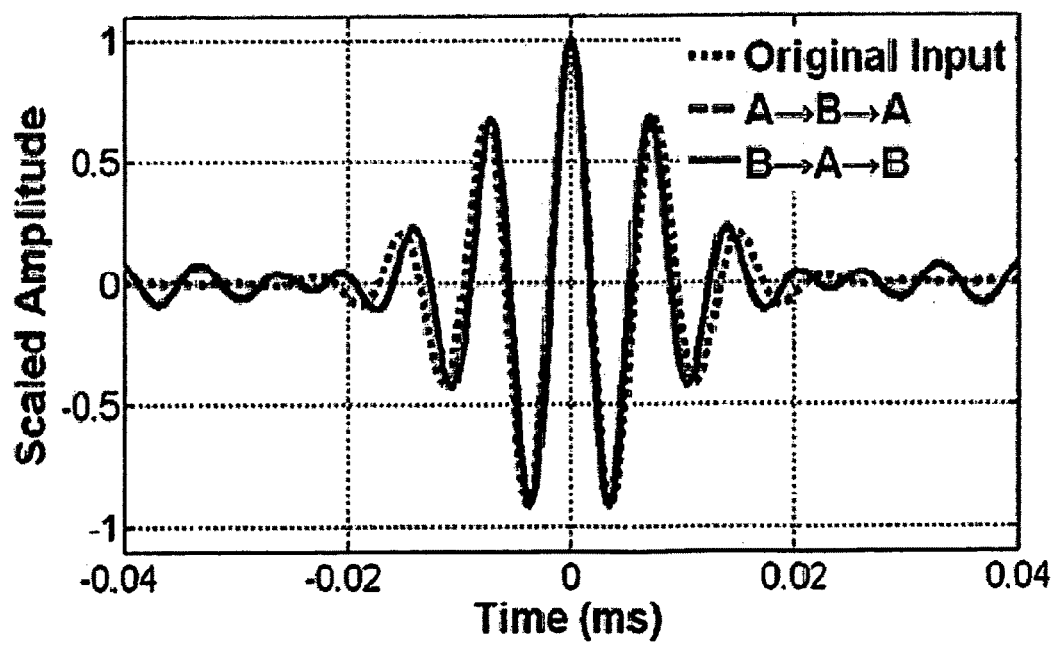
Figure 36:
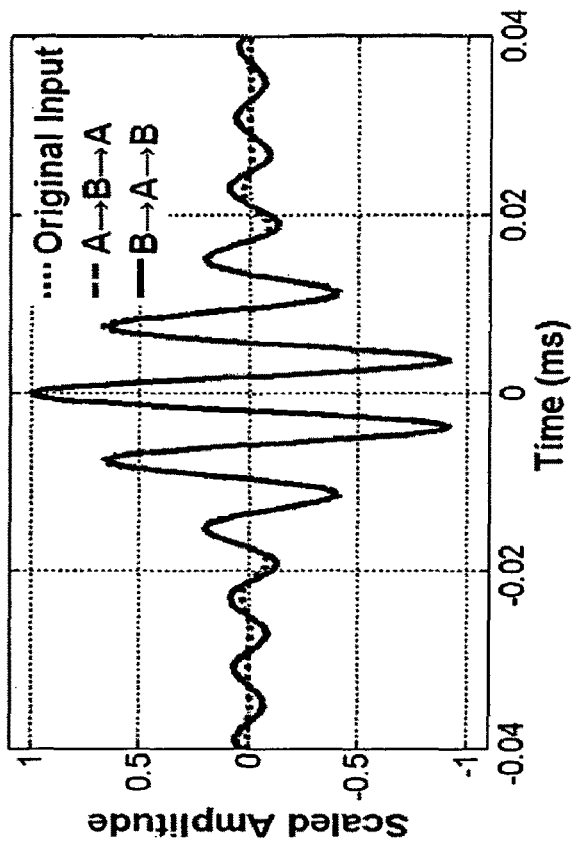
Figure 35:
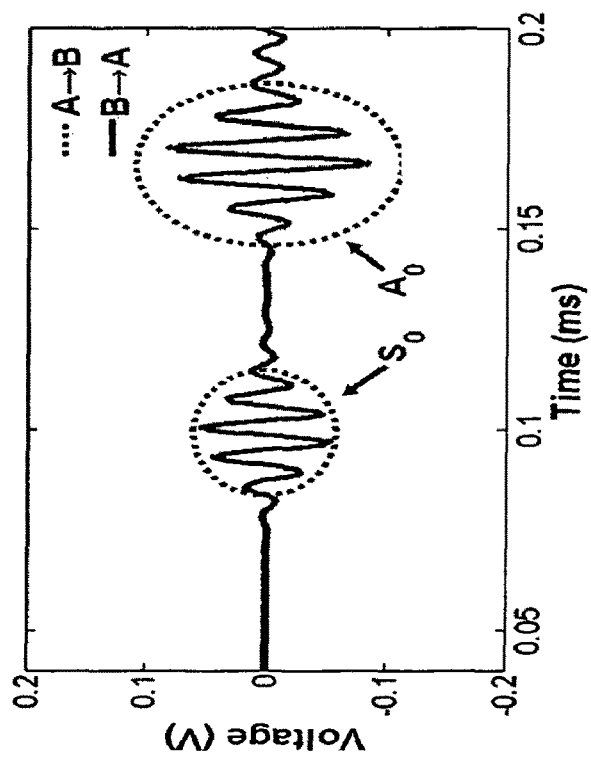
Figure 38:
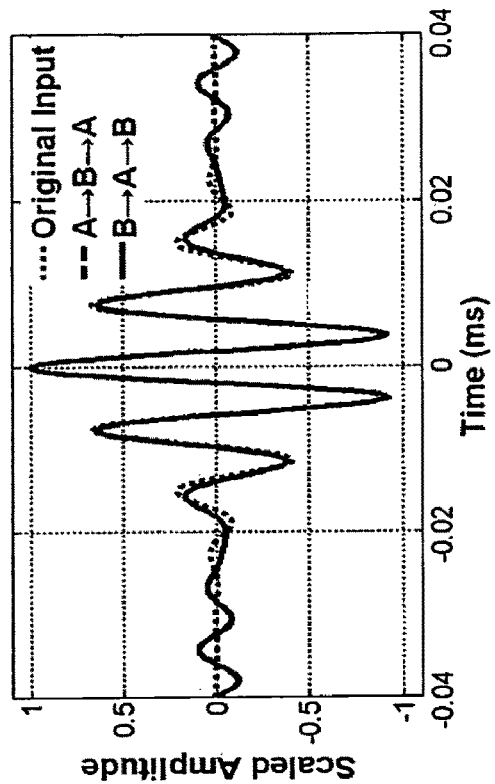
Figure 37:
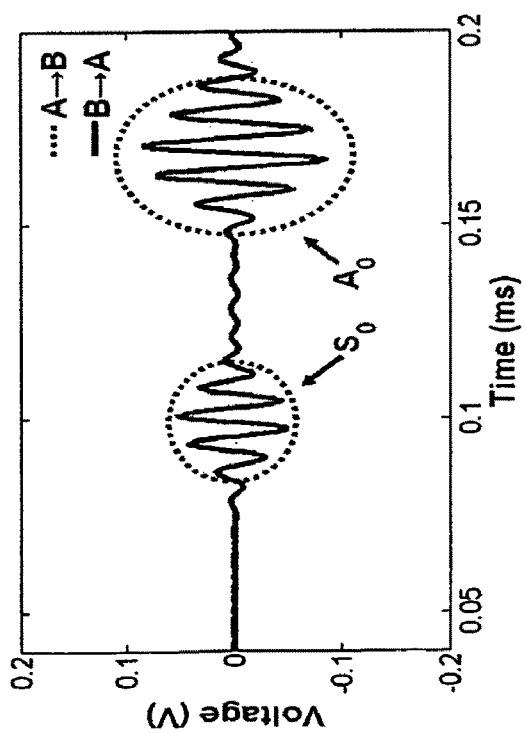

In this section, the effect of the PZT orientation and shape difference on reciprocity and time reversibility is investigated. For the reciprocity and time reversal results, three different test sets were prepared on the aluminum plate [FIG. 32]. For all cases, one PZT is fixed to have a shape of a square (1 cm×1 cm), and the other PZT is a rectangle (2 cm×0.5 cm), an equilateral triangle of 1.52 cm side, and a 45 degree rotated square (1 cm×1 cm) for each case. Note that all PZTs have same area (1 cm²). Other test setup parameters such as the exciting frequency are identical to the ones in the previous section.

The observation of FIGS. 33 and 34, FIGS. 35 and 36, and FIG. 37 suggest that the amplitude of the response signals AB and BA are almost identical. The different shapes of the PZTs also do not distort time reversibility as presented in FIGS. 33 and 34, FIGS. 35 and 36, and FIG. 37. In comparison with the result in the previous section, it can be inferred that the reciprocity of Lamb wave propagation can be preserved if the area and bonding condition of each PZT is identical.

The Effect of PZT Bonding Condition

Another issue that has to be addressed in field implementation is varying bonding conditions of PMT patches. Although workmanship for PMT installation can be reasonably well controlled, the PZT bonding condition will continuously change over long time period. For periodic monitoring, there is no guarantee that consistence bonding conditions can be achieved every time the patch is instrumented. Therefore, it is of great importance to investigate the effect of the PZT bonding condition on reciprocity and time reversibility.

Figure 40:
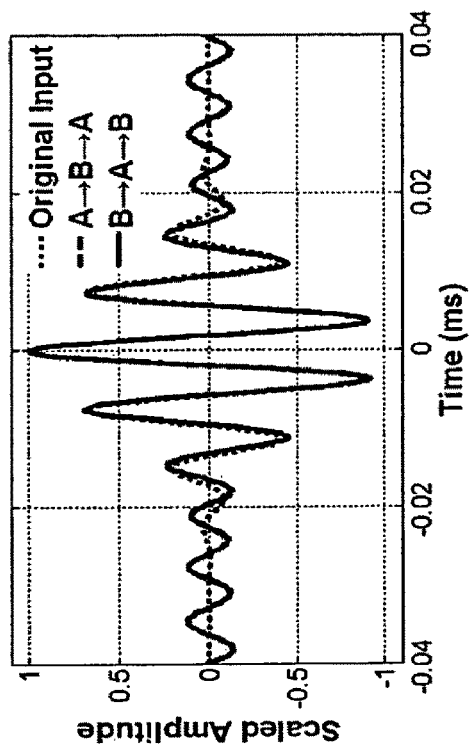
Figure 39:
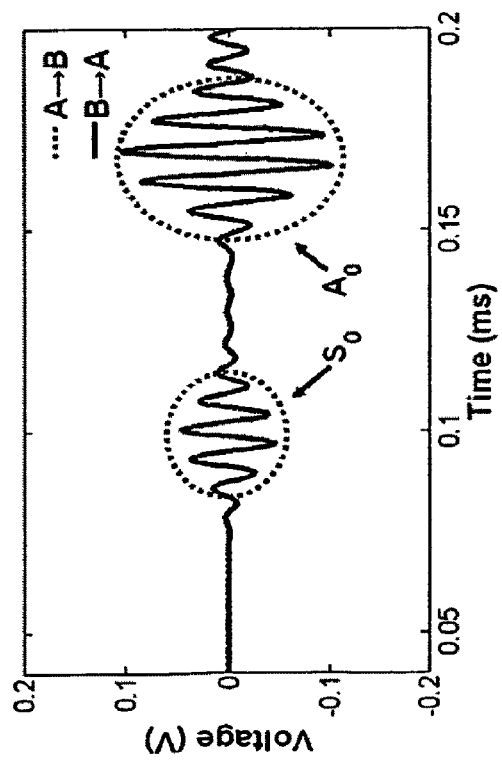
Figure 41:
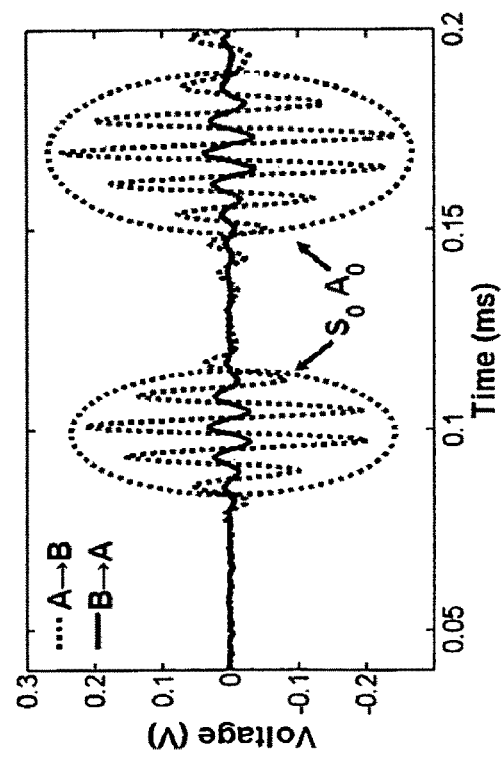

First, a test which shows the effect of different bonding material is conducted. PZT A is attached to the aluminum plate in a similar manner using commercial cyanoacrylate adhesive. However, PZT B is mounted using conductive epoxy (Chemtronics CW2400). Other test setup parameters such as the exciting frequency are identical to the ones described hereinabove in the section entitled "The effect of PZT size". As shown in FIGS. 39 and 40, the reciprocity and time reversibility are preserved without regard to the bonding material. Another test is designed to show the effect of irregular bonding. To simulate a partially debonded PZT, a small piece of a Teflon tape is inserted between PZT B and the aluminum plate. As a result, only 70% of the PZT B surface is fully bonded to the aluminum surface at location B. Because of the low amplitude of the measured signal compared to other test cases, the LNP gain was set to 100 in this test case. The results of reciprocity and time reversibility are reported in FIGS. 41 and 42. A huge difference between the two forwarding signals is shown in FIG. 41.

Figure 42:
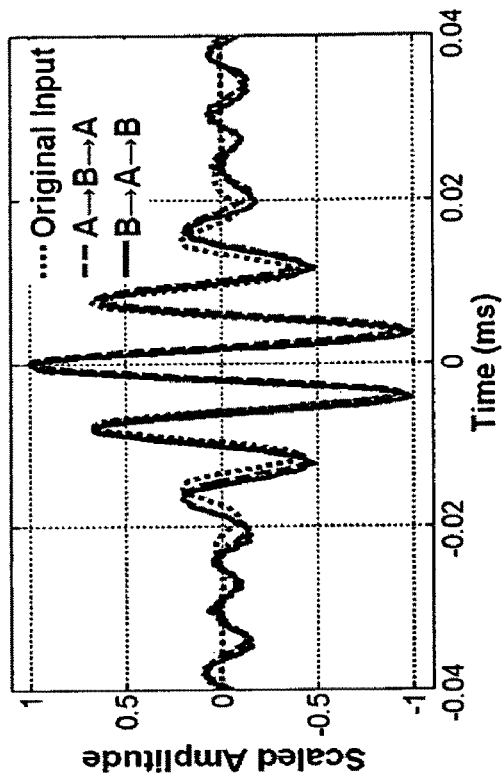

In FIG. 42, the shift of the reconstructed signal and the magnitude difference of two paths are observed due to irregular bonding condition which reduces the effective actuating/sensing area of transducer. Because size effect and bonding condition introduced similar shift of the signals after the TRP, further research on bonding effect will be conducted with relation to size effect.

Effect of Environmental and Operational Variations

To deploy a monitoring system for in-situ infrastructures, the monitoring system should be robust against operational and environmental variations in order to minimize false-alarming of damage. In this section, several operational and environmental parameters of a test specimen are varied to demonstrate that the proposed reference-free NDT technique is robust against these variations.

Figure 15:
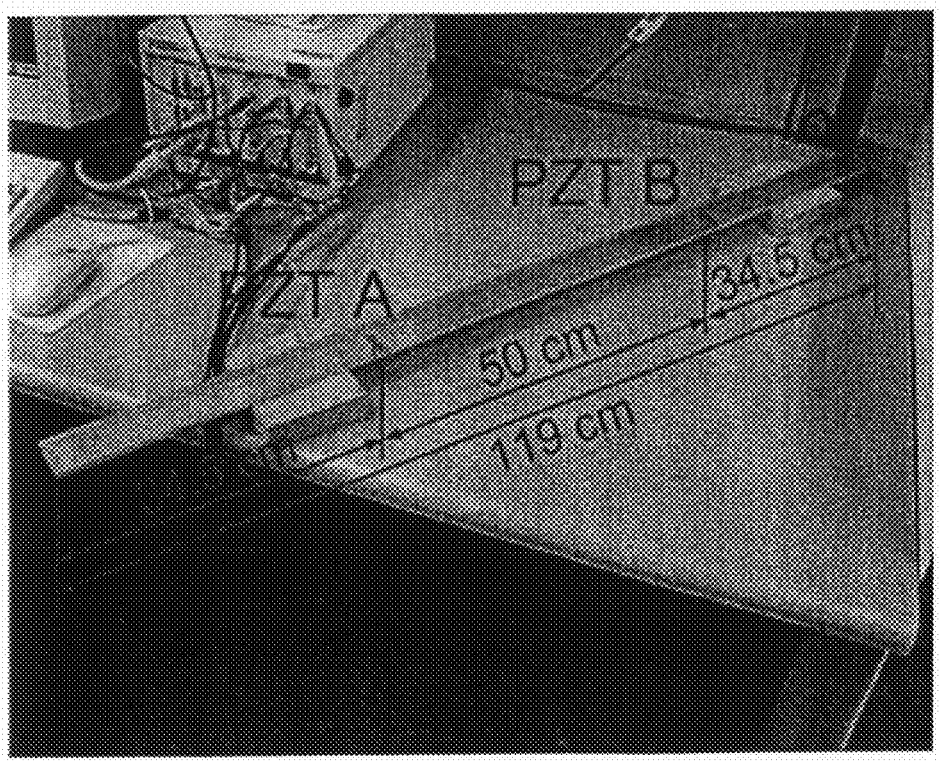

As shown in FIG. 15, a 119 cm×5.08 cm×0.6 cm aluminum bar is used in this section because of its simplicity. In this section, the exciting frequency of the narrowband toneburst signal, and the LNP gain were set to 150 kHz, and 10, respectively. Throughout the tests in this section, signals were measured only one time without averaging. For the TRP, the forwarding signal AB or BA was truncated at 1 ms before it was reversed and resent to the original location.

Temperature Variation

In-situ infrastructures such as steel bridges are often subjected to daily and seasonal temperature variations. It should be noted that the temperature variation can change the material property and boundary condition of the structure as well as the properties of the sensors. In return, they introduce changes in the measured response signals. Therefore, developing a NDT technique which is robust to temperature variation is of great importance in order to prevent false-positive alarming of damage.

Figure 44:
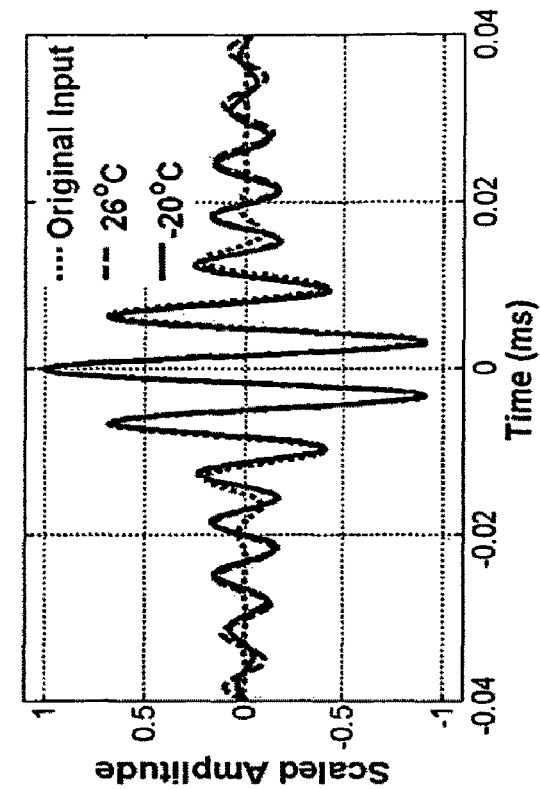
Figure 43:
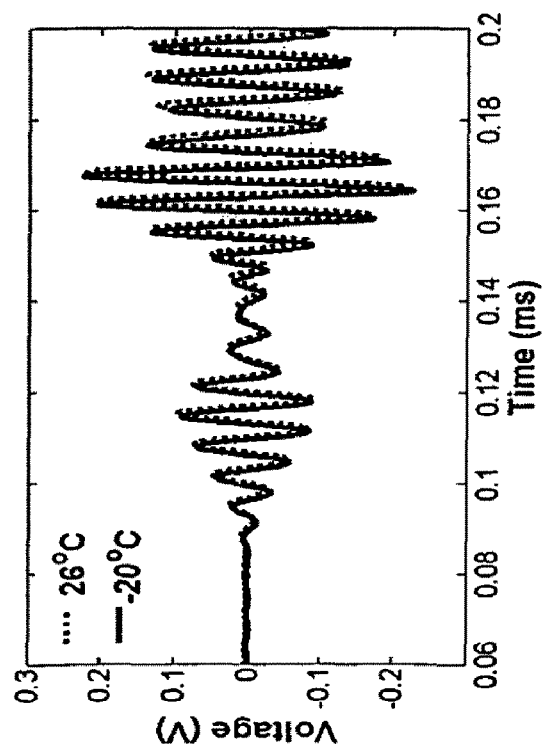
Figure 46:
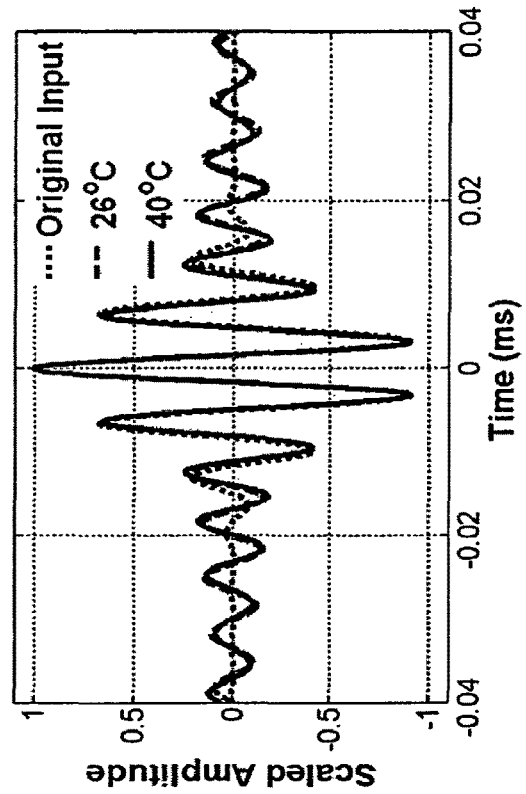
Figure 45:
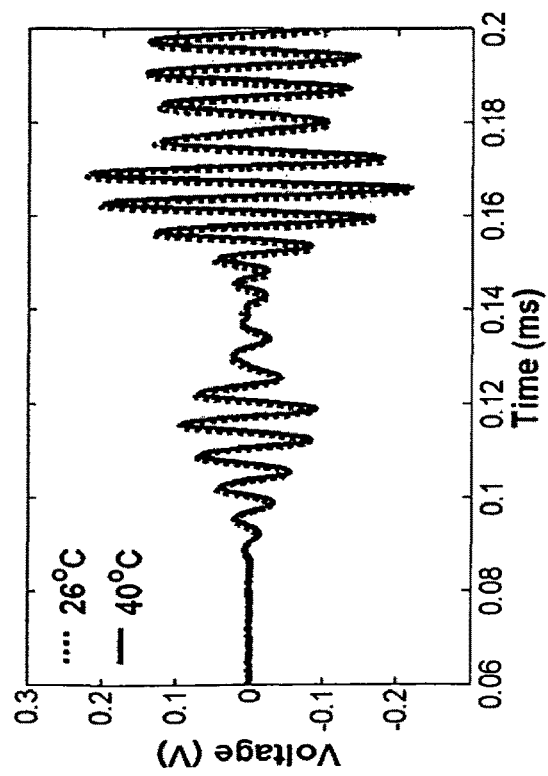

In this section, the influence of varying temperature on the TRP was investigated. First, the aluminum bar with 2 PZT sensors in FIG. 15 was tested after it was refrigerated to −20° C. (4° F.). Next, the middle part of the aluminum bar including PZTs was heated to 40° C. (104° F.). Then, the results from two cases were compared with a room temperature (26° C. (79° F.)) test case. The responses corresponding to the two different temperature conditions are shown in FIG. 43 and FIG. 45, respectively. While the amplitude changes were negligible, a noticeable phase shift of the response signal was observed. According to the test results, the temperature increase seems to decrease the wave propagation speed. However, it was observed that the temperature variation did not significantly affect the TRP because the TRP automatically compensated the phase shift of the forwarding signal during its time reversal procedure. Since temperature variation mainly causes a phase shift, the shape and symmetry of the reconstructed signal are preserved even in the presence of the temperature variation [FIG. 44, FIG. 46, Table 7]. Therefore, it is expected that daily and seasonal temperature variations of a bridge structure will not affect the proposed reference-free NDT technique.

TABLE 7

Damage indices in different temperature cases

| Degree (° C.) | TI | SI |
|---|---|---|
| −20 | 0.0249896 | 0.994325 |
| 26 | 0.0207283 | 0.999920 |
| 40 | 0.0372928 | 0.999685 |

Ambient Loading

Due to normal traffic on in-situ bridge structures, the vibration responses of the bridges are often dominated by traffic loading. Therefore, it is very difficult to single out the guided wave responses generated only by the active sensing device at the presence of more predominant vibration responses due to traffic. Although filtering can minimize the effect of traffic-induced vibrations, their effects cannot be completely removed.

Figure 48:
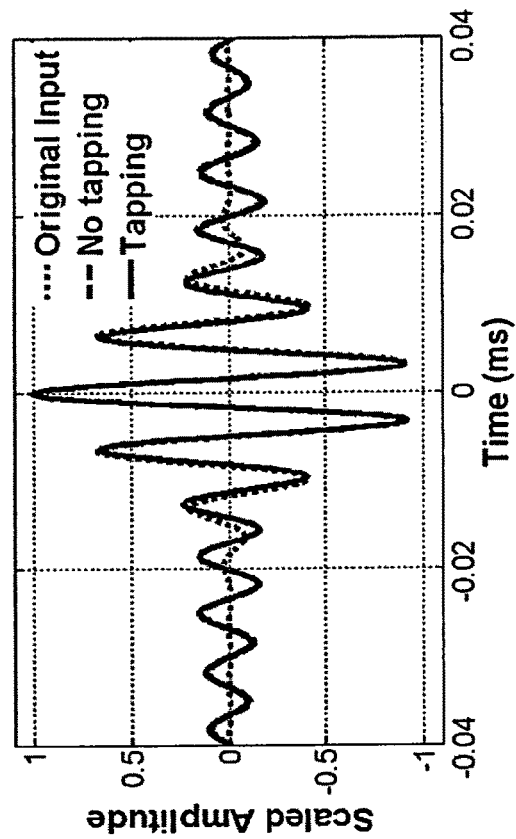
Figure 47:
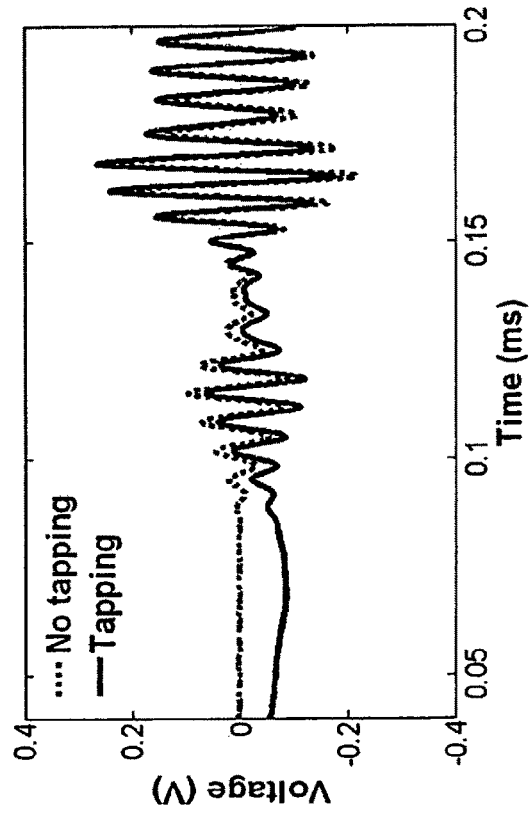

In this section, the effect of ambient vibrations on reciprocity and time reversibility was investigated. In order to simulate background noise or ambient vibration, one end of an aluminum bar was tapped about 4 times per second (240 Hz) by a steel ruler. As is shown in FIG. 47, tapping by a ruler generated fluctuation in a forwarding signal from PZT A to PZT B. In spite of using LNP with 3 kHz to 1 MHz bandpass filter, the effect of tapping remained. However, in FIG. 48, the tapping effect was not shown in the reconstructed signal. It is speculated that the frequency of the fluctuation is much lower than the exciting frequency such that its effect is not clearly seen when the reconstructed signal is zoomed in to see only main mode. The main idea of using proposed damage indices is to extract a damage sensitive feature from the main mode. Here, even though overall signal is fluctuating, the shape of the main mode is maintained. Therefore, the effect of additional loading can be compensated by observing the main mode using proposed damage indices.

TABLE 8

Damage indices in different loading conditions

| | TI | SI |
|---|---|---|
| No Tapping | 0.0207283 | 0.999920 |
| Tapping | 0.0200829 | 0.999343 |

Boundary Condition Changes

Figure 50:
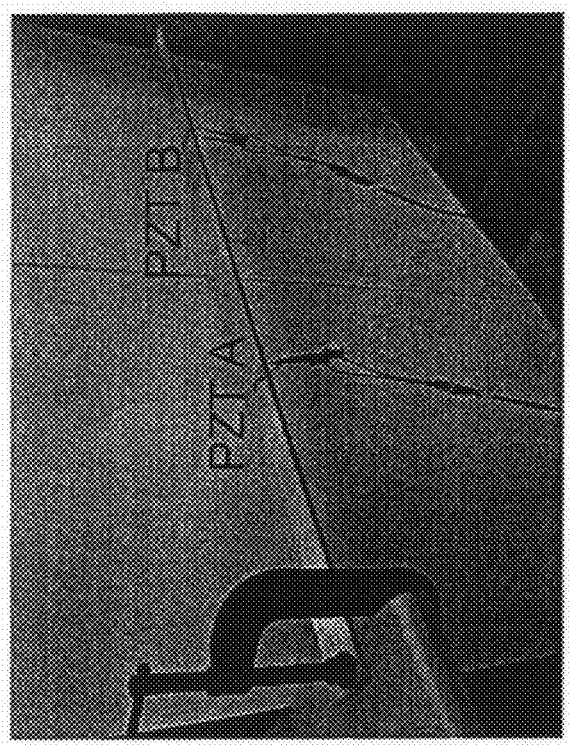
Figure 49:
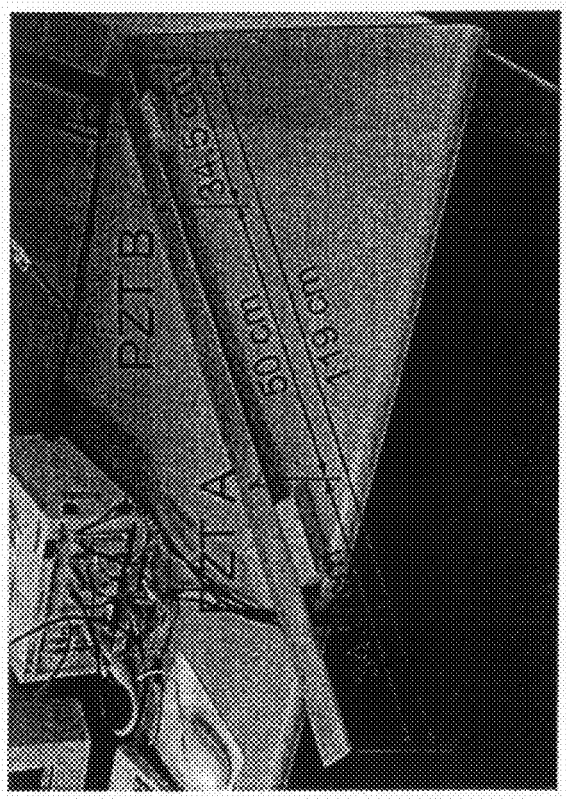
Figure 52:
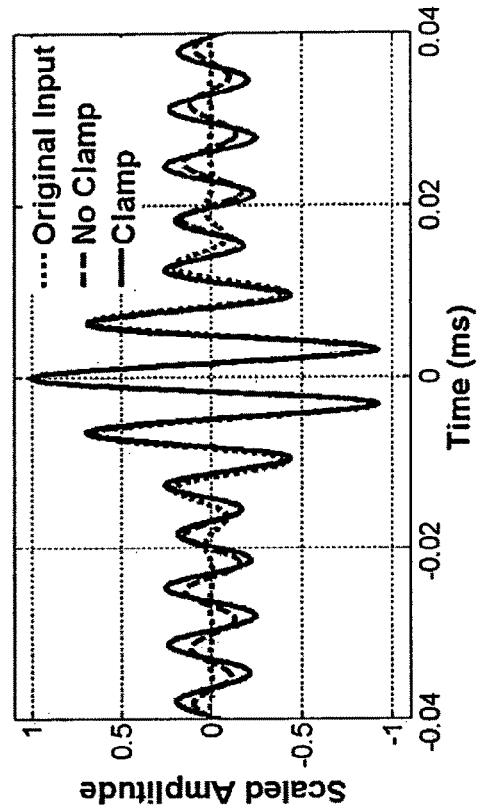
Figure 51:
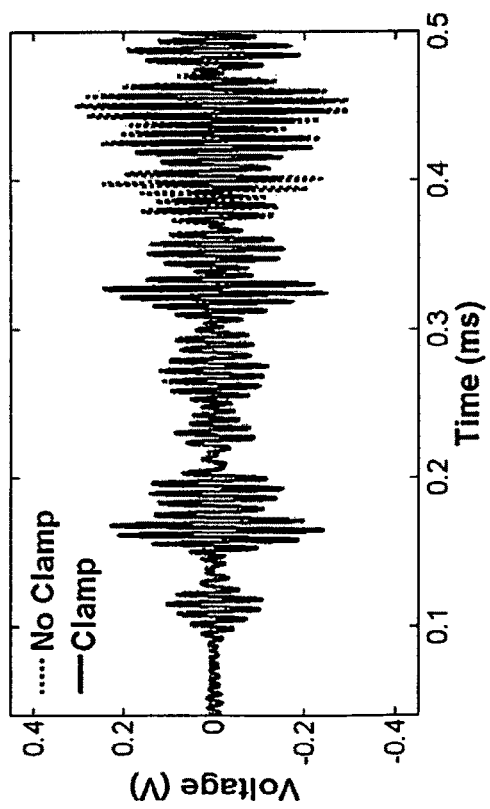

The robustness of the current invention against changing boundary conditions was investigated using the two different configurations shown in FIGS. 49 and 50. In FIG. 49, the beam was laid on top of two wooden blocks. In FIG. 50, the one end of the beam was fixed using a clamp. FIGS. 51 and 52 shows the forwarding and reconstructed signals obtained from these two configurations. It was observed that the boundary condition change affected the Lamb wave modes reflected from the clamped edge of the bar as shown in FIG. 51. However, it is shown that the damage and symmetry indices will be invariant of the varying boundary conditions [FIG. 52, Table 9].

TABLE 9

Damage Indices in Different Boundary Conditions

| | TI | SI |
|---|---|---|
| No Clamp | 0.0207283 | 0.999920 |
| Clamp | 0.0239801 | 0.999513 |

Additional Layer: The Effect of Painting Layer

Figure 53:
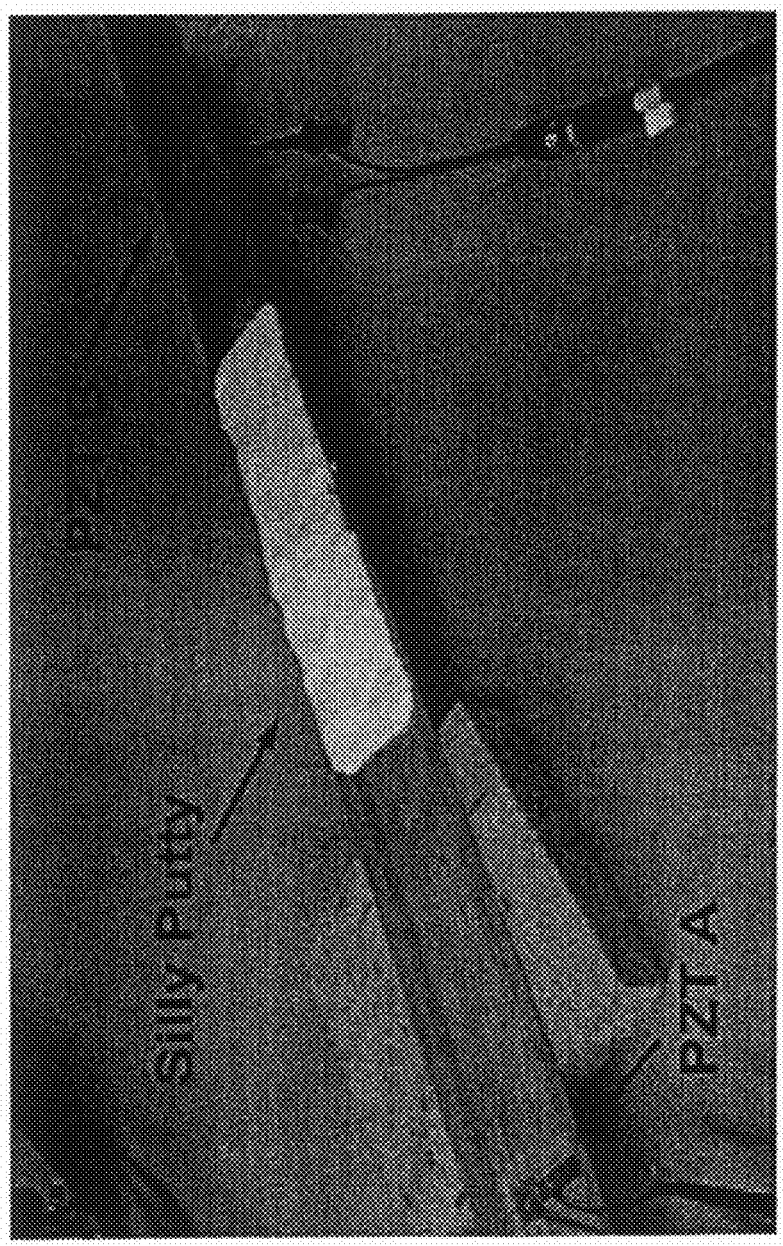
FIG. 53 illustrates a surface condition change using an industrial silly putty.
Figure 55:
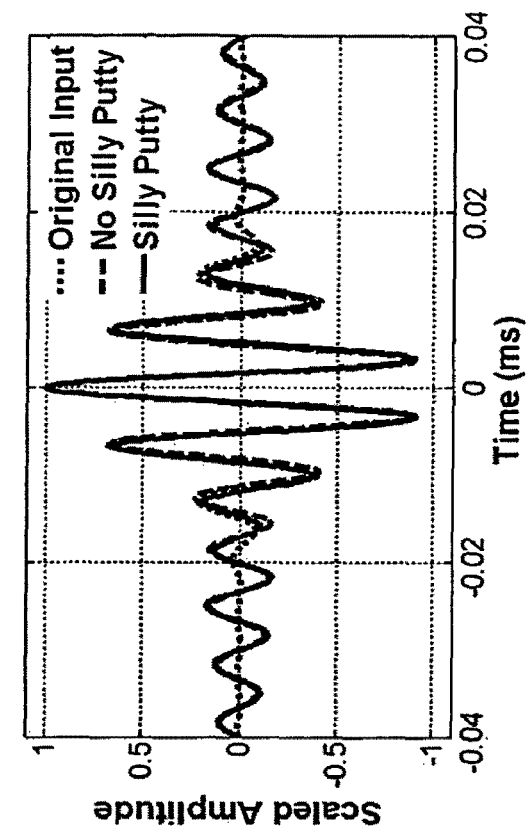
Figure 54:
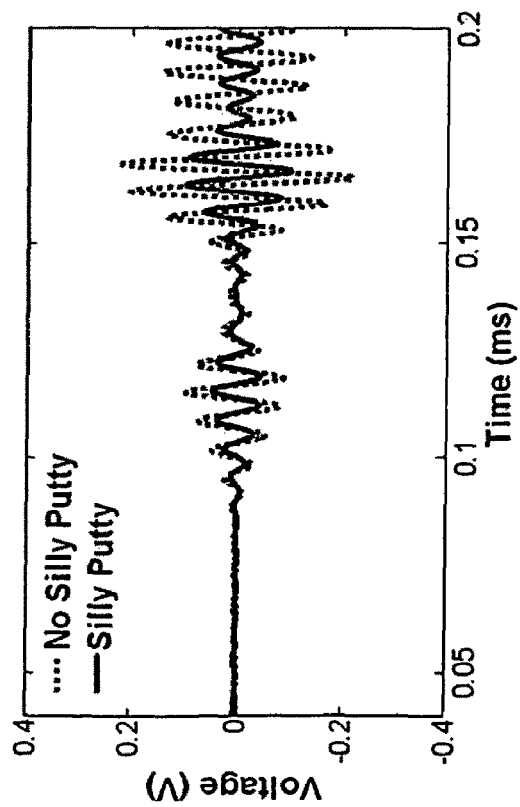

For steel bridge structures, preventive painting should be applied on a regular basis (often every 2 or 3 years). In this section, the effect of an additional layer or a surface condition change on the TRP is investigated. To simulate the surface condition change, industrial putty was attached on the test beam as shown in FIG. 53. FIG. 54 indicates that the attachment of the industrial putty significantly attenuated the forwarding response signal and the dispersion characteristics was also altered. However, the shape of the reconstructed signal was preserved again [FIG. 55]. It should be noted that the reconstructed signal shown in FIG. 55 is scaled so that it can be better compared with the original input signal. In addition, Eq. (1) shows the proposed TI is not affected by the amplitude difference between the original input and reconstructed signal.

Effect of Defects on the TRP

The ultimate application of the current invention relies on its ability to correlate defects to changes in time reversibility. Here, a brief discussion on the effect of defects on the TRP is provided.

Wave Scattering Source

Figure 56:
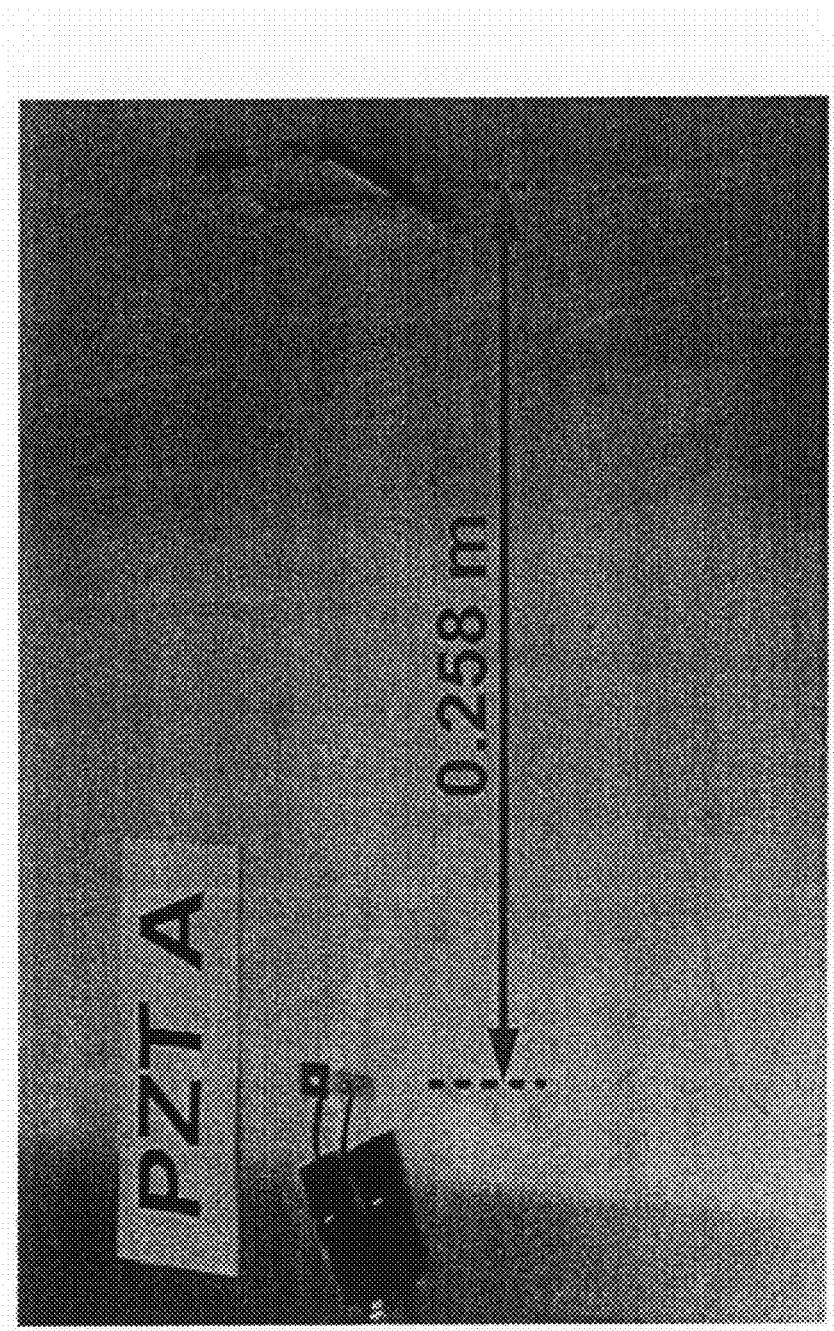
FIG. 56 illustrates a steel block (5.0 cm H×4.5 cm W×0.6 cm T) attached between PZTs A and B.
Figure 58:
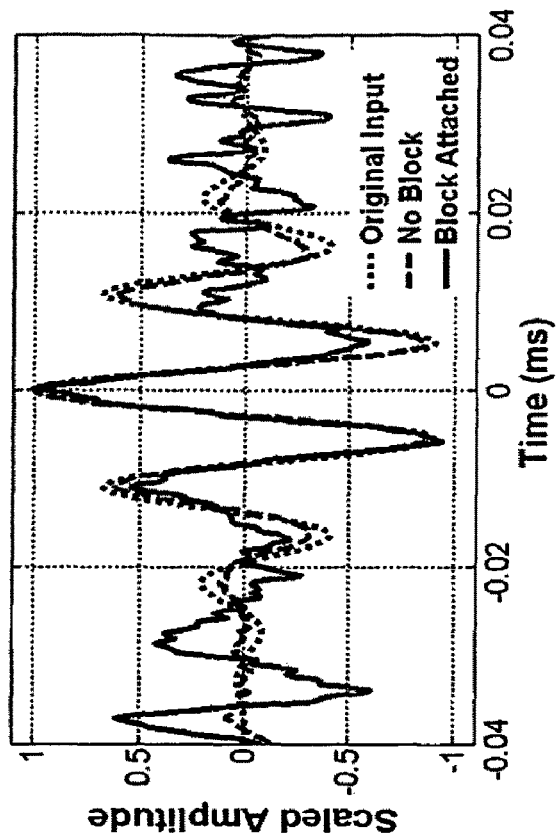

Damage is simulated by attaching a steel block or introducing a small notch along the wave propagation path. The first damage case is presented in FIG. 56. A steel block of 5.0 cm×4.5 cm×0.6 cm is attached in the middle of PZTs A and B in FIG. 14. For the TRP, only the first arrivals of $S_0$ and $A_0$ modes have been reversed (t=0.22 ms). In this way, the contribution of reflections to the time reversal has been removed. The effects of mode conversion on the forwarding response signal and the reconstructed signal are illustrated in FIGS. 57 and 58.

Figure 57:
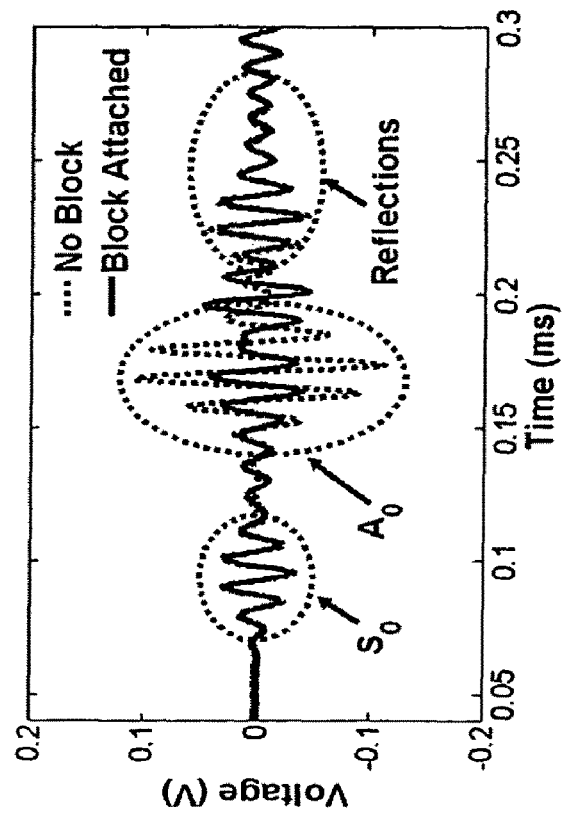

Two noticeable changes are observed in FIG. 57. First, the amplitudes of $S_0$ and $A_0$ modes are reduced due to the block attached between PZTs A and B. In particular, $A_0$ mode has been more severely influenced by attenuation than $S_0$ mode.

Second, the shapes of $S_0$ and $A_0$ modes also have been altered. It is suspected that the shape changes are caused by a combination of mode conversion and reflection at the block location. Although attenuation itself does not change the time reversibility of the reconstructed signal, additional changes due to mode conversion and reflection seem to degrade the time reversibility. FIG. 58 shows the distortion of the time reversibility due to the attached block.

Notch

Figure 59:
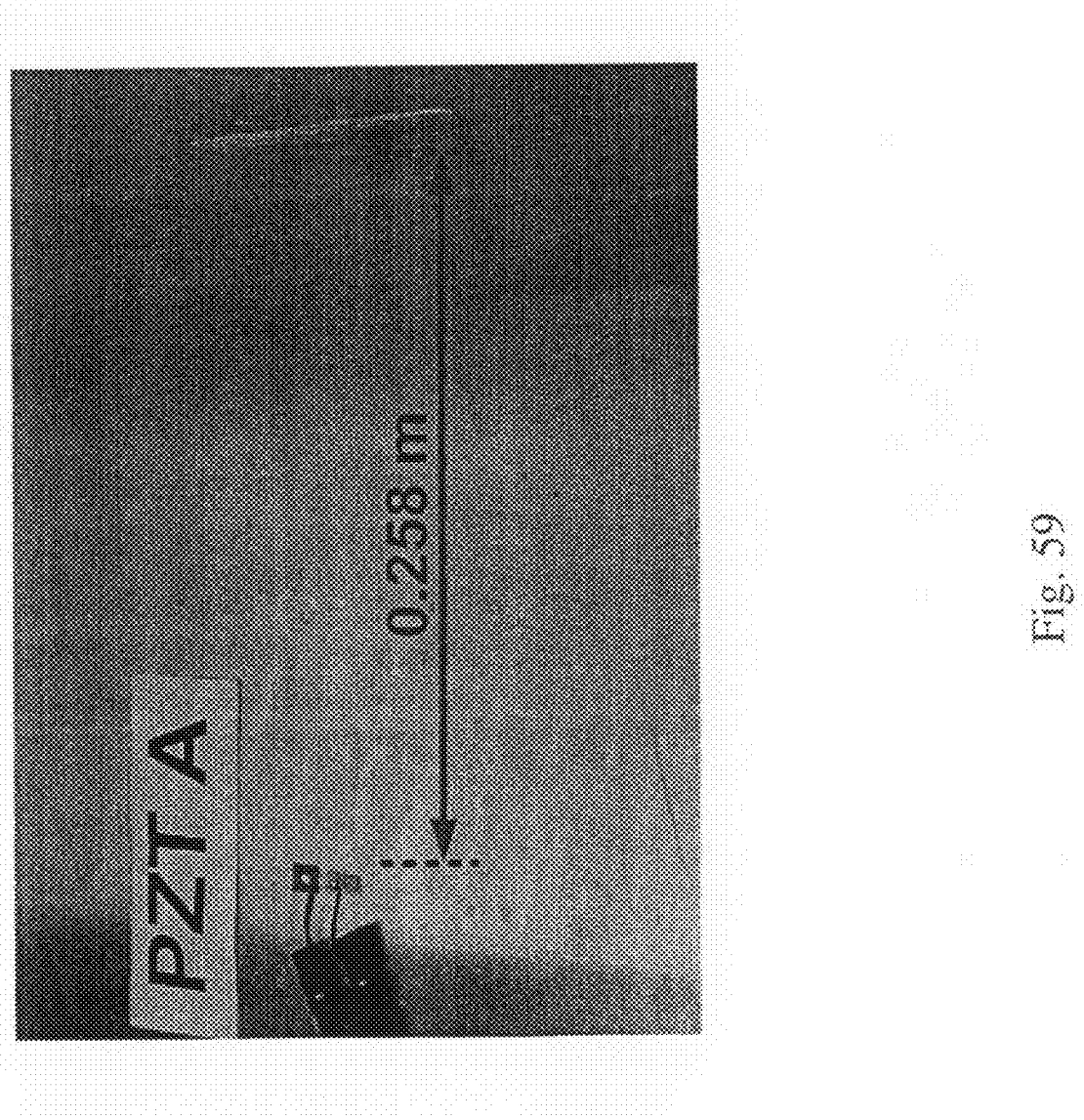
FIG. 59 illustrates a notch of 8 cm W×0.2 cm T×0.3 cm D between PZTs A and B.
Figure 61:
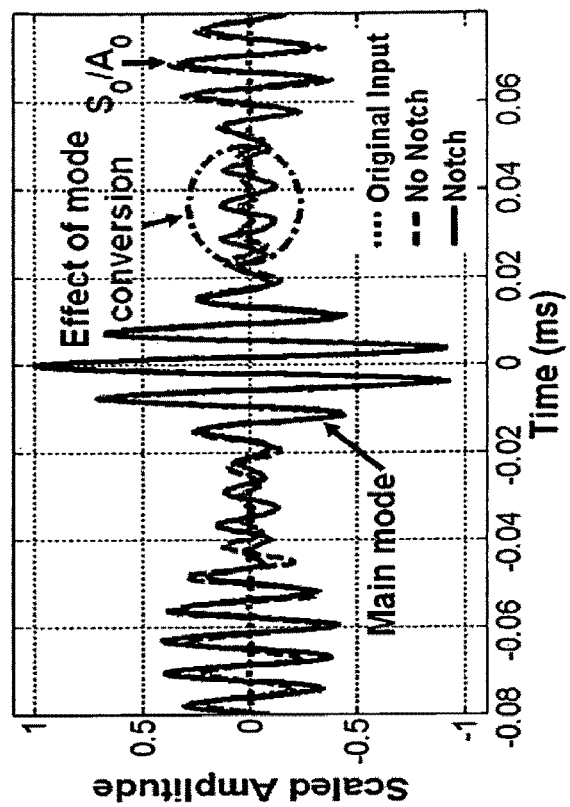
Figure 60:
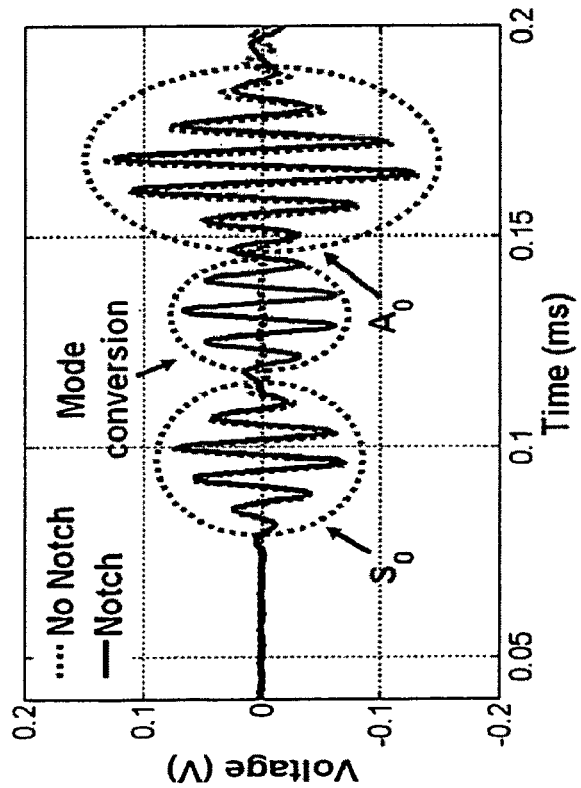

Next, a notch is introduced in the middle of PZTs A and B as shown in FIG. 59. All the experimental conditions of this damage case are identical to the previous one except the simulated defect. The appearance of mode conversion due to the notch is shown in FIGS. 60 and 61. Based on the arrival time of the $A_0$ and $S_0$ modes, their group velocities are estimated to be 5.163 m/ms and 3.025 m/ms at 130 kHz. Then, the arrival times of additional modes due to mode conversion at the notch location ($S_0/A_0$ and $A_0/S_0$) are estimated to be 0.135 ms. Because the notch is introduced at the exact middle point of the wave propagation path, two mode-converted signals arrive at the same time. These estimated arrival times match well with those of the additional modes observed in FIG. 60, confirming that these are, in fact, additional modes produced by mode conversion. However, the mode conversion due to the notch did change time reversibility very little as shown in FIG. 61.

Truncation

Figure 62:
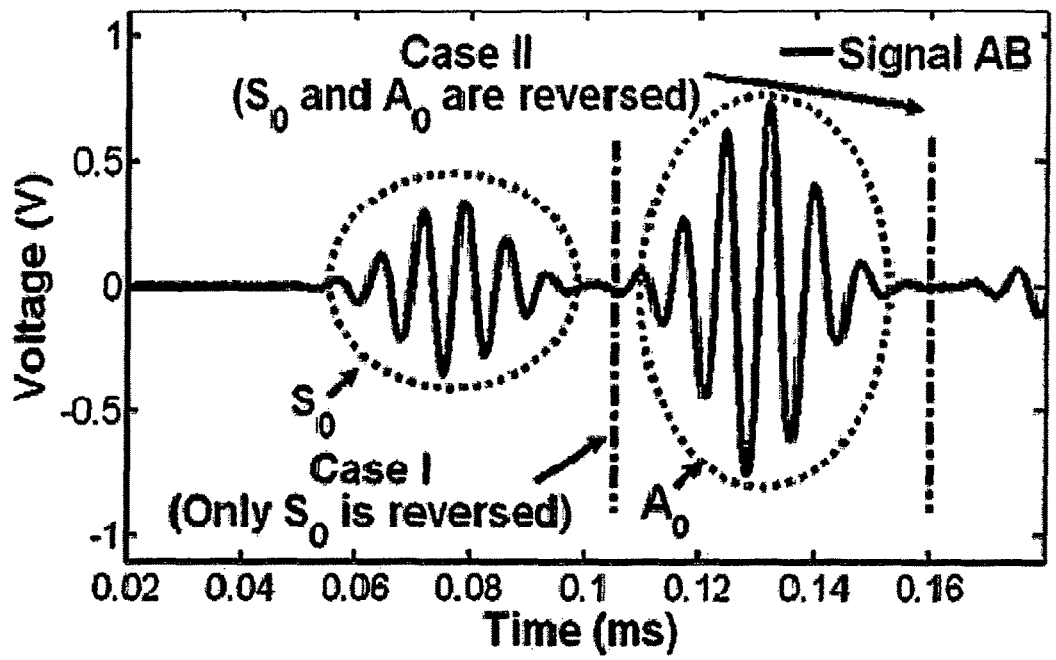
FIGS. 62 and 63 illustrate experimental verification of the multimodal effect by truncating the forwarding signals at different time point for the TRP: Case I truncated right after the $S_0$ mode and Case II after $S_0$ and $A_0$ modes.
Figure 63:
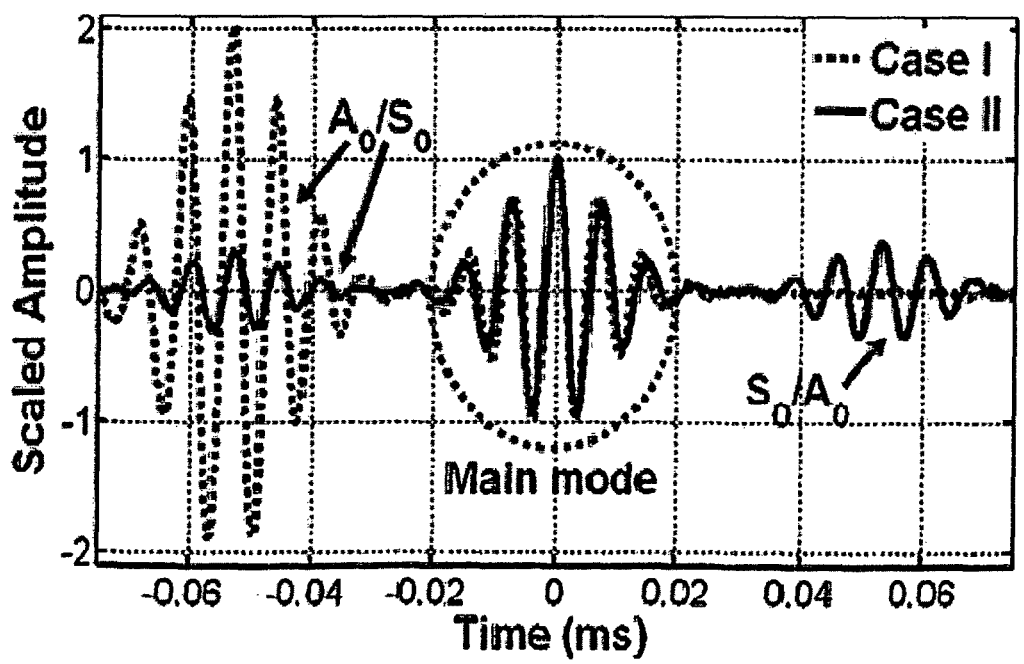

In FIGS. 62 and 63, it is investigated how selective inclusion or exclusion of specific mode(s) affects the reconstructed signal. In Case I shown in FIG. 62, the forwarding signal AB was truncated 0.105 ms after the input signal so that only the $S_0$ mode could be reversed and resent to the original location during the TRP. Because only the $S_0$ mode in the forwarding signal was reversed and applied back to the sensing PZT, the reconstructed signal consisted of only the following two terms.

$$V_R(t) = (\overline{C}^{SS} + \overline{C}^{AA})\overline{\kappa} V_A(T-t) + \overline{C}^{AS}\overline{\kappa} \cos(\overline{\omega} \overline{t}^{AS}) V_A\{T-(t+\overline{t}^{AS})\} \quad (55)$$

In this case, only the $S_0$ mode contributed to the main mode, and there was only one sideband as shown Case I in FIG. 63.

In Case II shown in FIG. 62, the TRP was repeated by truncating the forwarding signal AB at 0.160 ms so that both the $S_0$ and $A_0$ modes could be included during the TRP. In this example, the main mode was composed of the contributions from both the $S_0$ and $A_0$ modes, and two sidebands were created as expected in Eq. (4). Furthermore, the sidebands were symmetric along the main mode as illustrated in Case II in FIG. 63 because $\overline{C}^{SA} = \overline{C}^{AS}$ and $\overline{t}^{SA} = -\overline{t}^{AS}$. Note that the signals corresponding to Cases I and II are scaled in FIG. 63 so that the maximum peak of the main mode is equal to one.

Finally, the time shift value between the main mode and the sidebands were measured experimentally from FIG. 63 and compared with $\overline{t}^{SA}$ value in Eq. (4). To compute $\overline{t}^{SA}$ value, the group velocities of the $S_0$ and $A_0$ modes, 5.316 m/ms, and 3.115 n/ms, were first measured from the arrival times of the $S_0$ and $A_0$ modes in FIG. 62. These values well correspond to the theoretical values estimated from the dispersion curve obtained from the plate properties ($V_S$=5.163 m/ms, $V_A$=3.025 m/ms). Then, the $\overline{t}^{SA}$ value was computed using Eq. (4) ($\overline{t}^{SA}$=0.415.316−0.4/3.115=−0.053 ms). This $\overline{t}^{SA}$ value agreed well with the time gap between the main mode and one of the sidebands observed from FIG. 63 (about 0.0531 ms). Therefore, it is successfully demonstrated that Eq. (3) properly described the sidebands created by multimodes.

According to the above test results, it can be inferred that the shape of the main mode in the reconstructed signal is not affected by the existence of the multimodes, and the multiple Lamb wave modes influence the TRP by generating additional symmetric sidebands. This symmetry of the reconstructed signal is preserved as long as a symmetric input signal is used and both symmetric and anti-symmetric modes are included in the TRP. In the next section, the effect of reflections on the TRP is investigated.

Figure 64:
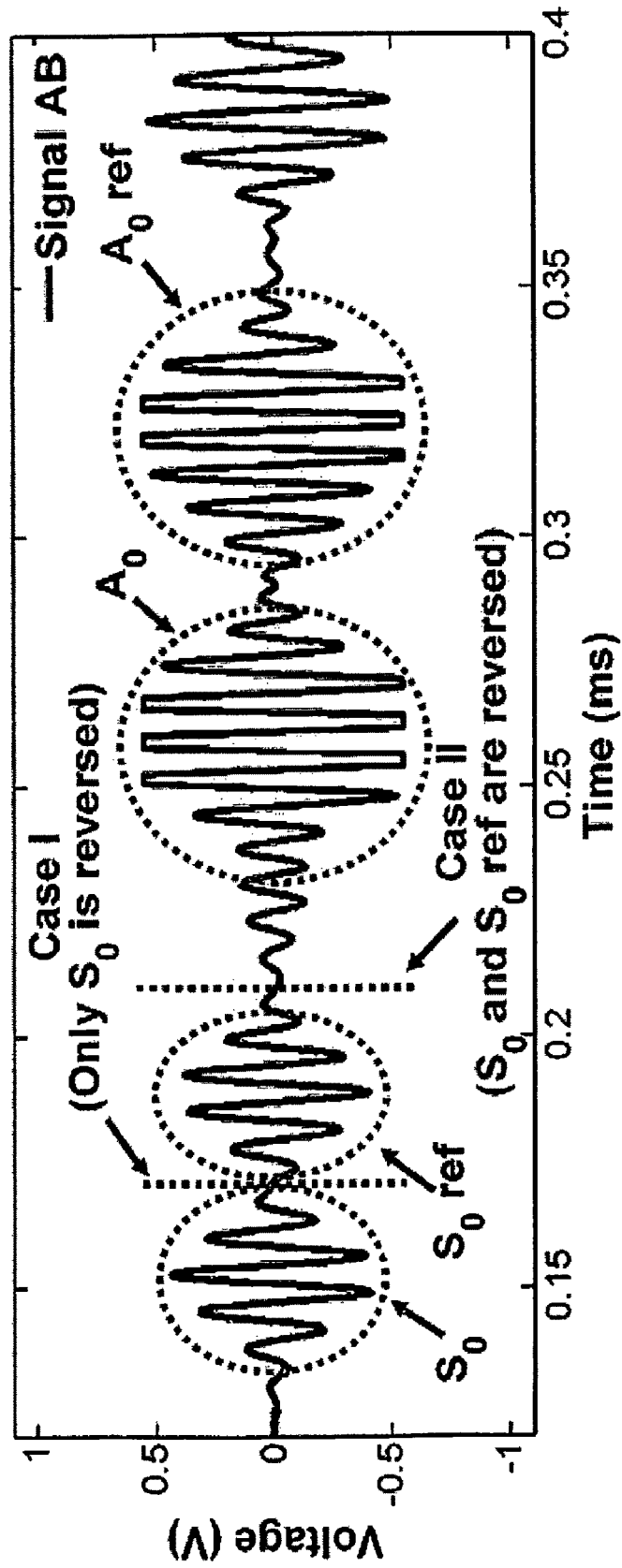
FIGS. 64-66 illustrate experimental investigation of the effect of reflections on the TRP by truncating the forwarding signals at different time points during the TRP: Case I includes only the direct $S_0$ mode and Case II includes the reflected $S_0$ mode as well.

Here, the appearance of the sidebands due to reflections from boundaries and the symmetry of the resulting reconstructed signal were experimentally demonstrated. The test was conducted using a pair of PZT patches attached to the aluminum plate. For the test, two square PZTs with the same size (1.0 cm×1.0 cm) were attached in the middle of the plates. PZT A was mounted 10 cm away from the left side edge of the plate and PZT B was placed 32 cm away from the right side boundary of the plate. In this configuration, multiple Lamb wave modes arrived at PZT B in the following order as shown in FIG. 64: (1) the $S_0$ mode along the shortest (direct) wave path, (2) the $S_0$ mode reflected from the left boundary, and (3) the direct and reflected $A_0$ modes. Because the direct and reflected $A_0$ modes arrived later than the direct and reflected $S_0$ modes, it was possible to truncate the forwarding signal including only the $S_0$ modes to study the effects of the reflections. In FIG. 64, because the resolution of the DIG was set to reduce measurement errors in the direct and reflected $S_0$ modes, the direct and reflected $A_0$ modes which had higher amplitudes than $S_0$ modes were saturated. The exciting frequency of a narrowband tone burst signal, and the LNP gain were set to 130 kHz, and 100, respectively.

Figure 65:
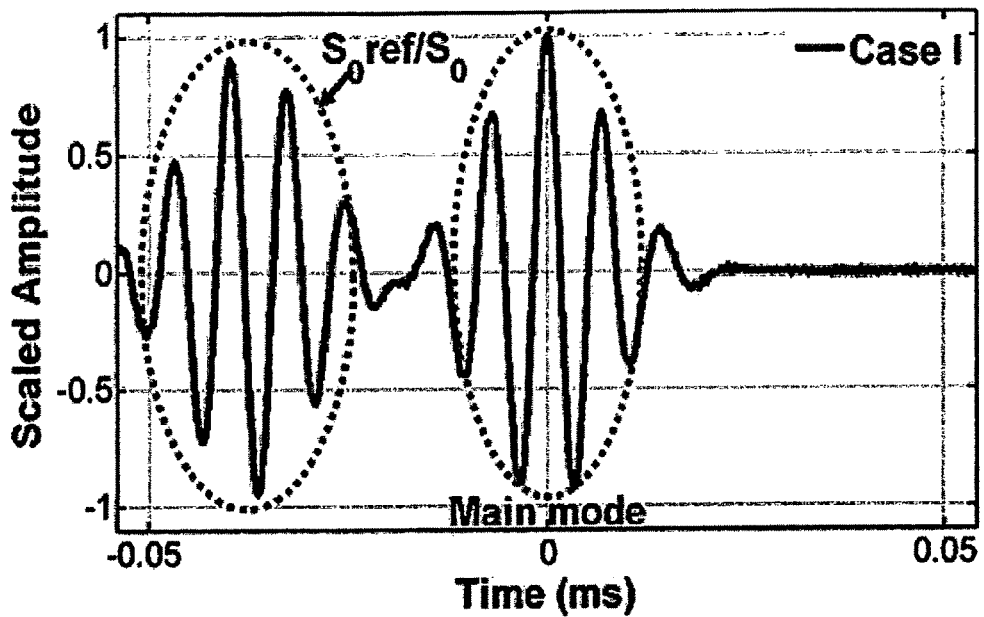
Figure 66:
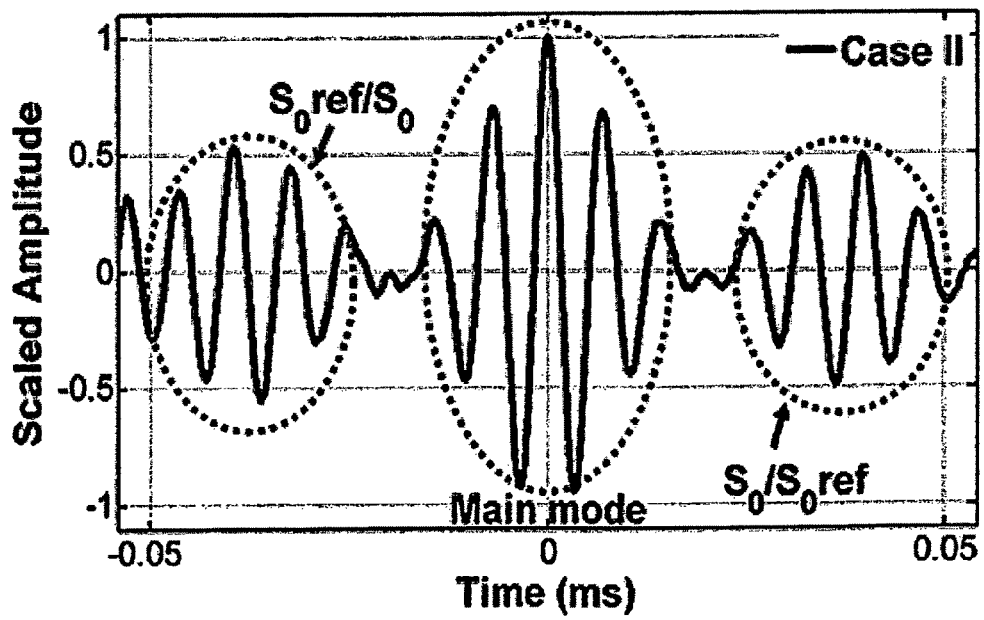

To see the effect of the reflection, the truncation time point in the forwarding signal was varied. First, the forwarding signal in FIG. 64 was truncated at 0.17 ms so that only the direct $S_0$ mode was reversed and resent to the original location (Case I). Next, the truncation was done at 0.2125 ms to embrace both the direct and reflected $S_0$ modes (Case II). In FIGS. 65 and 66, the sidebands created by the reflections are shown. When the TRP was conducted including only the direct $S_0$ mode, a single sideband appeared only on the left hand side of the main mode [FIG. 65]. On the other hand, two symmetric sidebands were developed when both $S_0$ modes were included during the TRP [FIG. 66].

Next, it was investigated if the phase shift of these sidebands matched with the theoretical prediction. Based on the forwarding signal shown in FIG. 64, the group velocity of the $S_0$ mode was measured to be 5.239 m/ms and it was close to the one obtained from the dispersion course in FIG. 64. The arrival time of the right sideband in FIG. 66 was estimated to be 0.0396 ms, and it was close to the $\overline{t}_{DR}$ value obtained from Eq. (7) ($\overline{t}_{DR}=r_D-r_R$)/w($\overline{\omega}$)=(0.80−1.00)/5.239=−0.0382 ms). Furthermore, it must be noted that the shapes of the left and right sidebands were almost symmetrical along the main mode as illustrated in FIG. 66.

From the experiments shown in FIGS. 64-66, the following conclusions were drawn: (1) Although additional sidebands were produced by the existence of reflections, the shape of the reconstructed signal's main mode was hardly affected by the reflections; and (2) The symmetry of the reconstructed signal depended on the truncation point of the forwarding signal and improved as the a longer segment of the forwarding signal was reserved during the TRP.

The present invention will now be described in terms of embodiments utilizing polarization characteristics of piezoelectric materials. These embodiments of the present invention are organized as follows. First, the polarization process of piezoelectric materials is briefly described. Then, the effect of a PZT polarization direction on Lamb wave measurement is investigated, and the proposed reference-free diagnosis technique is developed based on the PZT poling directions. Furthermore, a filtering technique is developed to make the proposed NDT technique less sensitive to variations in PZT size, bonding condition and alignment. Finally, experimental tests as well as numerical simulations are executed to investigate the applicability of the proposed NDT technique to damage detection.

Theoretical Development

Piezoelectric Material and its Polarization Characteristics

Figure 67:
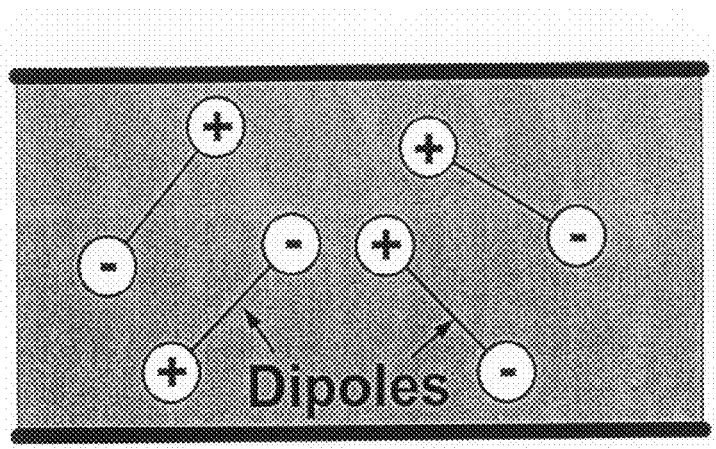
Figure 68:
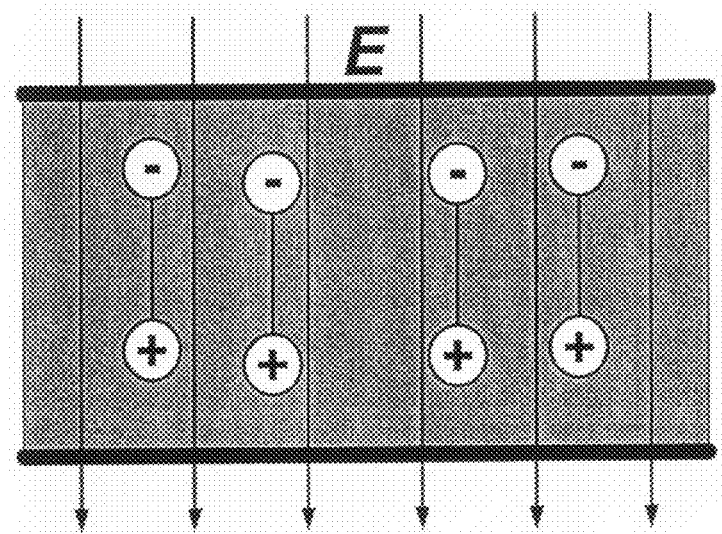
Figure 69:
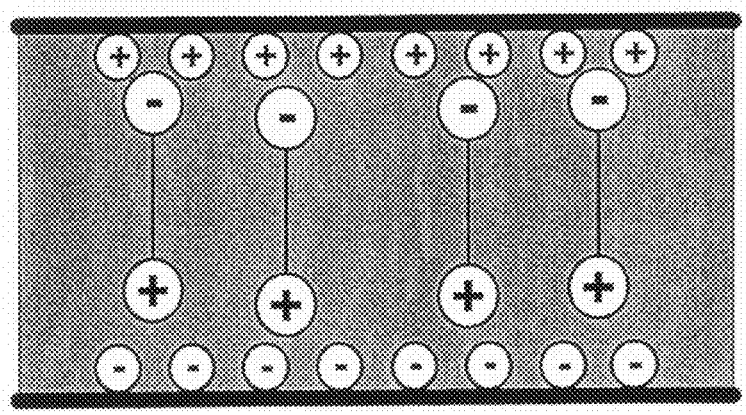

Piezoelectric materials are natural or artificially polarized ceramics which have piezoelectricity. These materials develop an electrical charge or voltage when a mechanical pressure is applied, which is the simplest description of piezoelectricity. Conversely, piezoelectric materials produce deformation (strain) when exposed to an applied electric field. Due to this unique nature of the piezoelectric materials, they are commonly used as both sensors and actuators in many applications. For instance, wafer-type piezoelectric materials such as PZT are commonly used for exciting and measuring guided waves for SHM and NDT applications. In some natural ceramic materials such as quartz, crystal cells, which behave similarly to electric dipoles, are oriented along the crystal axes. However, artificially polarized materials should be poled to have piezoelectricity due to the random orientation of the dipoles at the initial state. In order to force piezoelectricity to the materials, a thermal treatment is commonly utilized. In the first stage, a crystalline material with randomly oriented dipoles is slightly warmed up below its Curie temperature [FIG. 67]. After strong electric field E is applied to the crystalline material, the dipoles in the material align along the field lines [FIG. 68]. Finally, the material is cooled down, and the electric field is removed [FIG. 69]. The polarization of the material is permanently maintained as long as the poled material stays below its Curie temperature. The overall behavior of a piezoelectric material as well as its electrical characteristics is governed by the poling direction of the material. In the next section, the influence of the poling direction on Lamb waves is discussed.

The Effect of PZT Poling Directionality on Lamb Wave Propagation

Figure 70:
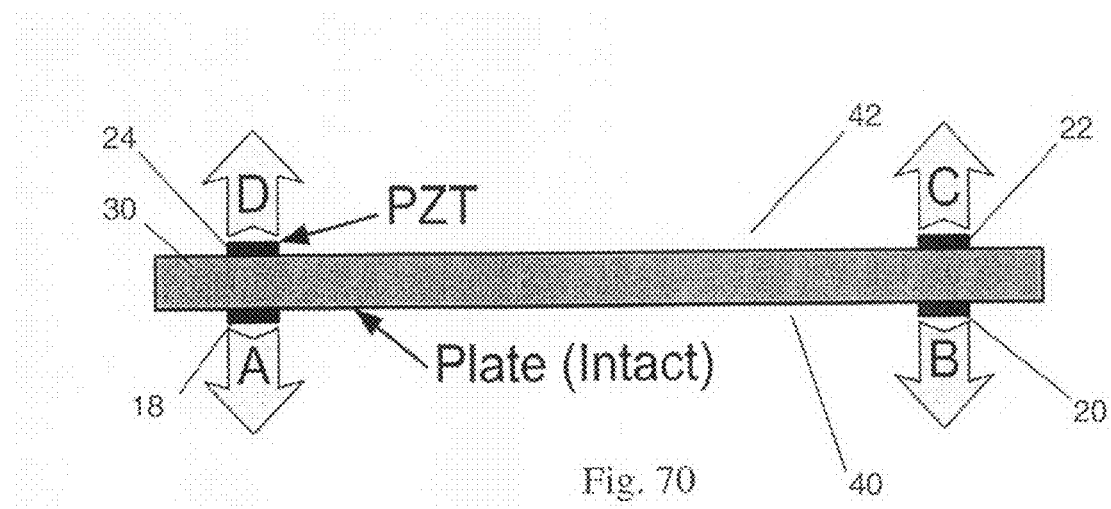

In this section, it is investigated how the phase of a Lamb wave mode changes depending on (1) the poling directions of exciting and sensing PZT wafer transducers and (2) whether a wafer transducer is attached either on the top or bottom surface of a plate. For illustration, it is assumed four identical PZT wafer transducers, labeled as "A", "B", "C, and "D", are attached to a plate as shown in FIG. 70. In this embodiment two of the transducers 18, 20 are on a first surface 40 of the structure 30, and the other two transducers 22, 24 are on an opposite surface 42 of the structure 30. The arrows indicate the positive poling directions of each PZT transducers. PZTs A and D are placed exactly at the same position but on the other side of the plate. PZTs B and C are positioned in a similar fashion. Furthermore, it is assumed that a narrowband tone burst is applied as an input signal, and the driving frequency is chosen such that only the fundamental symmetric ($S_0$) and anti-symmetric ($A_0$) modes are generated.

Figure 71:
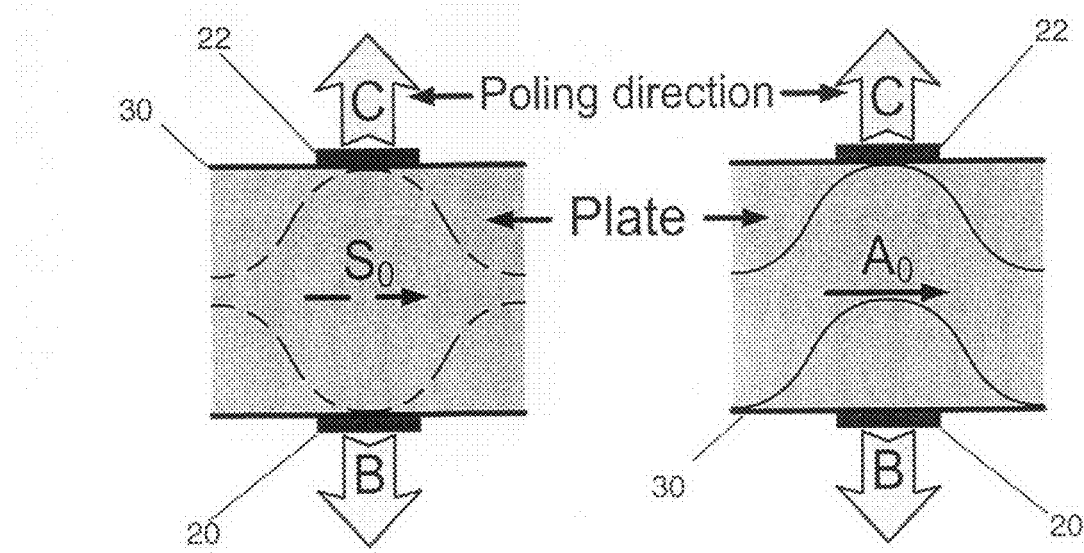
Figure 72:
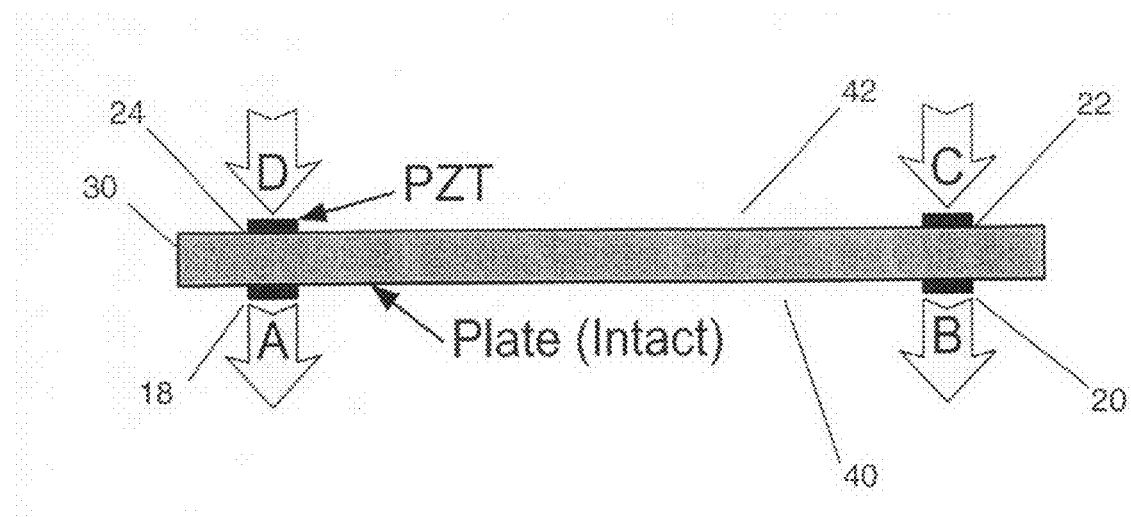
Figure 73:
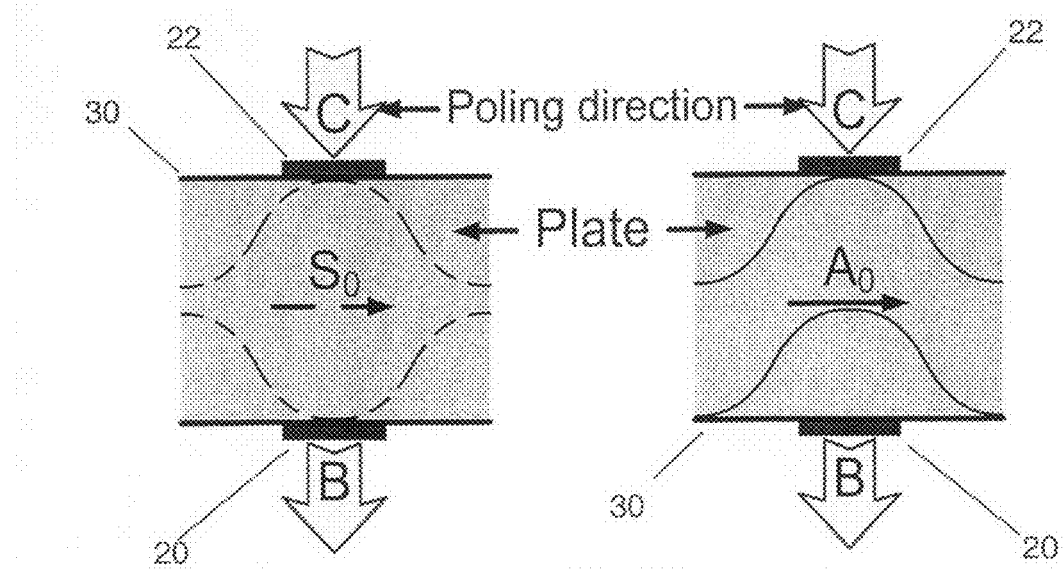
Figure 74:
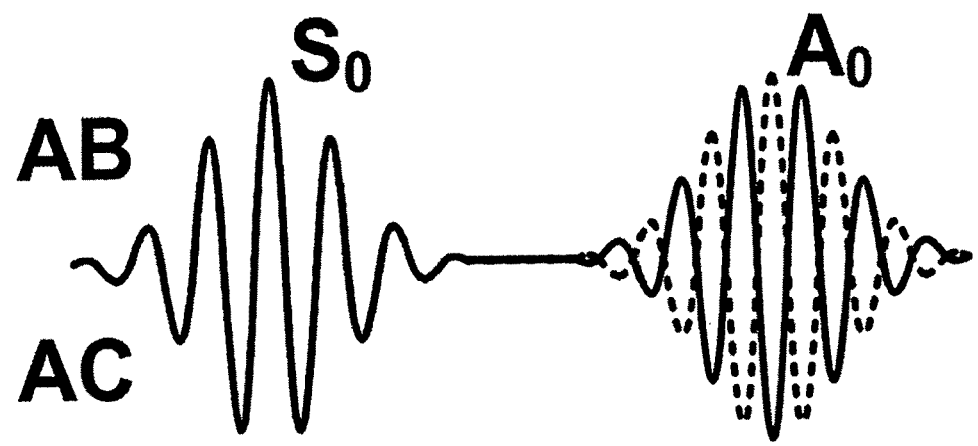
Figure 75:
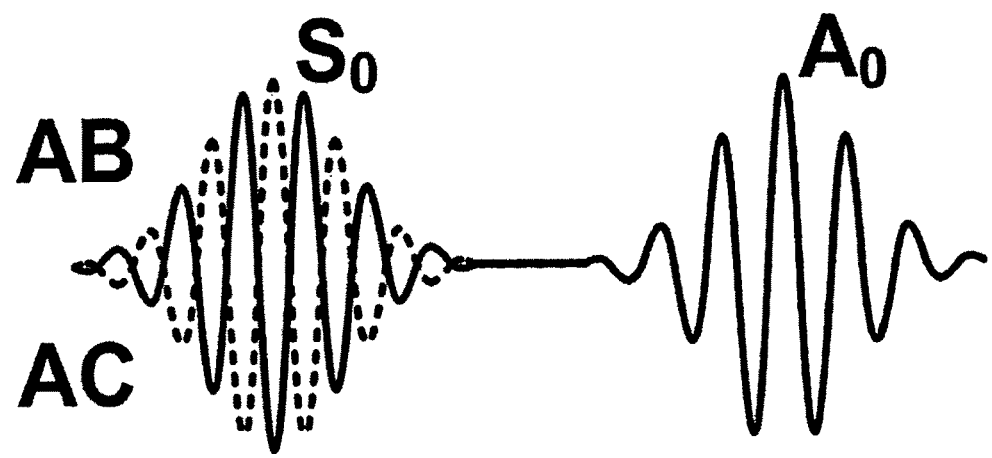

When PZT A is excited, the $S_0$ and $A_0$ modes are generated and measured at PZTs B and C. In an ideal condition, the amplitude and arrival time of the $S_0$ mode measured at PZTs B and C should be identical. In addition, both PZTs B and C should be subjected to positive bending because of the symmetric nature of the $S_0$ mode (See the figure on the left in FIG. 71). (In the present application, this term of "positive bending" is used when the positively polarized side of the PZT is subjected to tensile strain. On the other hand, the PZT is subjected to negative bending when the negatively polarized size of the PZT is subjected to tensile strain. The positive bending produces a "positive" output voltage while the negative bending results in a "negative" output voltage value.) Because both PZTs B and C are subject to the positive bending, the phase of the $S_0$ mode measured at these PZTs are identical as well as the amplitude and arrival time (See the $S_0$ mode in FIG. 74). As far as the $A_0$ mode is concerned, PZT B is subjected to the negative bending although PZT C still undergoes the positive bending (See the figure on the right in FIG. 71). Therefore, the $A_0$ modes measured at PZTs B and C are out-of-phase (See the $A_0$ mode in FIG. 74). However, when the poling direction of the PZT C is switched [FIG. 72], PZTs B and C will produce out-of-phase $S_0$ modes and in-phase $A_0$ modes [FIG. 73 and FIG. 75].

This idea of using the PZT poling directionality in Lamb wave propagation is not a completely new idea. However, the majority of the past work has focused on selective generation of $S_0$ and $A_0$ modes [Su Z. and Ye L. (2004) Selective generation of Lamb wave modes and their propagation characteristics in defective composite laminates, Proceedings of the Institution of Mechanical Engineers, Part L: Journal of Materials: Design and Applications, Vol. 218, No. 2, pp. 95-110]. For instance, by exciting PZTs A and D shown in FIG. 70 in-phase, only the $S_0$ mode can be excited. In this invention, the polarization characteristic of the PZT is utilized not only for selective generations of Lamb wave modes but also for selective measurements. In the following section, this concept is further advanced so that the mode conversion due to damage formation can be extracted from the measured Lamb wave signals.

Figure 76:
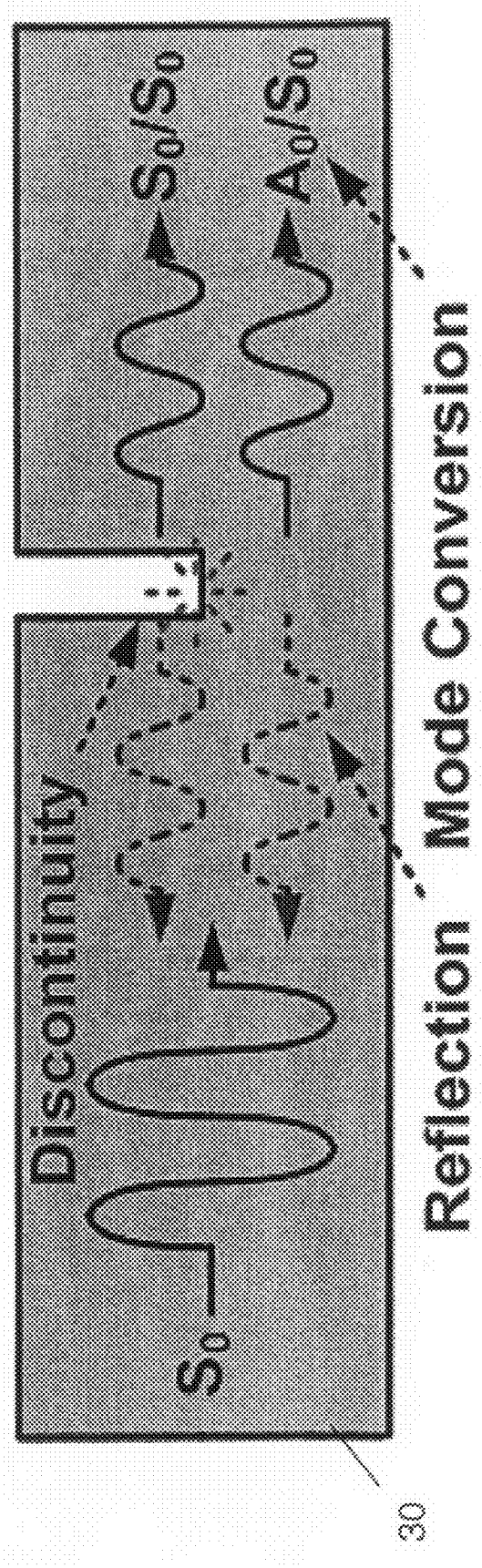
FIG. 76 illustrates a schematic diagram of mode conversion and reflection due to a discontinuity on a plate.

Extracting Mode Conversed Signals Due to Crack Damage Using a PZT Poling Direction In this subsection, the PZT polarization characteristic is further advanced so that the mode conversion due to crack formation can be detected without using any prior baseline data. First, the effect of a crack on Lamb wave modes is described. If Lamb waves propagating along a thin plate encounter a discontinuity, some portion of the waves are reflected at the discontinuity point and others are transmitted through it. When a $S_0$ mode arrives at the notch as shown in FIG. 76, it is separated into $S_0$ and $A_0$ modes (denoted as $S_0/S_0$ and $A_0/S_0$, respectively). In a similar manner, an $A_0$ mode is also divided into $S_0$ and $A_0$ modes ($S_0/A_0$, and $A_0/A_0$). This phenomenon is called mode conversion.

Figure 78:
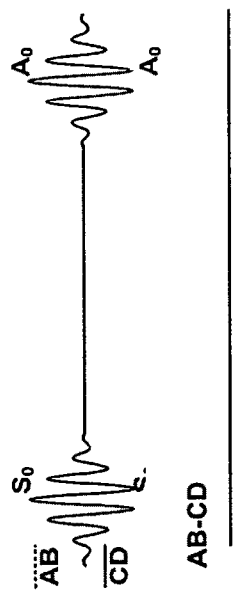
Figure 80:
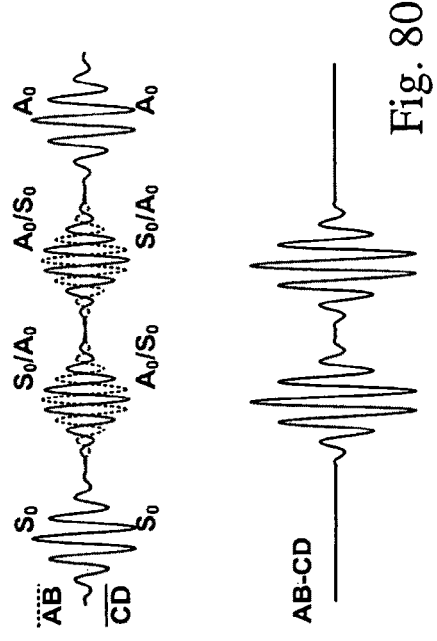
Figure 77:
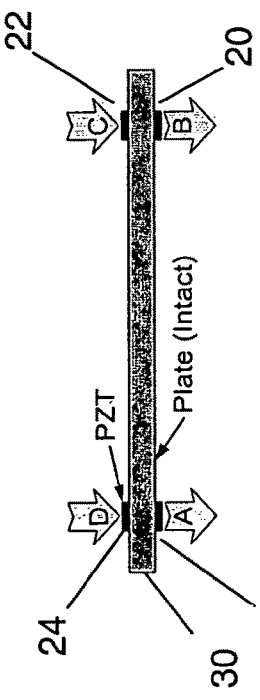
Figure 79:
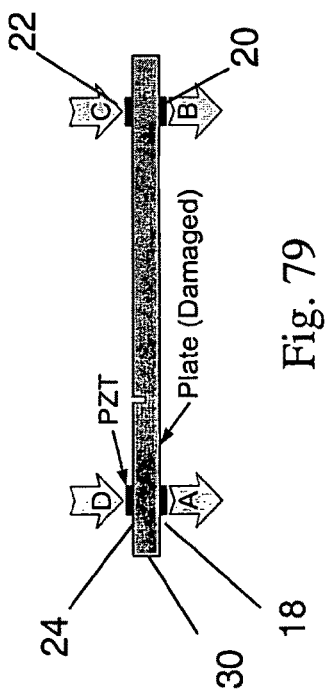
Figure 81:
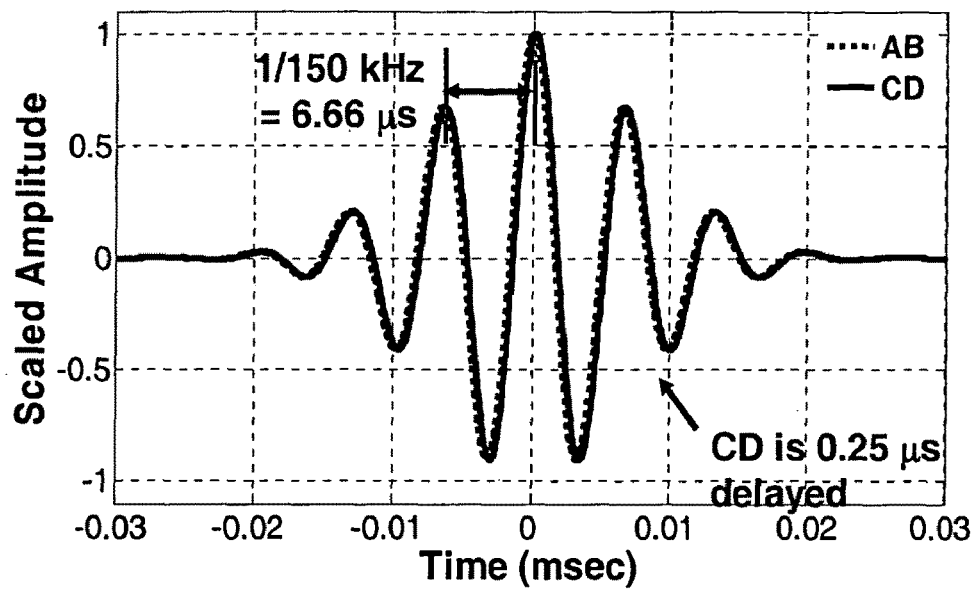

When the plate is in a pristine condition and four identical PZTs are instrumented as shown in FIG. 77, it can be shown that a signal AB becomes identical to a signal CD as illustrated in FIG. 78. Here, the signal AB denotes the response signal measured at PZT B when the excitation is applied at PZT A, and the signal CD is defined in a similar fashion. However, the signal AB is no longer identical to the signal CD [FIGS. 79 and 80] when there is a crack between PZTs A and B (or PZTs C and D). As for the signal AB, the $S_0/A_0$ mode arrives at PZT B earlier than the $A_0/S_0$ mode when the notch is located closer to PZT A than PZT B (assuming that the $S_0$ mode travels faster than the $A_0$ mode). Conversely, the $S_0/A_0$ mode arrives at PZT D later than the $A_0/S_0$ mode in the case of the signal CD. In FIG. 80, the signals AB and CD are drawn considering not only the arrival time of each mode but also the poling directions of the PZTs.

Note that, while the $S_0$ and $A_0$ modes in FIG. 80 are in-phase, the $S_0/A_0$ and $A_0/S_0$ modes in the signals AB and CD are fully out-of-phase. Therefore, the additional modes generated by a notch can be extracted simply by subtracting the signal AB from the signal CD as shown in FIG. 80. Because this approach relies only on comparison of two signals obtained at the current state of the system rather than comparison with previously recorded reference data, it is expected that this approach reduces false alarms of defects due to changing operational and environmental variations of the system. For instance, it can be readily shown that temperature change of the system does not affect this approach.

Development of a Filter Technique to Address Variations in PZT Size, Alignment and Bonding Condition In the previous subsection, it is shown that the signals AB and CD are indistinguishable when there is no crack [FIG. 78]. This is based on the assumption that all PZT transducers are identical and PZTs A and D (or PZTs B and C) are perfectly collocated. In practice, these assumptions can not be fully satisfied because of variations in PZT size, alignment and bonding condition. Therefore, residual differences would remain after subtracting the two signals even at the absence of crack, and this could be a source of positive false alarms. To tackle this practical implementation issue, a filtering technique is developed in this subsection.

The development of this signal processing technique is based on the observation that the additional modes generated by a crack are out-of-phase while the other modes are in-phase when signals AB and CD are compared [FIG. 80]. According to FIG. 80, because $S_0$ modes and $A_0$ modes in signals AB and CD are in-phase, the point by point product (PPP) values between not only $S_0$ modes but also $A_0$ modes are always positive. On the other hand, the PPP between $S_0/A_0$ ($A_0/S_0$) in the signal AB and $A_0/S_0$ ($S_0/A_0$) in the signal CD produces negative values. Therefore, the existence of a crack can be detected by observing the negative PPP values between the signals AB and CD. Then, it is investigated how the PPP values are affected by variations in PZT size, alignment and bonding condition. The main effects of the non-ideal PZTs on the signals AB and CD can be summarized as the amplitude change of the response signals and the time shifting of one signal with respect to the other. For instance, the debonding and/or cracking of PZT A can reduce the coupling area between PZT A and the substrate and consequently decrease the amplitude of the signal AB with respect to the signal CD. It can be readily shown that this pure amplitude change does not alter the negative PPP values to the positive values and vice versa. However, the variations in PZT size, alignment and bonding condition can also cause phase shifting, and this requires a special treatment.

Figure 82:
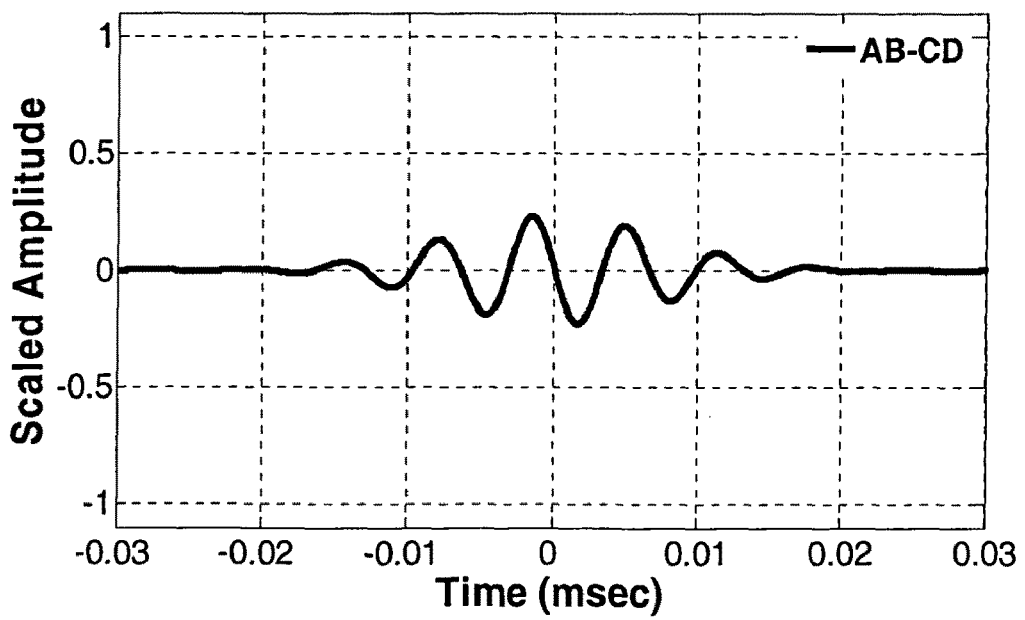

In FIGS. 81-85, an example of the phase shift caused by PZT transducer misalignment is illustrated. The results shown in FIGS. 81-85 are obtained from the same configuration shown in FIG. 72 except that PZT C is shifted 0.76 mm to the right with respect to PZT B. That is, the distance between PZTs A and B becomes 0.76 mm shorter than the distance between PZTs C and D. Due to this misalignment, the $A_0$ mode in the signal CD is delayed about 0.25 μs with respect to the $A_0$ mode in the signal AB (0.76 mm/3.055 mm/μs=0.25 μs) [FIG. 81]. Because the $A_0$ mode travels slower than the $S_0$ mode at 150 kHz ($V_S$=5.088 mm/μs, $V_A$=3.055 mm/μs), the $A_0$ mode is more severely affected by the misalignment than the $S_0$ mode. Therefore, the discussion here focuses on the delay of $A_0$ modes. Furthermore, note that 0.76 mm misalignment is equivalent to 8% of the 10 mm×10 mm PZT wafer transducer size. Although 0.25 μs may be considered a small time delay, FIG. 82 shows that this time delay produces a substantial difference between the signals AB and CD when they are subtracted from each other.

Figure 83:
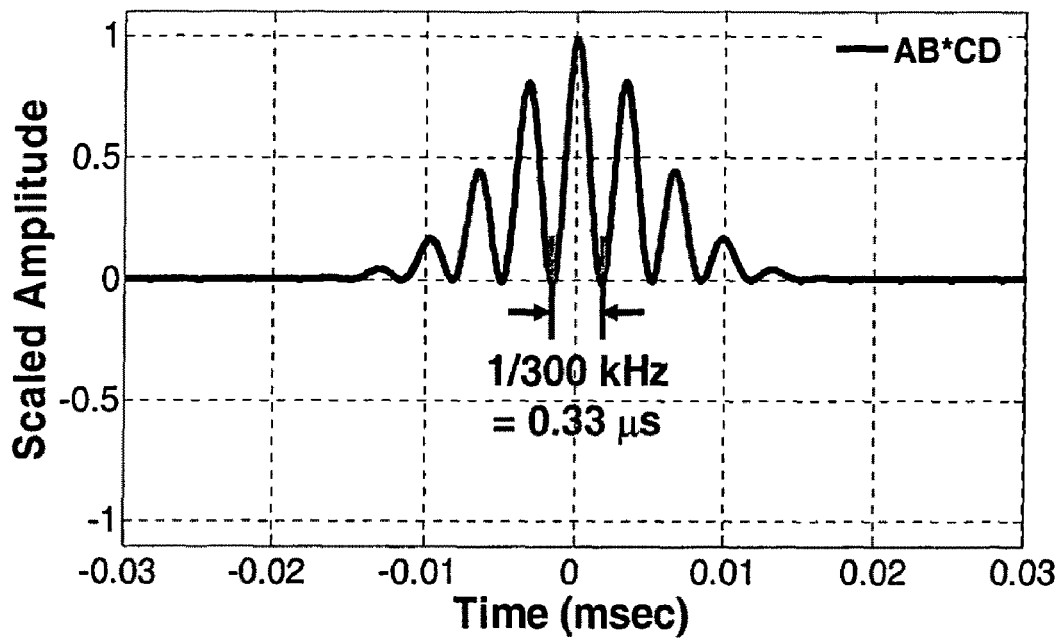
Figure 84:
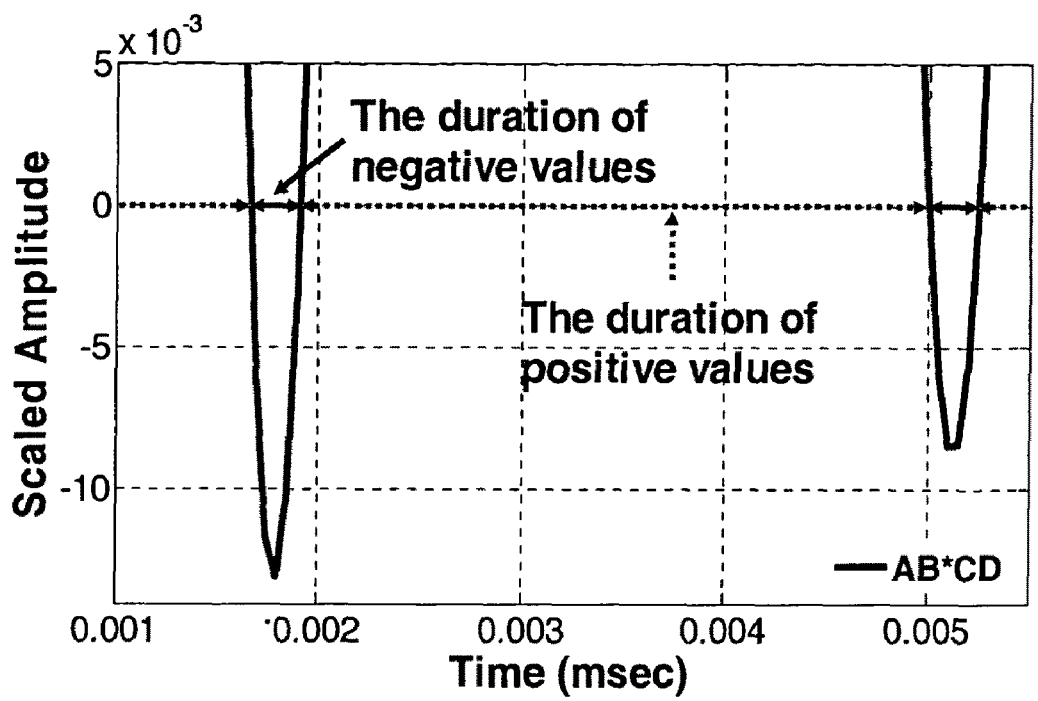
Figure 85:
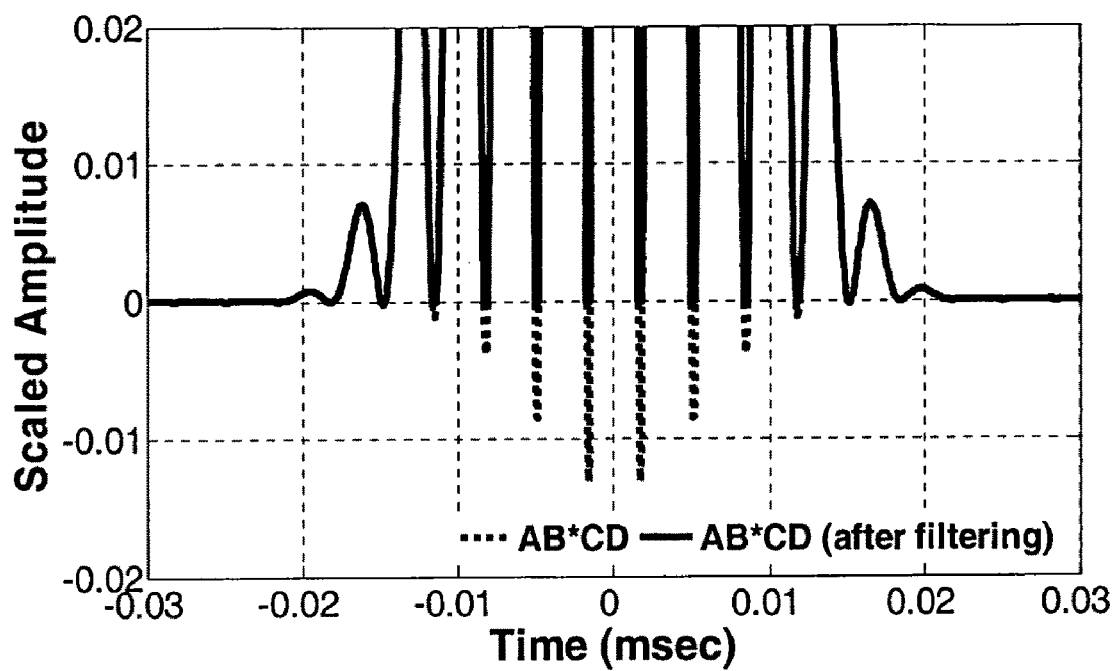

On the other hand, FIG. 83 shows that the PPP values between the signals AB and CD are mostly positive except at a few negative points. The negative PPP values are the results of the misalignment and amplified in FIG. 84. It can be analytically shown that the PPP between the two signals at 150 kHz produces a 300 kHz frequency component as shown in FIG. 83. Therefore, the time period of the PPP values becomes 3.33 μs (=1/300 kHz). The observation of FIG. 84 further reveals that the duration of the negative PPP values is shorter than that of the positive PPP values. For instance, 3 mm misalignment, which is equivalent to 30% misalignment in a 10 mm×10 mm PZT wafer transducer, produces 0.98 μs (=3 mm/3.055 mm/μs) duration of the negative PPP values. Note that the mode conversion also produces negative PPP values. However, the duration of the negative PPP values caused by the mode conversion becomes 2.35 μs (=3.33 μs−0.98 μs) in this configuration. Therefore, the duration of the negative PPP values due to the mode conversion remains longer than the duration caused by PZT misalignment as long as the PZT misalignment is controlled under certain precision. In this paper, it is assumed that the PZT misalignment can be controlled under 30% of the 10 mm×10 mm PZT transducer size and this misalignment produces 0.98 μs duration of the negative PPT values. Then, the effect of the misalignment is eliminated by removing the negative PPP values, whose duration is less than 0.98 μs [FIG. 85]. The effectiveness of this filtering technique is further investigated in the following numerical studies.

Numerical Simulation

Figure 86:
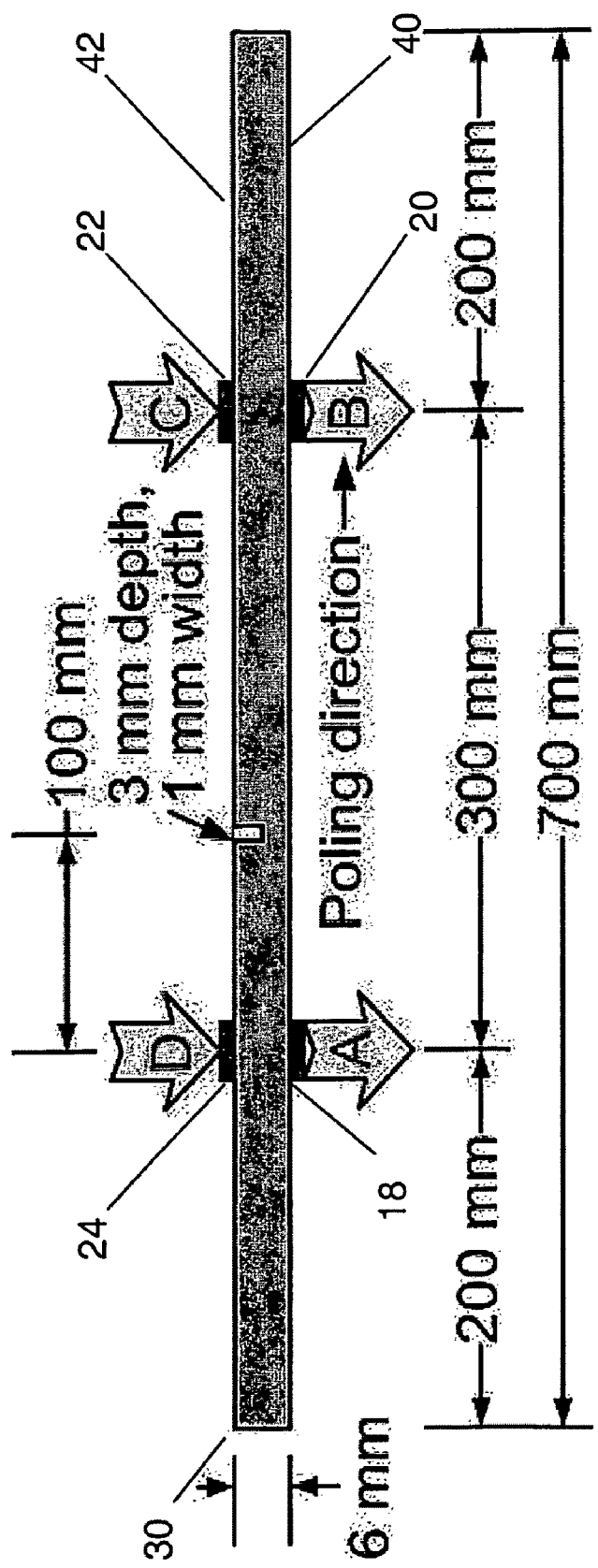

The idea of using a PZT poling direction for crack detection was first validated by numerical simulation. Using COMSOL Multiphysics software (www.comsol.com), Lamb wave propagation in a two dimensional aluminum beam was simulated using the combination of plain strain, piezo plain strain, and electrostatics modules in COMSOL software. The length of the beam was 70 cm, and its thickness was 6 mm. Four identical PZTs with a size of 10 mm×10 mm×0.508 mm were attached to the beam model as shown in FIG. 86. Note that PZTs A and D were collocated but on the other side of the beam with the same poling direction. PZTs B and C were placed in a similar fashion. The parameter values used in the numerical simulation are listed in Table 11. A narrowband tone-burst signal at 150 kHz frequency was used as an input signal. In the simulation, Rayleigh damping coefficients were set to $10^{-4}$ for a mass damping coefficient and 0 for a stiffness damping coefficient, respectively. The simulation results were obtained from a time dependent solver, and a time step was set to 0.25 μs, which is equivalent to 4 M samples/sec. To control the error in each integration step, relative tolerance and absolute tolerance for the solution were chosen to be $10^{-3}$ and $10^{-10}$, respectively. The maximum backward differentiation formula (BDF) order for setting the degree of the interpolating polynomials in the time-stepping method was set to order 2. Finally, the model was meshed using a mapped mesh option, and the size of each mesh was limited to 1 mm×1 mm. (COMSOL AB. (2005) COMSOL Multiphysics User's Guide, Version 3.2.)

Figure 87:
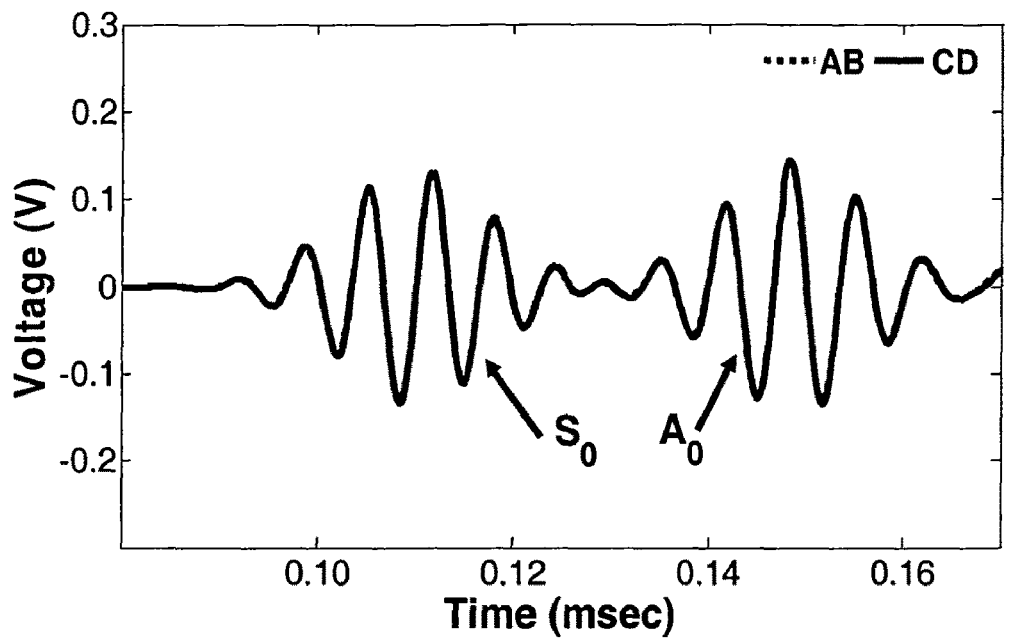
Figure 88:
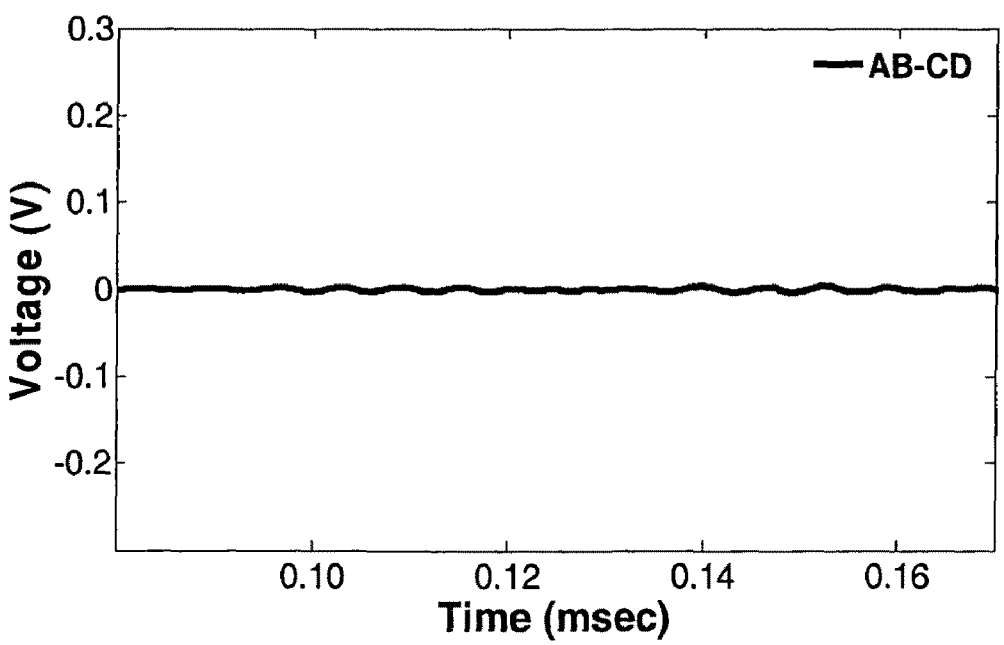
Figure 89:
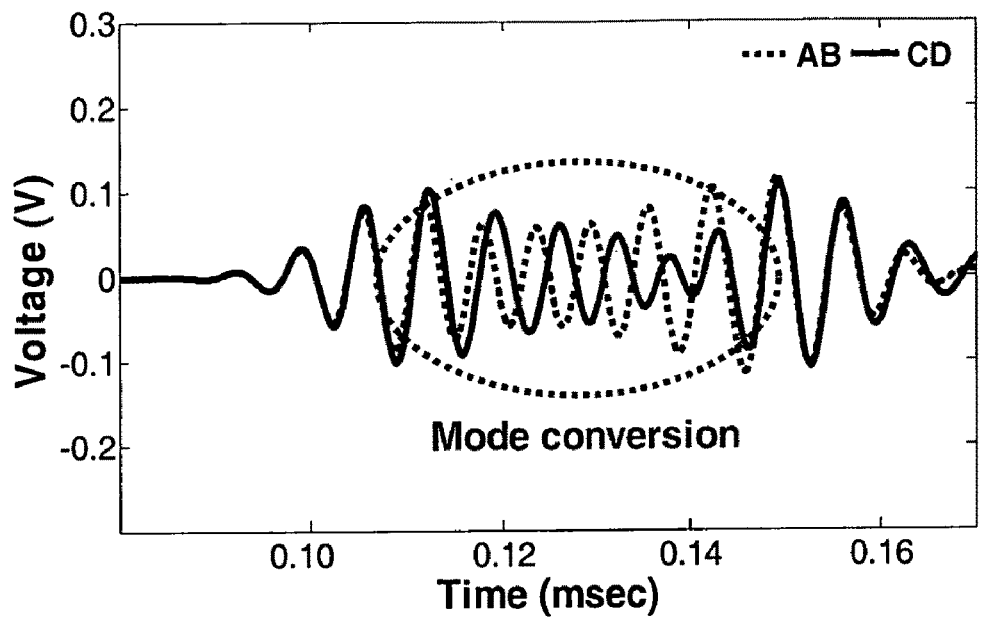
Figure 90:
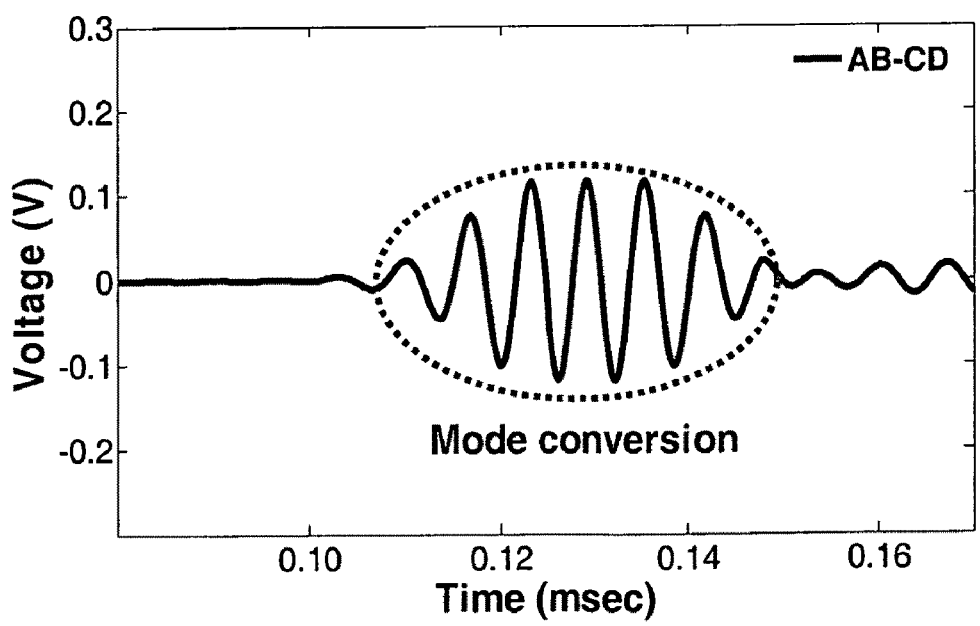

FIGS. 87-88 illustrate that signals AB and CD were almost identical and this well corresponds to the theoretical expectation. Once a notch of 3 mm depth and 1 mm width was introduced 100 mm away from PZT D toward PZT C, the signal AB became different from the signal CD as a result of the mode conversion induced by the crack [FIG. 89]. The mode conversion due to cracking was extracted simply by subtracting the signal CD from the signal AB [FIG. 90].

TABLE 11

| Parameters used in numerical simulation | |
| --- | --- |
| Exciting frequency | 150 kHz |
| α (Mass damping coeff.) | $10^{-4}$ |
| β (Stiffness damping coeff.) | 0 |
| Sampling rate | 4 Ms/s |
| Relative tolerance | $10^{-3}$ |
| Absolute tolerance | $10^{-10}$ |
| Maximum BDF order | 2 |
| Mesh size (mapped mesh) | 1 mm × 1 mm max. |

Figure 91:
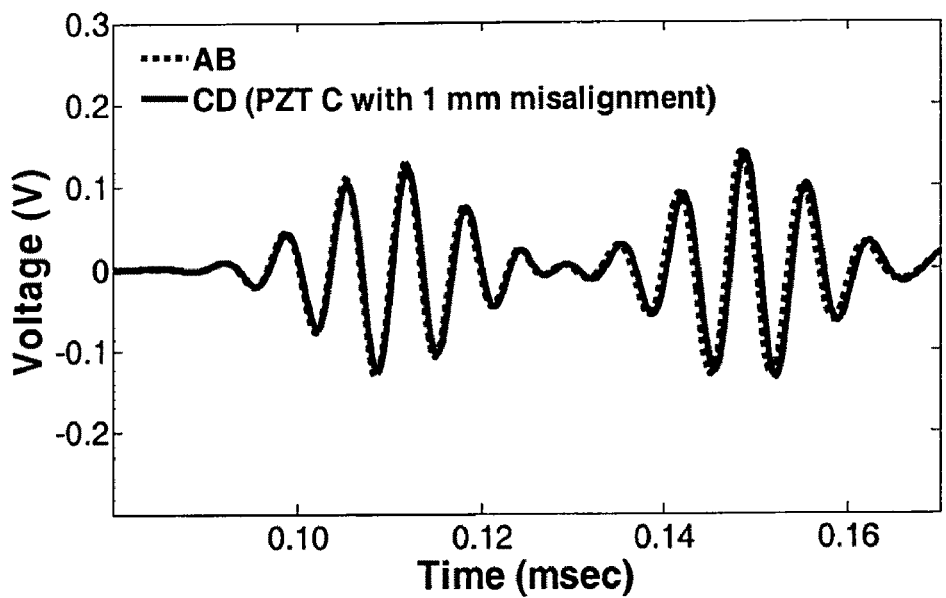
Figure 92:
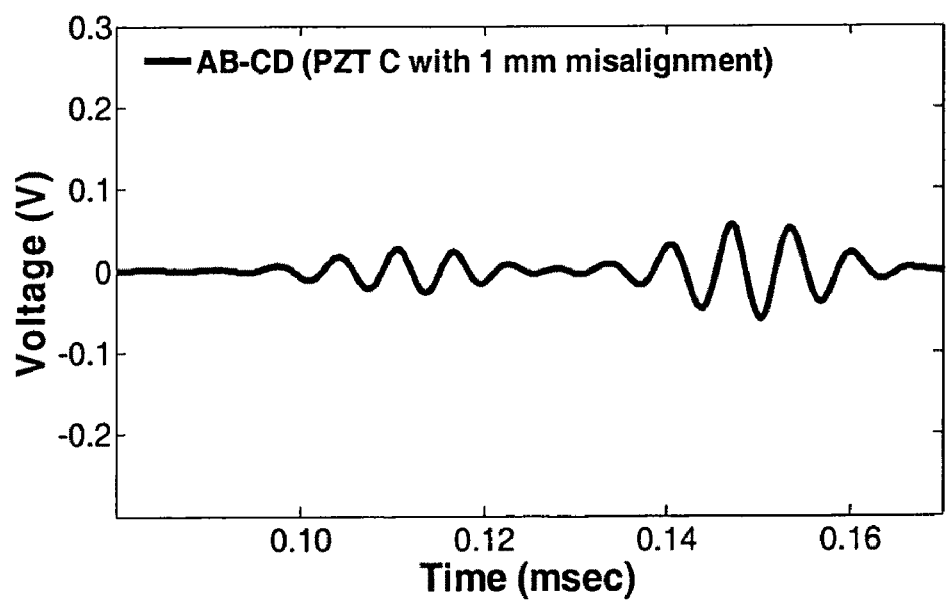
Figure 93:
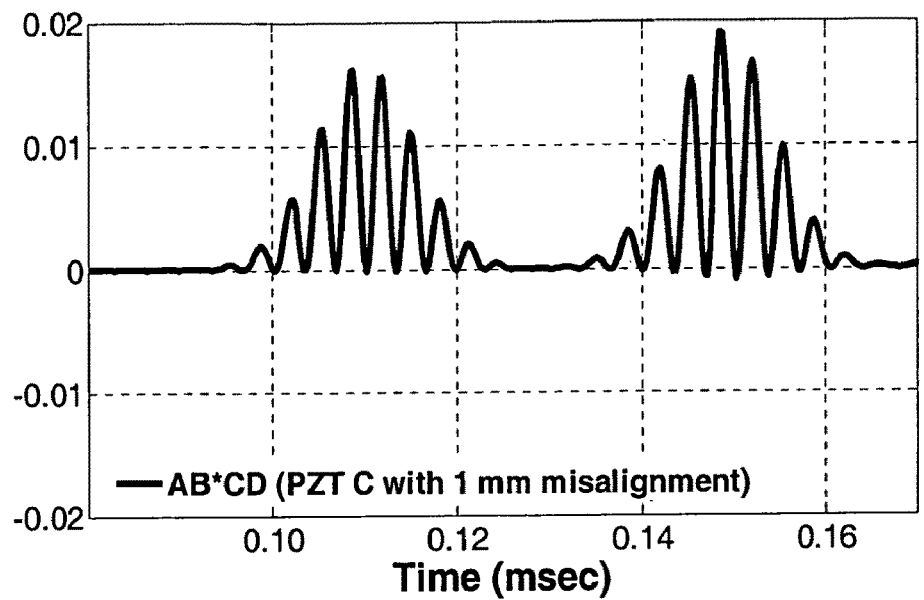
Figure 94:
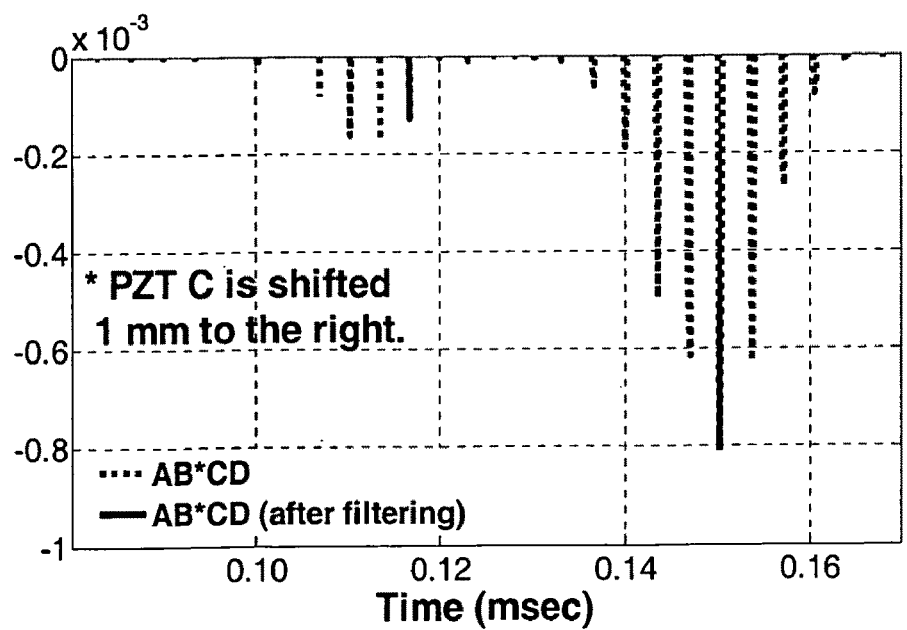

So far it has been assumed that all PZTs are identical, and two PZTs on the both sides of the beam are precisely collocated. In practice, the size, bonding condition and electrical impedance of a PZT transducer will vary from one device to another, and there can be PZT misalignment. To investigate the effectiveness of the proposed filtering techniques for addressing these practical implementation issues, the previous numerical simulation was repeated after introducing misalignment between PZTs B and C: PZT C was shifted 1 mm to the right with respect to PZT B. Although the shapes of the signals AB and CD were almost identical as shown in FIG. 91, their subtraction produced residuals, whose amplitudes were much higher compared to the one in FIG. 88 [FIG. 92]. FIG. 93 shows the PPP values between the signals AB and CD, and the negative PPP values were magnified in FIG. 94. By determining the duration of the negative PPP values and removing negative values whose duration is less than the threshold value (0.98 μs defined in the section entitled "Development of a filter technique to address variations in PZT size, alignment and bonding condition"), the effect of the PZT misalignment was removed in FIG. 94.

Figure 95:
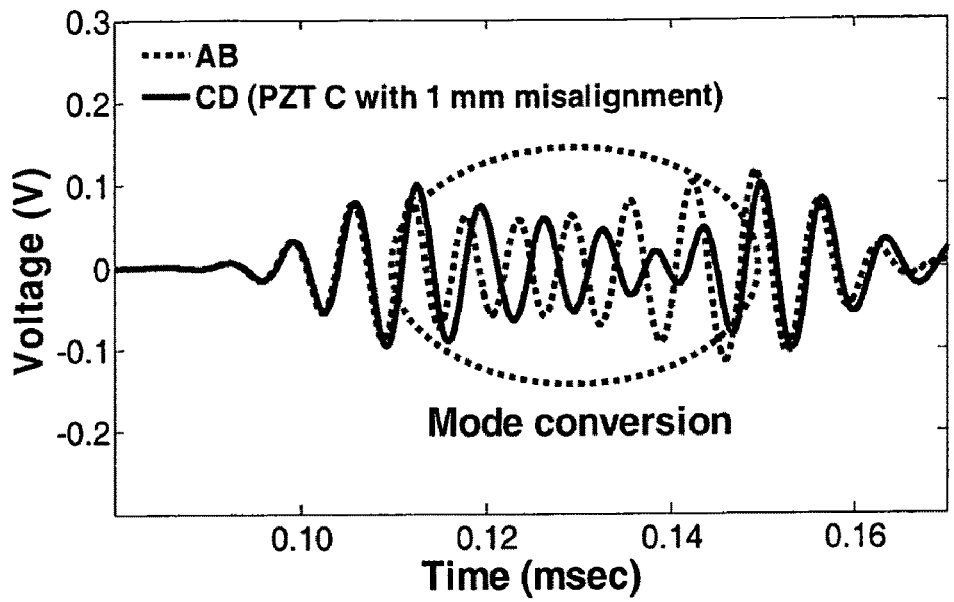
Figure 96:
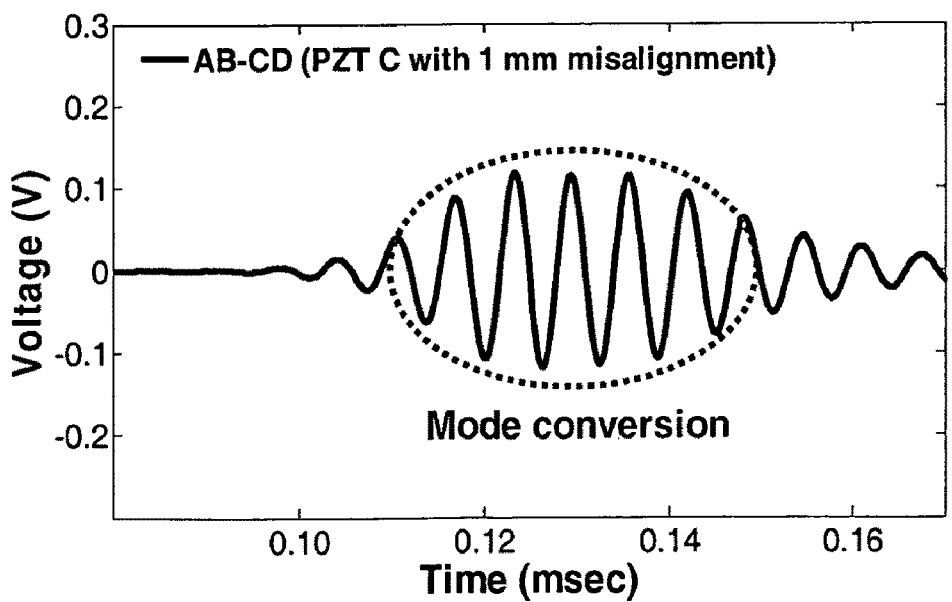
Figure 97:
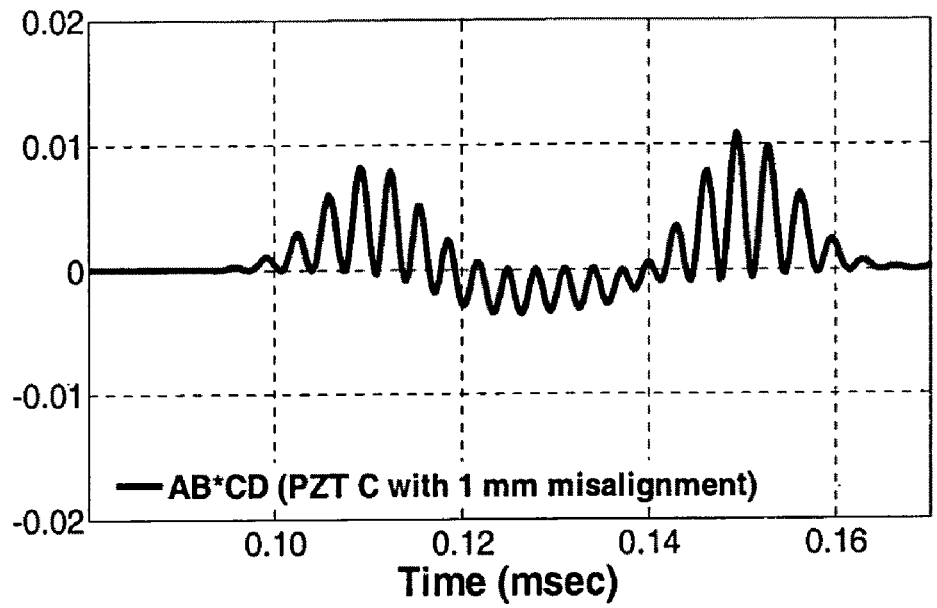
Figure 98:
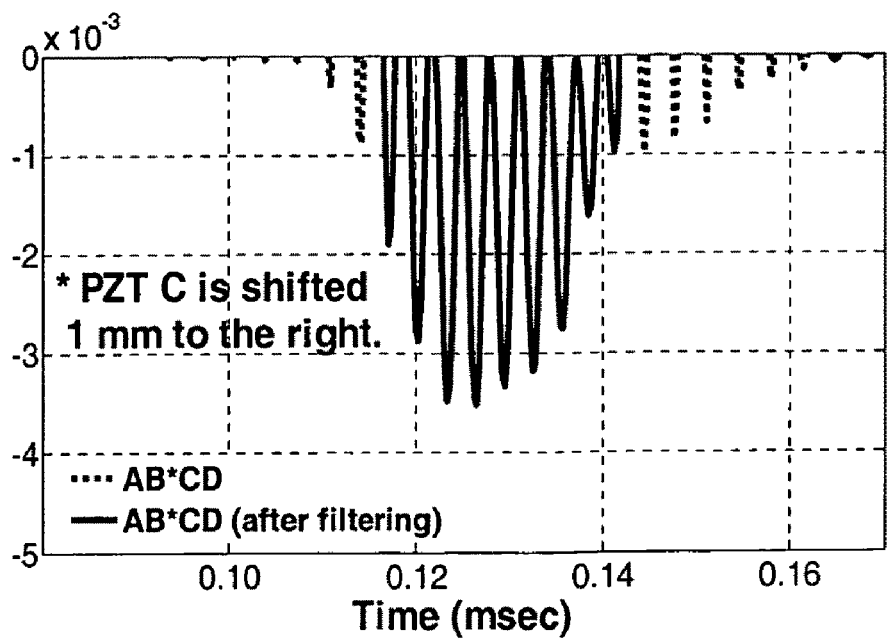

In FIG. 95, the numerical simulation was repeated again with a crack introduced at 100 mm away from PZT A toward PZT B as well as the PZT misalignment. Subtracting the signals AB from the CD produced the residual signal shown in FIG. 96. Without relying on prior baseline data, it is challenging to determine whether this remaining signal appears due to mode conversion or sensor misalignment. However, by calculating the PPP between signals AB and CD and applying the proposed filtering technique, the mode conversion due to crack was extracted as shown in FIGS. 97 and 98). This numerical example demonstrates that crack can be identified even when there is PZT transducer misalignment. This finding is further substantiated in the following experimental study.

Experimental Results

Description of Experimental Setup

Figure 99:
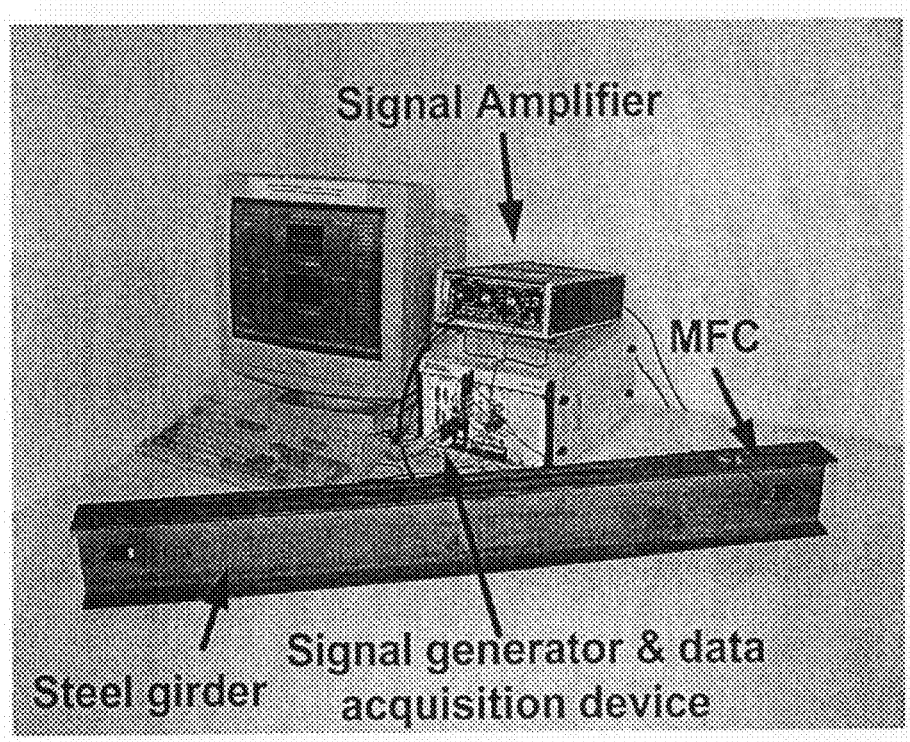
Figure 100:
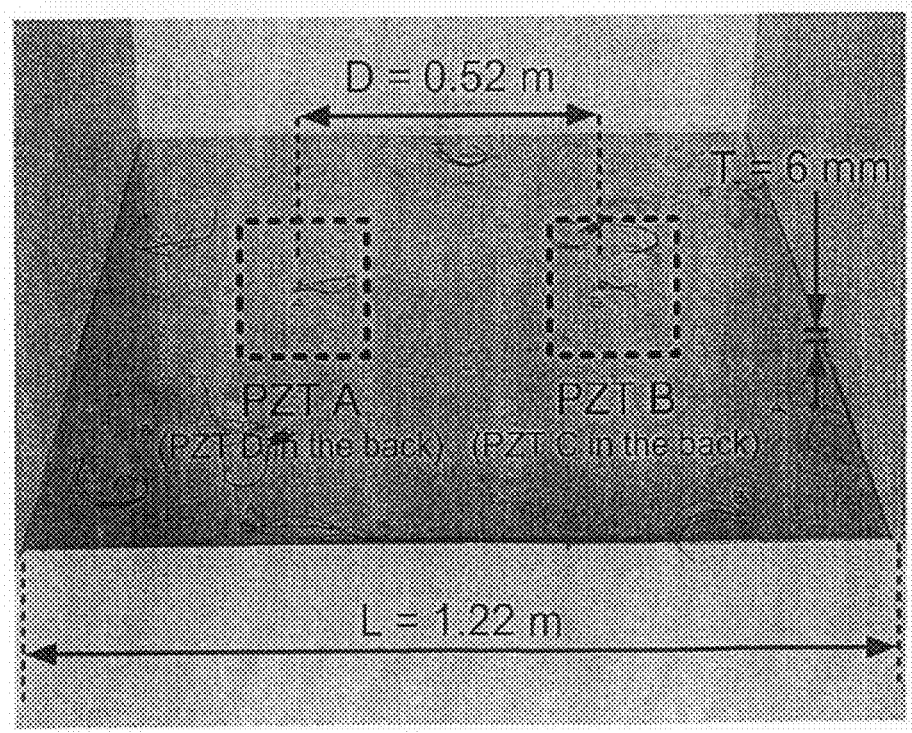

To further examine the proposed reference-free NDT technique, experimental tests have been conducted on an aluminum plate. The overall test configuration of the experiment and the test specimen are shown in FIGS. 99 and 100. The data acquisition system was composed of an arbitrary signal generator (AWG), a high-speed signal digitizer (DIG), a low noise preamplifier (LNP) and a multiplexer. The dimension of the plate was 122 cm×122 cm×0.6 cm, and four PSI-5A4E type PZT wafer transducers (1.0 cm×1.0 cm×0.0508 cm) were mounted in the middle of the plate. PZTs A and D were collocated and attached on the other side of the plate, and PZTs B and C were mounted in a similar fashion. The PZTs were attached so that their poling directions were identical to the configuration shown in FIG. 72. PZTs A and B (or PZTs C and D) were 0.52 m apart each other. In this experiment, the PZT transducers were attached to either the top or the bottom surface of the plate with commercial cyanoacrylate adhesive.

Using the 14-bit AWG, a tone-burst signal with a ±10 peak-to-peak voltage and a driving frequency of 150 kHz was generated and applied. First, PZT A in FIG. 100 was excited by this input waveform. Then, PZT A generated elastic waves and the response was measured at PZT B. When the waves arrived at PZT B, the voltage output from PZT B was amplified by the LNP with a gain of twenty and measured by the DIG. The sampling rate and resolution of the DIG were 20 MS/sec and 16 bits, respectively. In order to increase signal-to-noise ratio, the forwarding signals were measured twenty times and averaged. After the forwarding signal from PZT A to PZT B (signal AB) was measured, the same process was repeated by exciting PZT C and measuring response at PZT D (signal CD). Finally, the PPP values of signals AB and CD were calculated, and the negative PPP values due to sensor misalignment were selectively removed. The entire experimental process without averaging signals took less than 15 seconds. Detailed test results are described in the next section.

Crack Detection Using the Reference-Free NDT Technique Based on the PZT Polarization Characteristics.

Figure 101:
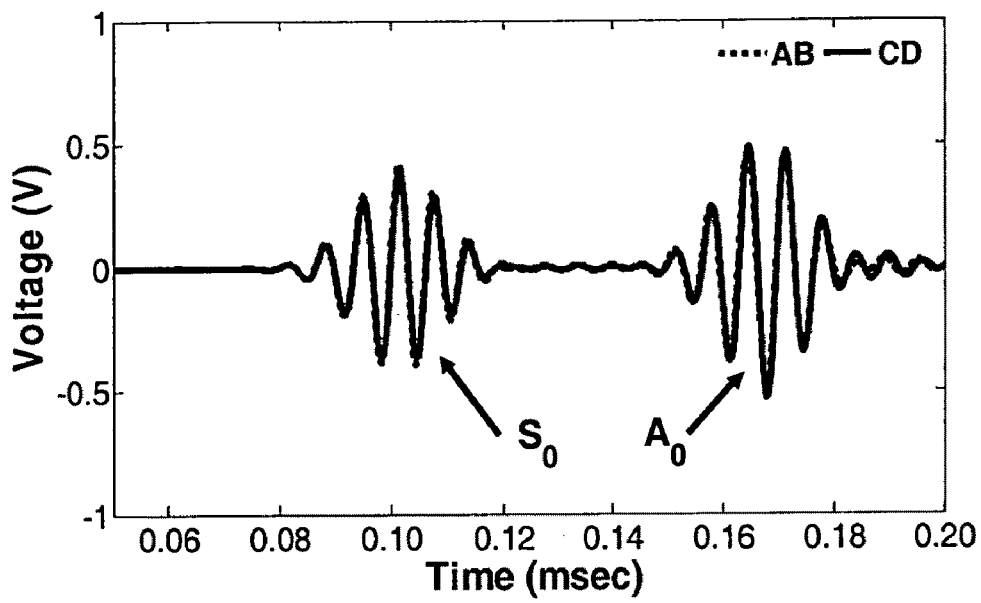

In FIG. 101, Lamb wave signals obtained from an intact plate are presented. Using the test setup described in the previous section, signals AB and CD were measured. Although the signal AB was supposed to be identical to the signal CD, a residual signal was observed in FIG. 102 due to imperfections in PZT alignment, size and bonding condition.

Figure 102:
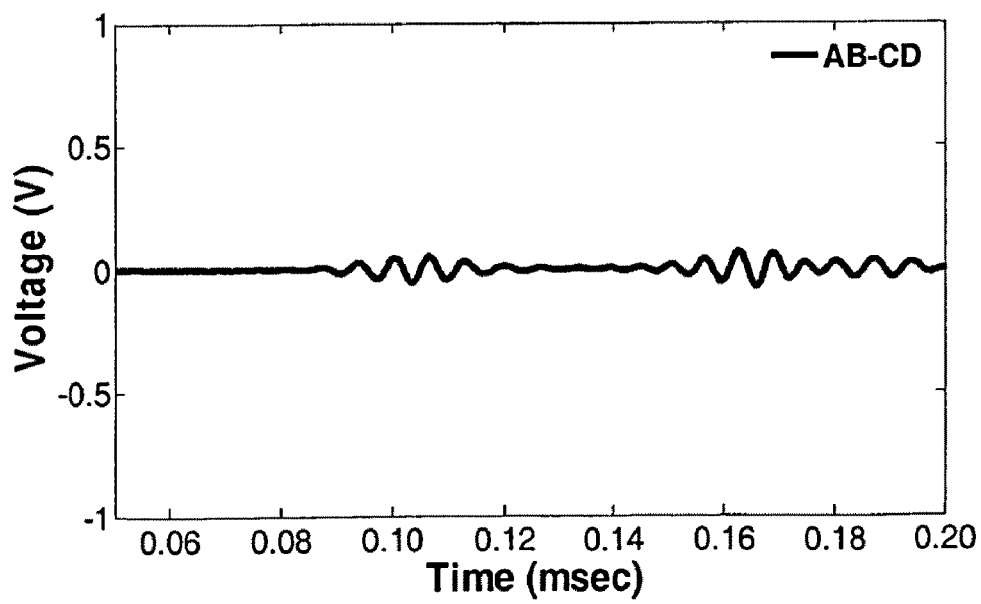
Figure 103:
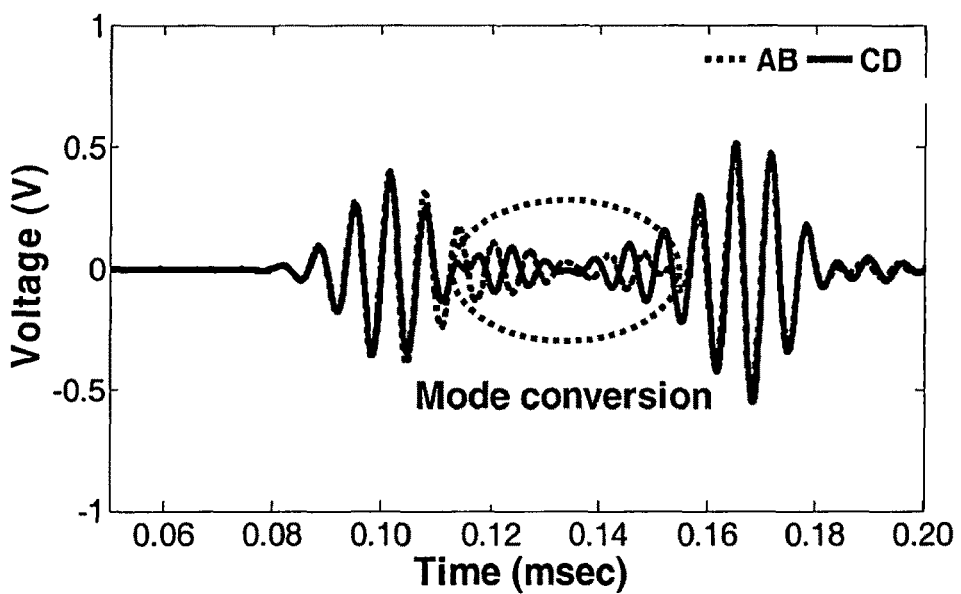
Figure 104:
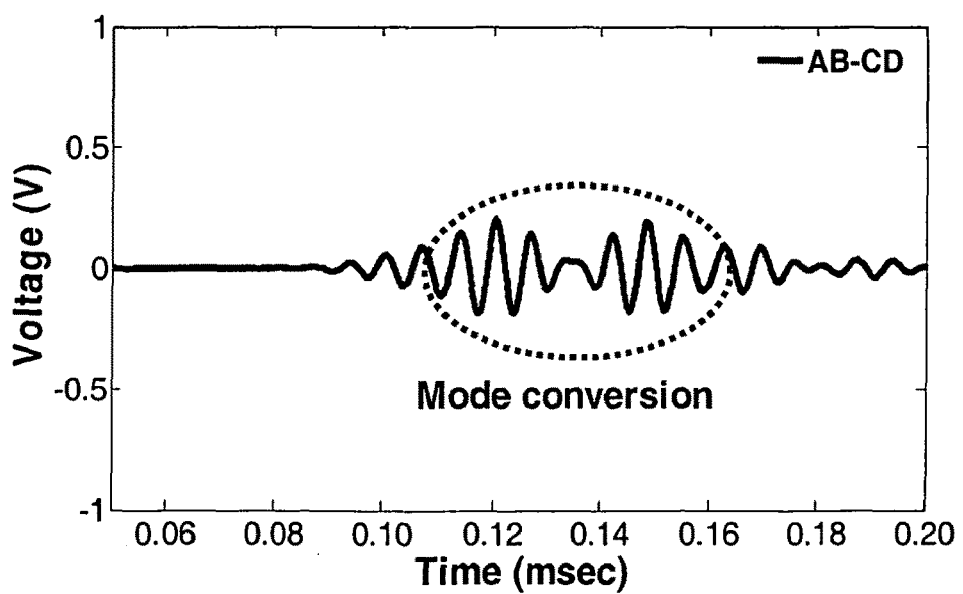
Figure 105:
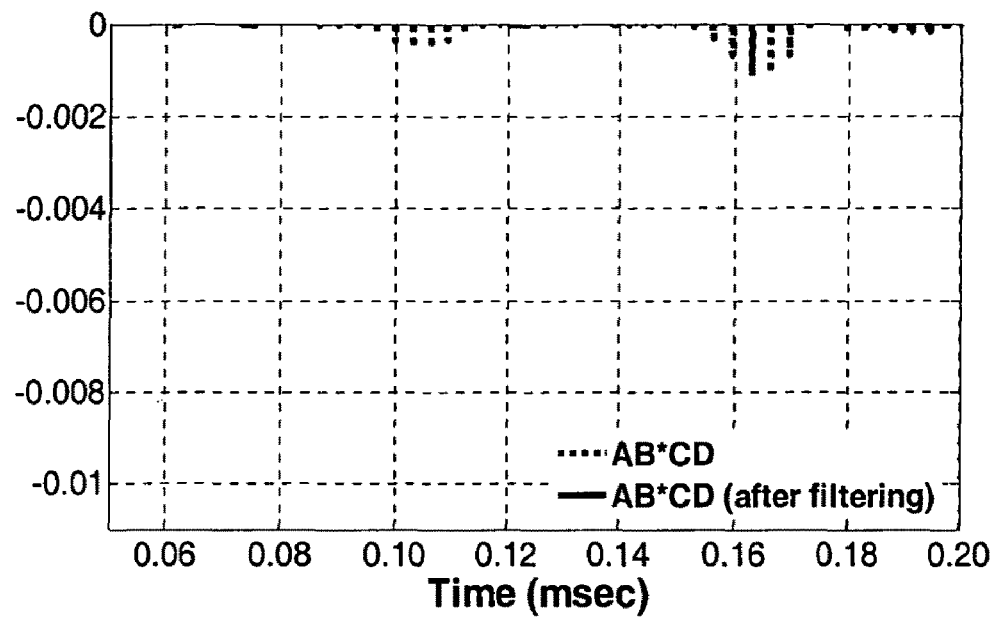
Figure 106:
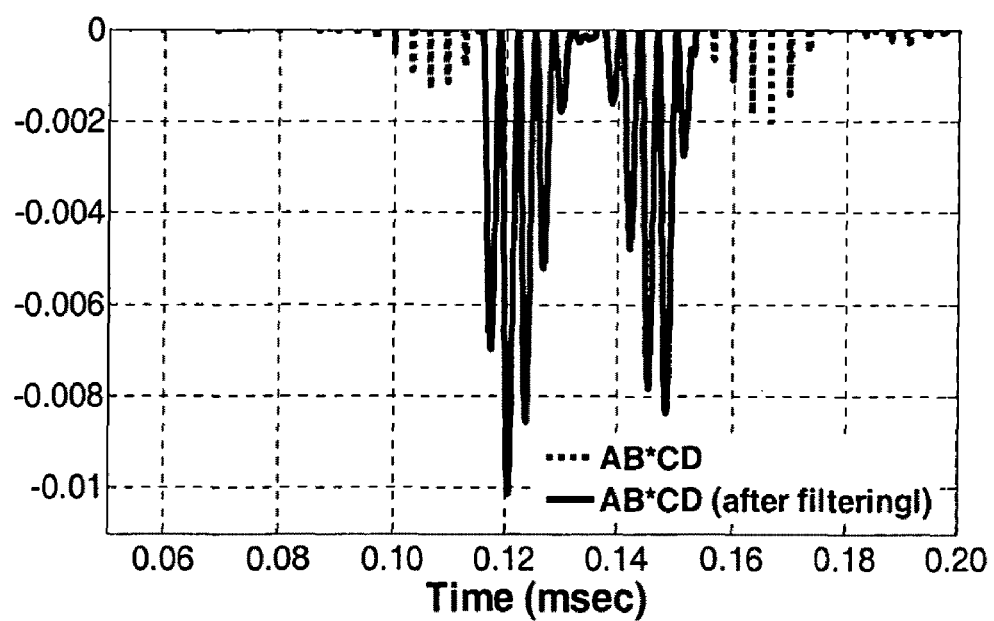

Next, a 3 mm (depth)×1 mm (width)×60 mm (length) notch was introduced between PZTs A and B (or PZTs C and D). The notch was located 150 mm away from PZT A toward PZT B. As a consequence, two additional modes due to the mode conversion appeared between the existing $S_0$ and $A_0$ modes as shown in FIG. 103. Comparison of FIG. 102 and FIG. 104 shows the mode conversion effect on the difference between the signals AB and CD. Then, the proposed filtering technique was applied to the PPP values between the signals AB and CD before and after introducing crack. Using the proposed filtering technique, the negative PPP values resulted from the mode conversion were retained while the negative values associated with the sensor misalignment were selectively removed. As shown in FIG. 105, the negative PPP values between signals AB and CD was negligible at the absence of a notch. Once the notch was introduced, the effect of the two additional modes clearly appeared as shown in FIG. 106. The arrival times of these two additional modes correspond well to the theoretical calculation.

Note that possible locations of the notch can be estimated by measuring the arrival times of two additional modes in signals AB and CD. According to the signal AB in FIG. 101, the velocity of the $S_0$ and $A_0$ modes were estimated to be 5.128 m/ms and 3.099 n/ms (theoretically, $V_S$=5.088 m/ms and $V_A$=3.055 m/ms), respectively. The location of a notch is closer to PZT A than PZT B when the $S_0/A_0$ mode ($S_0$ converted from $A_0$) arrives earlier than the $A_0/S_0$ mode ($A_0$ converted from $S_0$). Conversely, when the $A_0/S_0$ arrives earlier than the $S_0/A_0$, the notch is close to B. However, it is impossible to determine whether the first arrived mode conversed signal is $S_0/A_0$ or $A_0/S_0$ in signals AB and CD because both $S_0/A_0$ mode and $A_0/S_0$ modes are in-phase in the signal AB and are out-of-phase in the signal CD [FIG. 80]. Therefore, two possible notch locations are determined assuming that the location can be closer to either the PZT A or the PZT B. Assuming the notch is closer to the PZT A, the distance from A to the notch can be estimated using Eq. (56) based on a velocity-distance relationship:

$$\text{The arrival time of the first mode conversed signal} = \frac{s}{V_a} + \frac{\text{Distance between } PZT\ A \text{ and } PZT\ B - s}{V_s} \quad (56)$$

where $V_a$, $V_s$, and $s$ denote the velocity of $A_0$ mode, the velocity of $S_0$ mode, and the distance of notch from A, respectively. By observing the arrival time of the first mode (0.1206 ms) and using Eq. (56), the two possible locations of the notch were estimated to be at 15.034 cm away from PZT A or PZT B. This estimated distance was almost identical to the actual distance (0.2% difference) from the PZTs. Here, two notch locations are indicated using an AB and CD combination. It is also possible that the exact notch location can be determined including other signals such as a signal AC and a signal BD. For instance, the signals AB and AC have out-of-phase $S_0/A_0$ signals and in-phase $A_0/S_0$ signals. Therefore, from the negative PPP values between signals AB and AC, the arrival time of the $S_0/A_0$ signal can be determined. Once the arrival time of $S_0/A_0$ is known, whether the notch is close to PZT A or PZT B can be decided that the exact damage location is finally estimated.

Summary

A new concept of nondestructive testing is developed in this study so that crack, corrosion, and delaminate in metallic and composite structures can be instantaneously detected without referencing to previously stored baseline data. This reference-free technique for damage detection is developed based on the Lamb wave theory and PZT polarization characteristics. Crack formation in a thin plate converts Lamb waves reflected and refracted from the crack to other modes. The appearance of this mode conversion is extracted by strategically placed PZT wafer transducers considering the poling directions of individual PZTs. Numerical simulations and experimental tests conducted in this study substantiate the effectiveness of the proposed reference-free technique for damage detection. Practical instrumentation issues such as variations in PZT size, bonding condition as well as alignment are addressed by developing a filtering technique. Because this reference-free technique does not rely on previously obtained baseline data for damage detection, it is expected that this approach minimize false alarms of damage due to changing operational and environmental variations experienced by in-service structures. This robustness of the proposed technique against undesirable variations in the system, such as temperature and external loading, makes it attractive for onboard monitoring. Further investigation is underway to extend the proposed concept to more complex structures.

The present invention will now be described in terms of embodiments utilizing dual piezoelectric transducers attached on a single surface. These embodiments of the present invention are organized as follows. First, the proposed reference-free diagnosis using Lamb wave propagation and dual PZTs is described. Then a description is provided of the numerical simulations that are executed to apply the NDT technique to damage detection.

Theoretical Development

Extracting Mode Converted Signals Due to Crack Damage Using Dual PZTs

Figure 107:
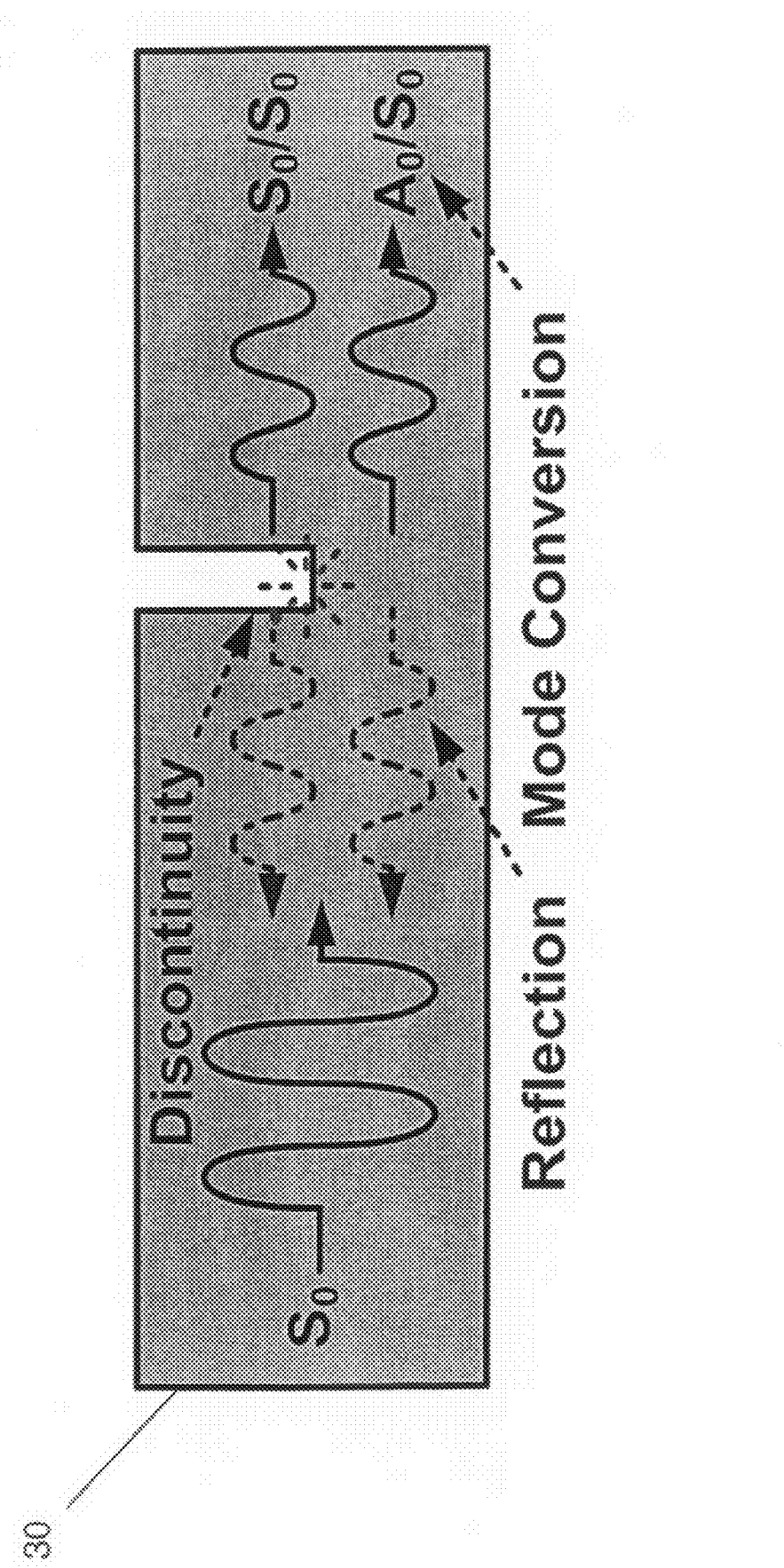
FIG. 107 illustrates a schematic diagram of mode conversion and reflection due to a discontinuity on a plate.

In this section, the basic idea of using dual PZTs is described to demonstrate how mode conversion due to crack formation can be detected without using any prior baseline data. First, the effect of a crack on Lamb wave modes is described. Lamb waves are a type of mechanical waves which propagate along a thin medium (Viktorov, (1967) Rayleigh and Lamb Waves, Plenum Press). When a thin plate is excited by a single tone-burst input, it is separated into several symmetrical ($S_0$, $S_1$ ...) and anti-symmetrical modes ($A_0$, $A_1$ ...) due to the multimodal aspect of Lamb waves (Victorov, 1967). The number of generated Lamb wave modes can be controlled by selecting the frequency of the input signal. In this section, it is assumed that a narrow-band tone burst is applied as an input signal, and the driving frequency is chosen such that only the fundamental symmetric ($S_0$) and anti-symmetric ($A_0$) modes are generated. If Lamb waves propagating along a thin plate encounter a discontinuity, some portion of the waves are reflected at the discontinuity point and others are transmitted through it. When a $S_0$ mode arrives at the notch as shown in FIG. 107, it is separated into $S_0$ and $A_0$ modes (denoted as $S_0/S_0$ and $A_0/S_0$, respectively). In a similar manner, an $A_0$ mode is also divided into $S_0$ and $A_0$ modes ($S_0/A_0$, and $AG/A_0$). This phenomenon is called mode conversion (Cho Y. (2000) Estimation of Ultrasonic Guided Wave Mode Conversion in a Plate with Thickness Variation", IEEE transactions on ultrasonics, ferroelectrics, and frequency control, Vol. 47, No. 3, pp. 591-603).

Figure 108:
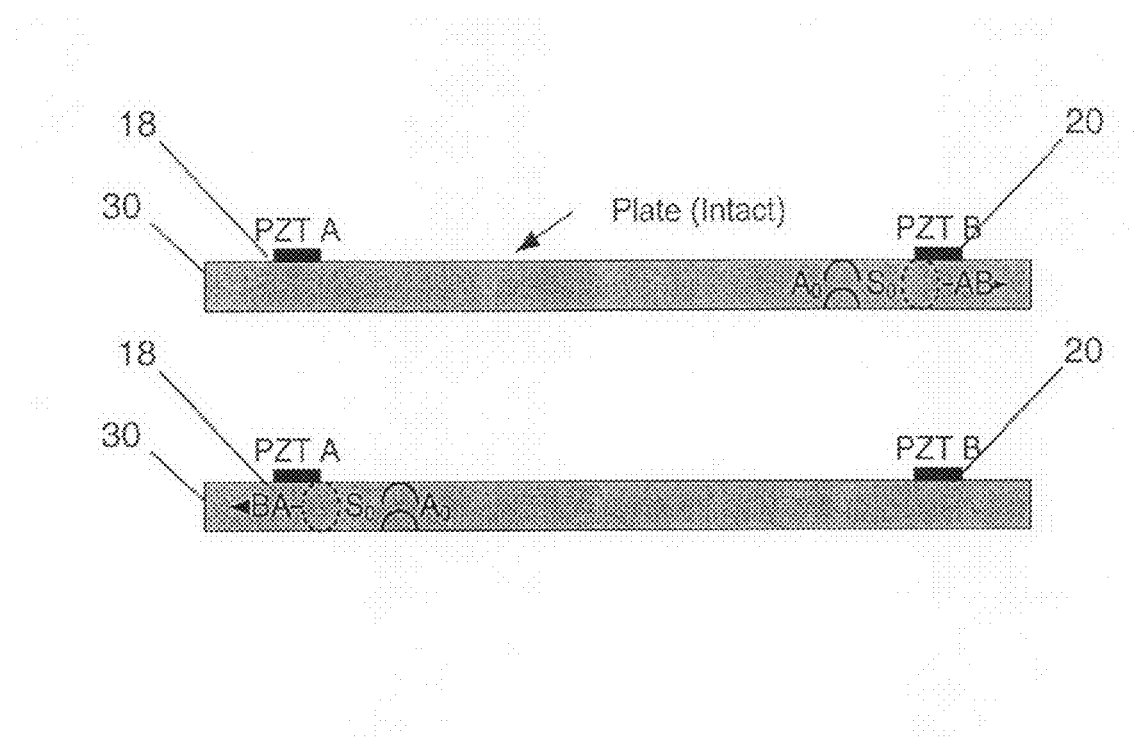
Figure 109:
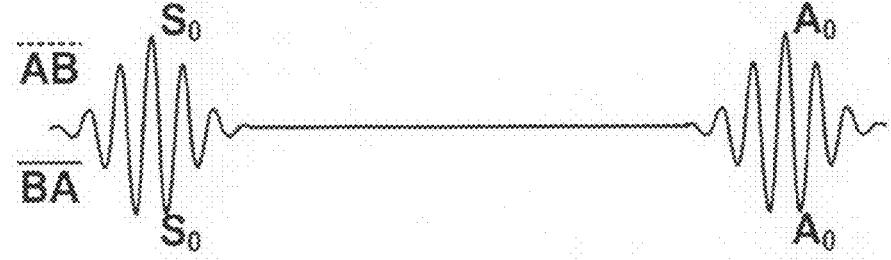
Figure 110:
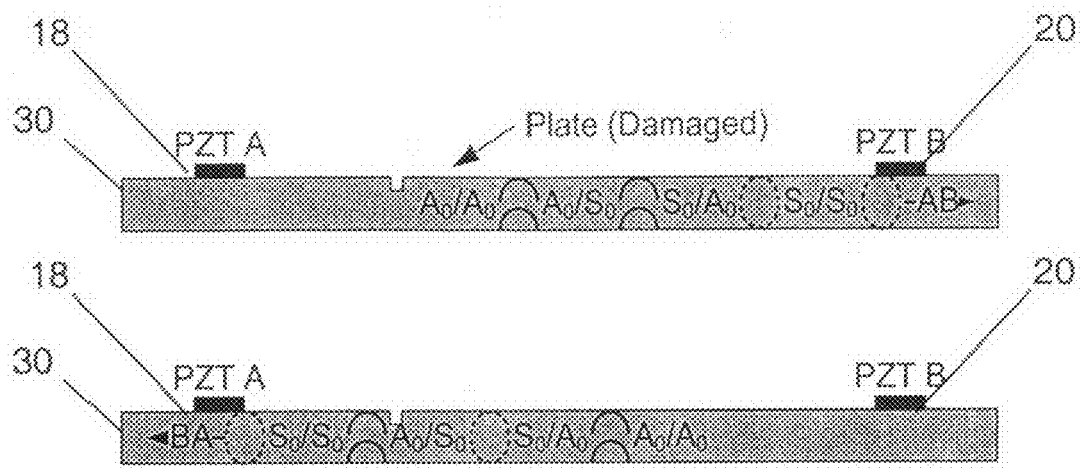
Figure 111:
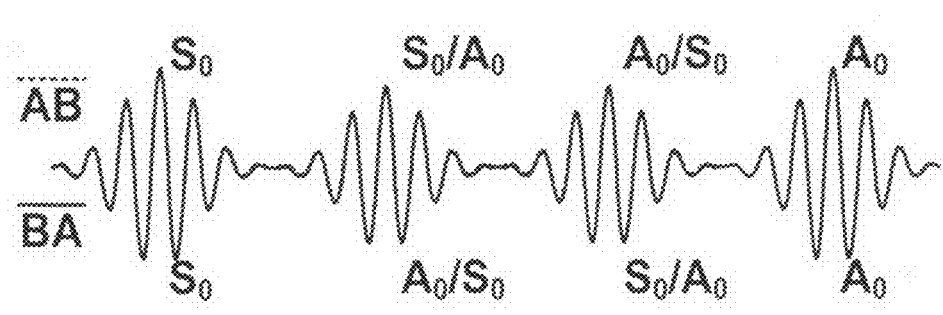

When the plate is in a pristine condition and two regular identical PZTs are instrumented as shown in FIG. 108, it can be shown that a signal AB becomes identical to a signal BA as illustrated in FIG. 109 (Park H. W., Kim S. B and Sohn H. (2007) Understanding a Time Reversal Process in Lamb Wave Propagations, Proceedings on Structural Control and Health Monitoring). Here, the signal AB denotes the response signal measured at PZT B when the excitation is applied at PZT A, and the signal BA is defined in a similar fashion. After crack damage is made between two transducers, additional modes are generated and added to signals AB and BA. As for the signal AB, the $S_0/A_0$ mode arrives at PMT B earlier than the $A_0/S_0$ mode when the notch is located closer to PZT A than PZT B (assuming that the $S_0$ mode travels faster than the $A_0$ mode). Conversely, the $S_0/A_0$ mode arrives at PZT A later than the $A_0/S_0$ mode in the case of the signal BA. Even though there is a crack between PZTs A and B, the signal AB is still identical to the signal BA [FIGS. 110 and 111]. This is because $S_0/A_0$ mode generated by PZT A is identical to $A_0/S_0$ mode generated by PZT B due to reciprocity in a linear system. In the same manner, $A_0/S_0$ generated by PZT A becomes identical to $S_0/A_0$ generated by PZT B.

Figure 112:
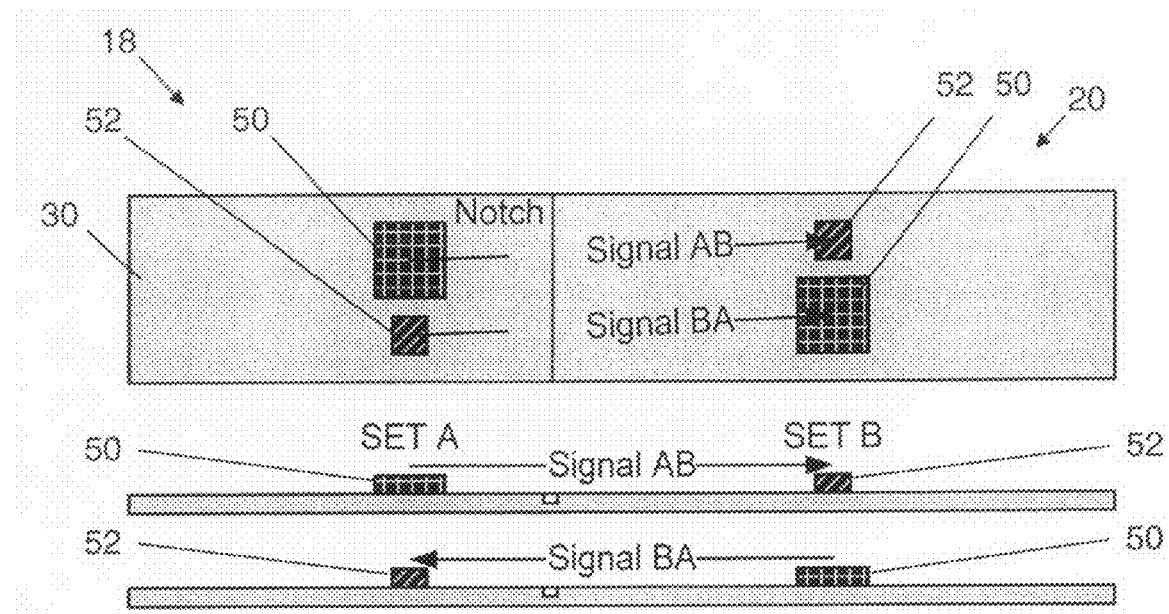
Figure 113:
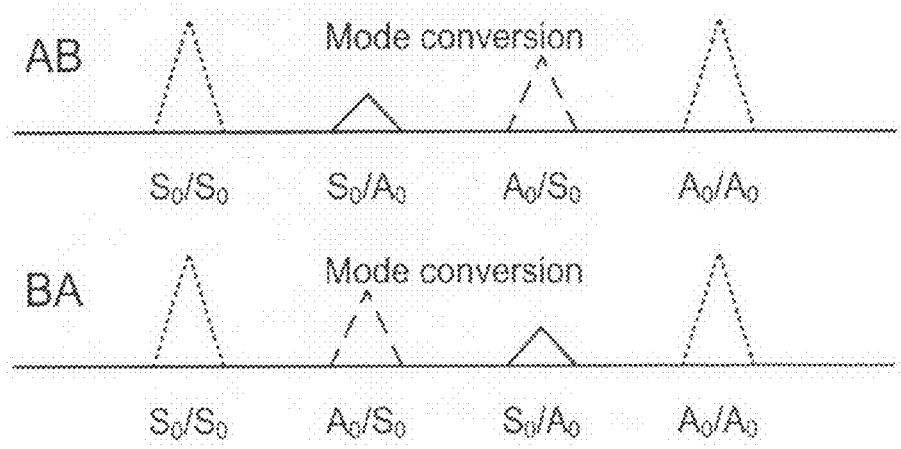
Figure 114:
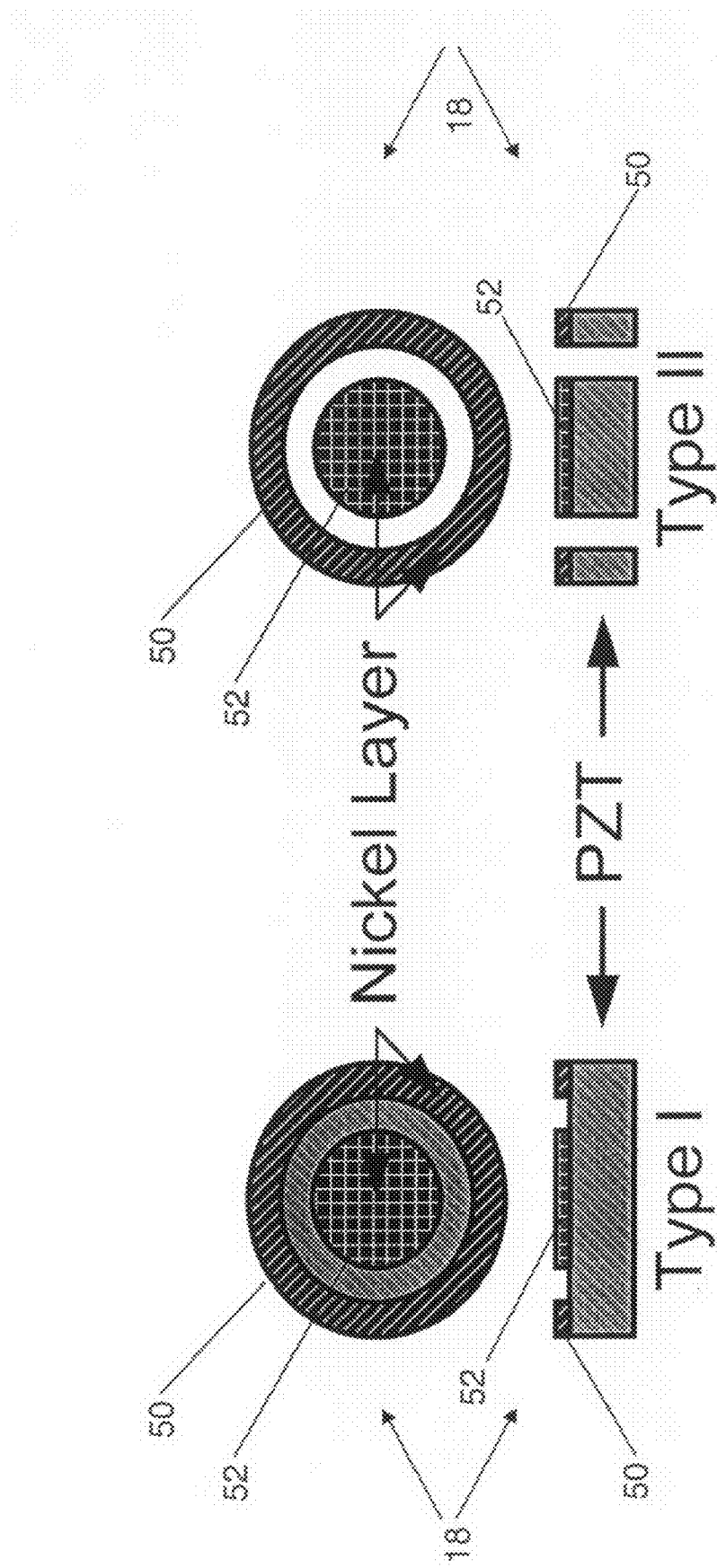
FIG. 114 illustrates a schematic diagram of dual PZTs which overcome the spatial limitation of test sets in FIG. 112: Type I is fabricated by etching a nickel layer on top of a circular PZT patch, and Type II is a combination of a ring type and a circular type of PZT patches.

The main concept of dual PZTs is that $S_0/A_0$ ($A_0/S_0$) mode in signal AB and $A_0/S_0$ ($S_0/A_0$) mode in signal BA can be distinguished by using different PZTs for excitation and measurement. For example, $S_0/A_0$ mode in signal AB and $A_0/S_0$ mode in signal BA are no longer identical when a large PZT wafer 50 is used for excitation and a small one 52 is used for sensing [FIG. 112]. Note that $S_0$ and $A_0$ modes are still identical in both cases while two mode converted signals show deviation [FIG. 113]. Finally, to overcome the spatial limitation of attaching two different PZTs at the same location, a novel approach of using dual PZTs is disclosed [FIG. 114]. In FIG. 114, two embodiments of dual PZTs are shown. Type I is fabricated by etching a nickel layer on top of a circular PZT patch, and Type II is a combination of a ring type 50 and a circular type 52 of PZT patches. In order to measure signals AB and BA, input voltage is exerted to both the outer 50 and inner 52 part of the PZT 18 while output voltage is measured only from the inner 52 part. Then, the additional modes generated by a notch can be extracted simply by subtracting the signal AB from the signal BA as shown in FIG. 113. Because this approach relies only on comparison of two signals obtained at the current state of the system rather than comparison with previously recorded reference data, it is expected that this approach reduces false alarms of defect due to changing operational and environmental variations of the system. For instance, it can be readily shown that temperature change of the system does not affect this approach.

Numerical Simulation

Figure 115:
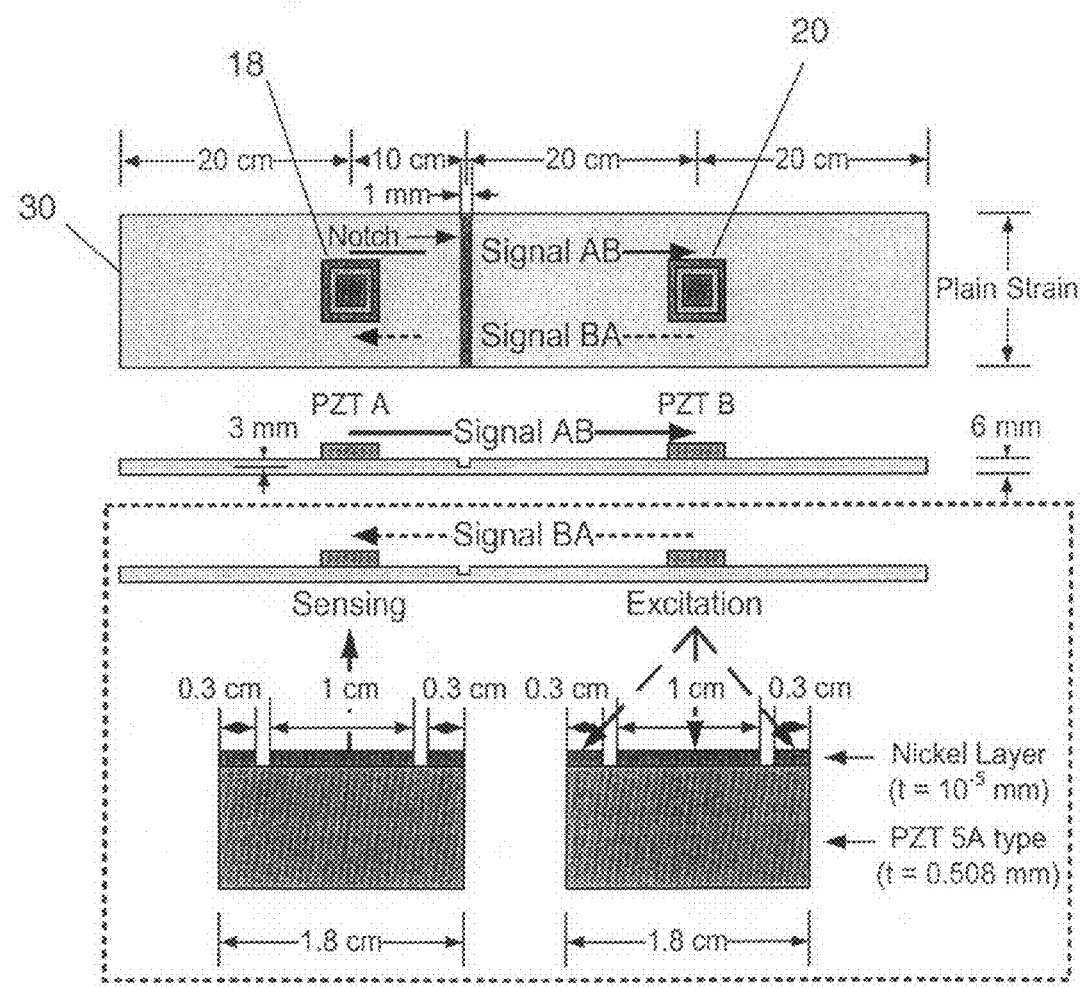
FIG. 115 illustrates dimensions of an aluminum plate and dual PZTs (Type I) used in numerical simulation according to the present invention.

The idea of using dual PZTs for crack detection was validated by numerical simulation. Using COMSOL 3.3a Multiphysics software (www.comsol.com), Lamb wave propagation in a two dimensional aluminum beam was simulated using the combination of plain strain, piezo plain strain, and electrostatics modules in the software. The length of the beam was 70 cm, and its thickness was 6 mm. Two identical dual PZTs (Type I) were attached to the beam model as shown in FIG. 115. The parameter values used in the numerical simulation are listed in Table 12. A narrowband tone-burst signal at 150 kHz frequency was used as an input signal. In the simulation, Rayleigh damping coefficients were set to 104 for a mass damping coefficient and 0 for a stiffness damping coefficient, respectively. The simulation results were obtained from a time dependent solver, and a time step was set to 0.25 μs, which is equivalent to 4 M samples/sec. To control the error in each integration step, relative tolerance and absolute tolerance for the solution were chosen to be $10^{-4}$ and $10^-$, respectively. The maximum backward differentiation formula (BDF) order for setting the degree of the interpolating polynomials in the time-stepping method was set to order 2. Finally, the model was meshed using a mapped mesh option, and the size of each mesh was limited to 1 mm×1 mm. (COMSOL AB. (2005) COMSOL Multiphysics User's Guide, Version 3.2.)

TABLE 12

| Parameters used in numerical simulation | |
|---|---|
| Exciting frequency | 150 kHz |
| α (Mass damping coeff.) | $10^{-4}$ |
| β (Stiffness damping coeff.) | 0 |
| Sampling rate | 4 Ms/s |
| Relative tolerance | $10^{-4}$ |
| Absolute tolerance | $10^{-10}$ |
| Maximum BDF order | 2 |
| Mesh size (mapped mesh) | 1 mm × 1 mm max. |

Figure 116:
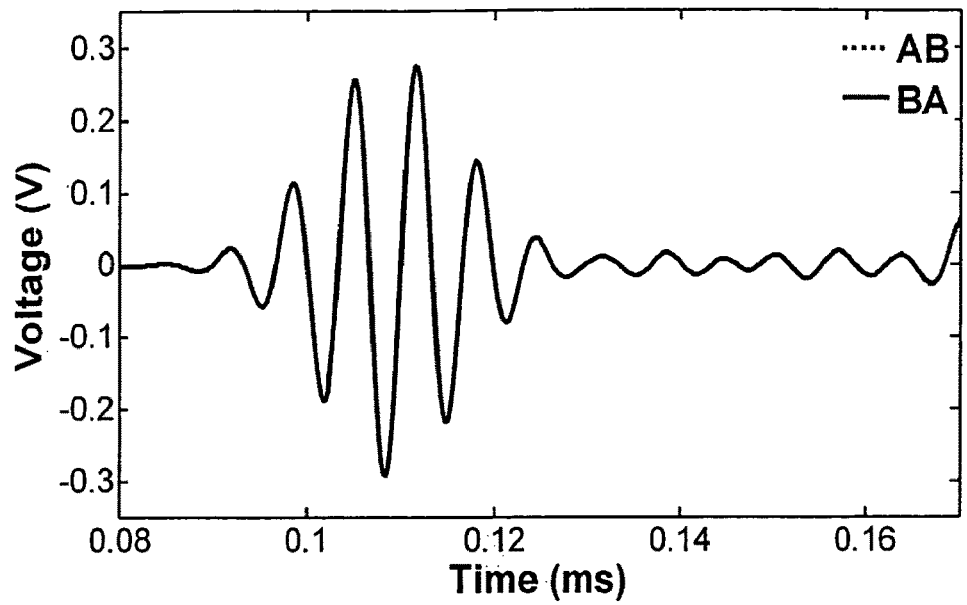
Figure 117:
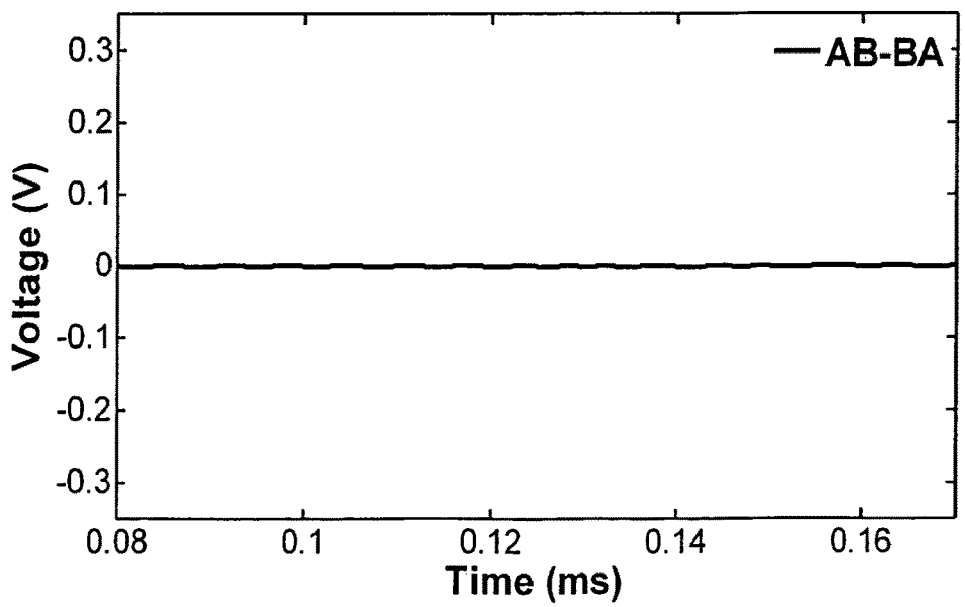
Figure 118:
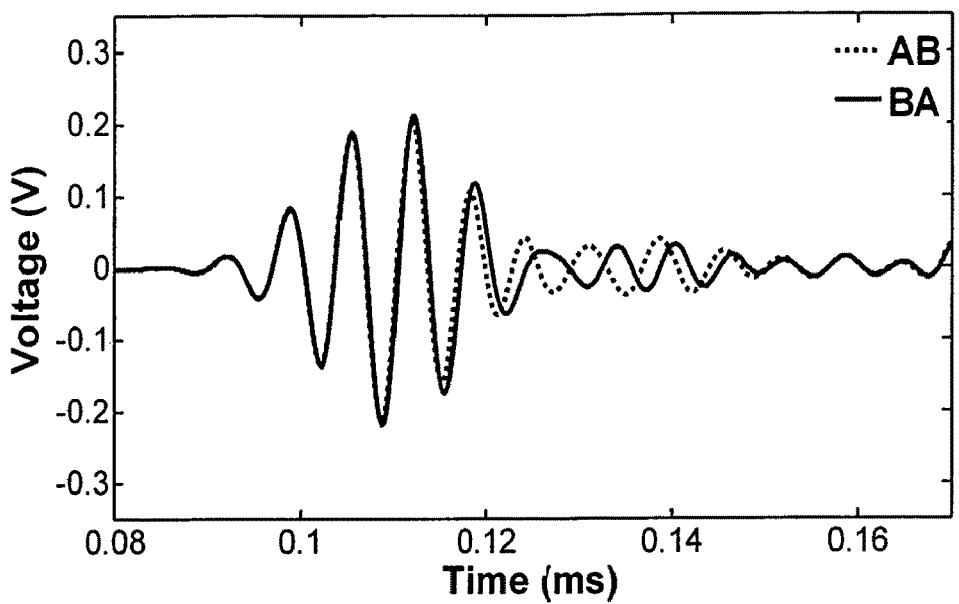
Figure 119:
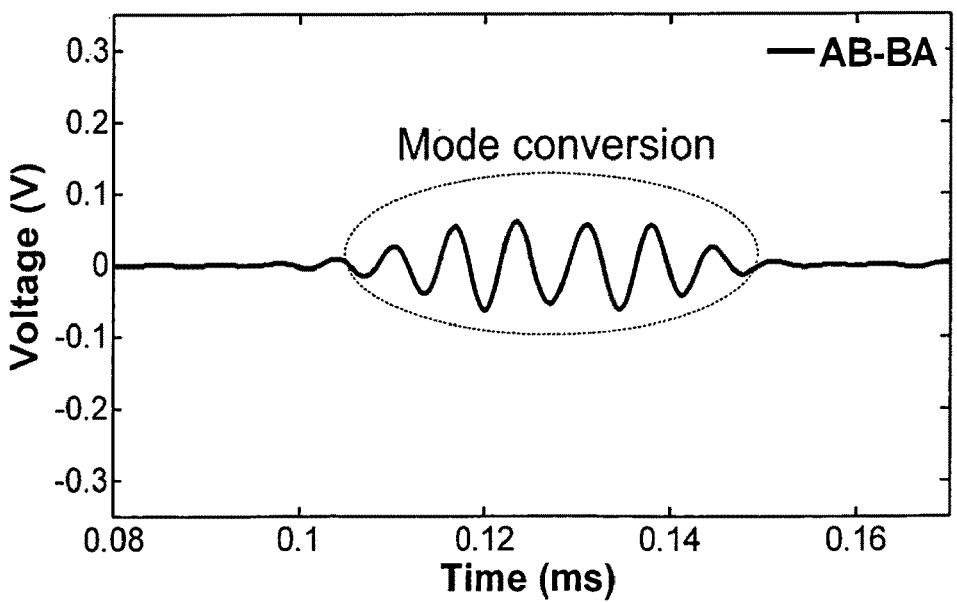

FIGS. 116 and 117 illustrate that signals AB and BA were almost identical and this well corresponds to the theoretical expectation. Once a notch of 3 mm depth and 1 mm width was introduced 100 mm away from PZT A toward PZT B, the signal AB became different from the signal BA as a result of the mode conversion induced by the crack [FIG. 118]. The mode conversion due to cracking was extracted simply by subtracting the signal BA from the signal AB [FIG. 119]. This numerical example clearly demonstrates that cracks can be identified instantly without relying on previously stored data.

Figure 120:
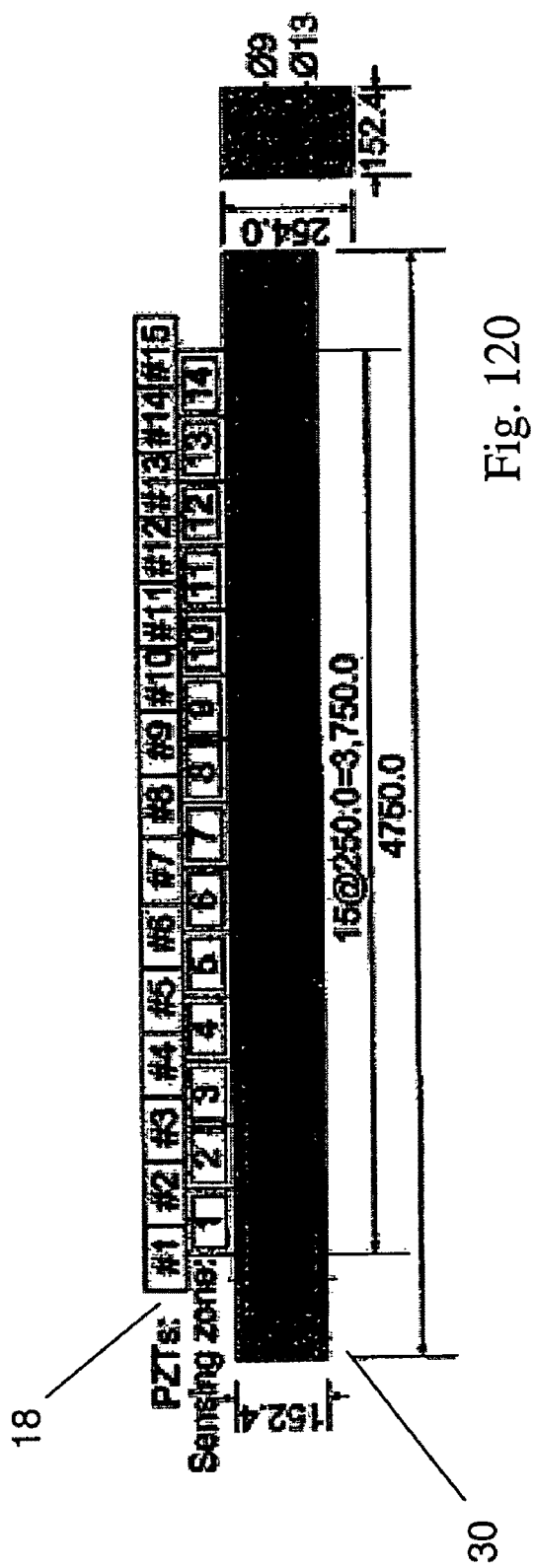
FIG. 120 illustrates one embodiment of the present invention in the form of piezoelectric devices along a structure.

FIG. 120 illustrates one embodiment of the present invention in which many piezoelectric devices 18 are arranged on a structure 30. Although the present invention was generally described in terms of the use of two or four piezoelectric devices, many piezoelectric devices may be used together according to the present invention. FIG. 120 illustrates the present invention using fifteen (15) piezoelectric devices 18 installed along structure 30. The structure 30 illustrated in FIG. 30 may be, for example, aluminum skin of an aircraft, a composite panel, a reinforced concrete beam, or other structures. FIG. 120 also illustrates the detection region or sensing zones around each piezoelectric device 18. In this illustration, all units are in millimeters, although other sizes, scales, and arrangements are also possible.

Figure 121:
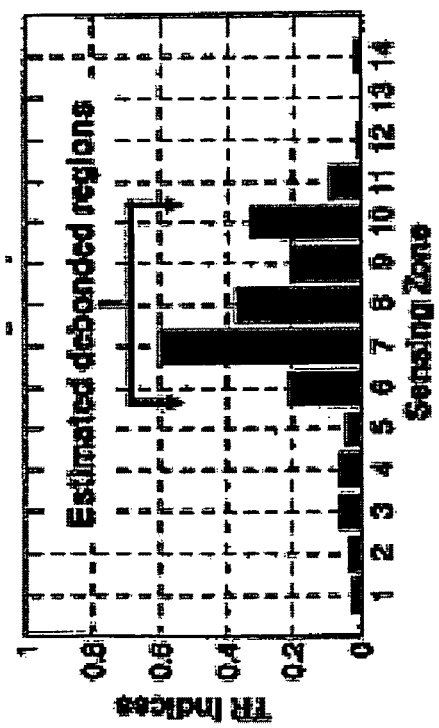
FIG. 121 illustrates test results related to the embodiment illustrated in FIG. 120.

FIG. 121 illustrates test results that may be obtained with the embodiment illustrated in FIG. 120. In particular, the present invention may use statistical pattern recognition techniques, such as sequential outlier or clustering analysis. These techniques may be used to fully automate the damage diagnosis process without requiring user interface or user-specified decision boundaries. In this example, the structure 30 was a reinforced concrete beam and was subjected to monotonic and fatigue loading using a hydraulic actuator. The baseline-free methodology of the present invention detected debonding between the carbon fiber reinforced polymer and the reinforced concrete beam. A damage index called a time reversal (TR) index was computed at a damage state on the beam 30. Once the TR index values are computed, a clustering analysis is based only on comparison of "present" TR index values and the damage classification does not require any prior TR index values or predetermined decision boundaries.

Summary

The present invention describes new methods, systems, and apparatuses of nondestructive testing is described in this invention such that crack, corrosion, and delaminate in metallic and composite structures can be instantaneously detected without referencing previously stored baseline data. This reference-free technique for damage detection is developed based on the Lamb wave theory and the utilization of dual PZTs. Crack formation in a thin plate converts Lamb waves reflected and refracted from the crack to other modes. The appearance of this mode conversion is extracted by dual PZTs from instantaneously measured Lamb wave signals. Numerical simulations substantiate the effectiveness of the disclosed reference-free technique for damage detection. Because this reference-free technique does not rely on previously obtained baseline data for damage detection, it is expected that this approach will minimize false alarms of damage due to changing operational and environmental variations experienced by in-service structures. This robustness of the proposed technique against undesirable variations in the system, such as temperature and external loading, makes it attractive for onboard monitoring.

Although the present invention has generally been described in terms of specific embodiments, the present invention is applicable to other embodiments, including other methods, apparatuses, systems, and technologies. For example, although the present invention describes embodiments that can operate without comparison to baseline data and without the use of human operators to review the data and determine the results of the tests, advantages of the present invention can still be realized if the present invention is used in conjunction with comparisons to baseline data and/or with human operators reviewing the data and determining results. Those and other variations and modifications of the present invention are possible and contemplated, and it is intended that the foregoing specification and the following claims cover such modifications and variations.

The invention claimed is:

1. A method for autonomous baseline-free diagnosis of a structure, comprising:
    generating a first acoustic signal from a first location on the structure, wherein the first acoustic signal has a main frequency and a bandwidth, and wherein the bandwidth is not more than ten percent of the main frequency;
    receiving the first acoustic signal at a second location on the structure, wherein the first location and the second location are different;

generating a second acoustic signal from the second location on the structure, wherein the second acoustic signal has a main frequency and a bandwidth, and wherein the bandwidth is not more than ten percent of the main frequency;

receiving the second acoustic signal at the first location on the structure;

measuring the $S_0$ modes and $A_0$ modes of the first acoustic signal received at the second location;

measuring the $S_0$ modes and $A_0$ modes of the second acoustic signal received at the first location; and identifying differences in the $S_0$ modes and $A_0$ modes of the first and second acoustic signals received at the second and first locations, respectively.

2. The method of claim 1, wherein the structure has a first surface and a second surface, wherein the first and second surfaces are on opposite sides of the structure, and wherein:

receiving the first acoustic signal at the second location includes measuring tine fast acoustic signal on both the first and second surfaces of the structure at the second location; and receiving the second acoustic signal at the first location includes measuring the second acoustic signal on both the first and second surfaces of the structure at the first location.

3. The method of claim 1, wherein identifying differences in the $S_0$ modes and $A_0$ modes of the first and second acoustic signals received at the second and first locations, respectively, includes calculating a point by point product value between the first and second acoustic signals received at the second and first locations, respectively.

4. The method of claim 3, wherein a defect in the structure is identified if the point by point product value includes at least one negative value.

5. The method of claim 3, wherein a defect in the structure is identified if the point by point product value includes at least one negative value having a duration exceeding a predetermined duration.

6. The method of claim 3, wherein a defect in the structure is identified if the point by point product value includes at least one negative value baying a duration exceeding 0.98 μs.

7. The method of claim 3, further comprising filtering the point by point product value to remove negative values having a duration less than a predetermined duration.

8. The method of claim 3, further comprising filtering the point by point product value to remove negative values having a duration less than 0.98 μs.

9. The method of claim 1, wherein identifying differences in the $S_0$ modes and $A_0$ modes includes measuring arrival time for $A_0/S_0$ and $S_0/A_0$ nodes in the first and second acoustic signals received at the second and first locations, respectively.

10. The method of claim 1, wherein identifying differences in the $S_0$ modes and $A_0$ modes of the first and second acoustic signals includes measuring relative phase between at least one of $S_0$ modes and $A_0$ modes in both the first and second acoustic signals received at the second and first locations, respectively.

11. The method of claim 10, wherein identifying differences in the $S_0$ modes and $A_0$ modes of the first and second acoustic signals includes:

measuring relative phase between $S_0$ modes in the first and second acoustic signals received at the second and first locations, respectively; and measuring relative phase between $A_0$ modes in the first and second acoustic signals received at the second and first locations, respectively.

12. The method of claim 10, wherein measuring relative phase between $S_0$ modes and $A_0$ modes in the first and second acoustic signals includes subtracting the first acoustic signal received at the second location from the second acoustic signal received at the first location.

13. The method of claim 1, wherein identifying differences in the $S_0$ modes and $A_0$ modes includes:

measuring arrival time for $A_0/S_0$ and $S_0/A_0$ modes in the first and second acoustic signals received at the second and first locations, respectively; and measuring relative phase between at least one of $S_0$ modes and $A_0$ modes in both the first and second acoustic signals received at the second and first locations, respectively.

14. The method of claim 1, wherein:

generating a first acoustic signal includes generating a first acoustic signal with a first piezoelectric device at the first location on the structure;

receiving the first acoustic signal includes receiving the first acoustic signal with a second piezoelectric device at the second location on the structure;

generating a second acoustic signal includes generating a second acoustic signal with the second piezoelectric device at the second location on the structure; and receiving the second acoustic signal includes receiving the second acoustic signal with the first piezoelectric device at the first location on the structure.

15. The method of claim 1, wherein;

generating a first acoustic signal includes generating a first acoustic signal with a first piezoelectric device at the first location on the structure;

receiving the first acoustic signal includes receiving the first acoustic signal with a second piezoelectric device at the second location on the structure;

generating a second acoustic signal includes generating a second acoustic signal with a third piezoelectric device at the second location on the structure; and receiving the second acoustic signal includes receiving the second acoustic signal with a fourth piezoelectric device at the first location on the structure.

16. A system for autonomous baseline-free diagnosis of a structure, wherein the structure has a first surface and a second surface, wherein the first and second surfaces are on opposite sides of the structure, comprising:

a first piezoelectric device at a first location on the first surface of the structure, a second piezoelectric device at a second location on the first surface of the structure;

a third piezoelectric device at a second location on the second surface of the structure, said second location on the second surface the structure corresponding to the second location on the first surface of the structure;

a fourth piezoelectric device at a first location on the second surface of the structure, said first location on the second surface the structure corresponding to the first location on the first surface of the structure;

a signal generator connected to at least two of the first, second, third, and fourth piezoelectric devices;

a processor connected to the signal generator and connected to the first, second, third, and fourth piezoelectric; devices; and computer readable memory connected to the processor, wherein the memory includes computer-readable instructions which, when executed by the processor, cause:

generating a first acoustic signal from the first location on each side of the structure, wherein the first acoustic signal has a main frequency and a bandwidth, and wherein the bandwidth is not more than ten percent of the main frequency;

receiving the first acoustic signal at the second location on each side of the structure, wherein the first location and the second location are different;

generating a second acoustic signal from the second location on each side of the structure, wherein the second acoustic signal has a main frequency and a bandwidth, and wherein the bandwidth is not more than ten percent of the main frequency;

receiving the second acoustic signal at the first location on each side of the structure;

measuring the $S_0$ modes and $A_0$ modes of the first acoustic signal received at the second location on each side of the structure;

measuring the $S_0$ modes and $A_0$ modes of the second acoustic signal received at the first location on each side of the structure; and identifying differences in the $S_0$ modes and $A_0$ modes of the first and second acoustic signals received at each second and first location, respectively.

17. The system of claim 16, wherein:

at least one of the first and fourth piezoelectric devices includes an excitation piezoelectric transducer for generating the first acoustic signal and a sensing piezoelectric transducer for receiving the second acoustic signal; and at least one of the second and third piezoelectric devices includes a sensing piezoelectric transducer for receiving the first acoustic signal and an excitation piezoelectric transducer for generating the second acoustic signal.

18. The system of claim 17, wherein:

the excitation piezoelectric transducer in the at least one of the first and fourth piezoelectric devices is larger than the sensing piezoelectric transducer in the at least one of the first and fourth piezoelectric devices; and the excitation piezoelectric transducer in the at least one of the second and third piezoelectric devices is larger than the sensing piezoelectric transducer in the at least one of the second and third piezoelectric devices.

19. The system of claim 18, wherein:

the excitation piezoelectric transducer in the at least one of the first and fourth piezoelectric devices is ring-shaped and the sensing piezoelectric transducer in the at least one of the first and fourth piezoelectric devices is circular-shaped, and wherein the excitation piezoelectric transducer in the at least one of the first and fourth piezoelectric devices and the sensing piezoelectric transducer in the at least one of the first and fourth piezoelectric devices are concentric; and the excitation piezoelectric transducer in the at least one of the second and third piezoelectric devices is ring-shaped and the sensing piezoelectric transducer in the at least one of the second and third piezoelectric devices is circular-shaped, and wherein the excitation piezoelectric transducer in the at least one of the second and third piezoelectric devices and the sensing piezoelectric transducer in the at least one of the second and third piezoelectric devices are concentric.

20. A method for autonomous baseline-free diagnosis of a structure, comprising:

generating a first acoustic signal from a first location on the structure, wherein the first acoustic signal has a main frequency and a bandwidth, and wherein the bandwidth is not more than ten percent of the main frequency;

receiving the first acoustic signal at a second location on the structure, wherein the first location and the second location are different;

reversing, in the time domain, the first acoustic signal received at the second location;

truncating the first acoustic signal received at the second location;

generating a second acoustic signal from the second location on the structure, wherein the second acoustic signal is the truncated, time domain reversed first acoustic signal received at the second location;

receiving the second acoustic signal at the first location on the structure; and determining a diagnosis of the structure based on the second acoustic signal received at the first location;

wherein truncating the first acoustic signal occurs before reversing, in the time domain, the first acoustic signal.

21. The method of claim 20, wherein generating the first acoustic signal includes generating only a first symmetric mode ($S_0$) and only a first anti-symmetric mode ($A_0$) from the first location on the structure.

22. The method of claim 20, wherein reversing, in the time domain, the first acoustic signal received at the second location, includes changing the first acoustic signal received at the second location on the structure into the complex conjugate of the first acoustic signal received at the second location on the structure.

23. The method of claim 20, wherein the first acoustic signal is symmetric in the time domain.

24. The method of claim 20, further comprising, after receiving the second acoustic signal at the first location on the structure:

band limited filtering of the second acoustic signal received at the first location;

scaling the second acoustic signal received at the first location; and denoising the second acoustic signal received at the first location using wavelet analysis.

25. The method of claim 24, wherein denoising the second acoustic signal received at the first location using wavelet analysis includes wavelet analysis using a basis function that is the same as the first acoustic signal.

26. The method of claim 25, wherein determining a diagnosis of the structure based on the second acoustic signal received at the first location includes:

determining a plurality of damage indexes from a plurality of paths through the structure; and testing a damage index along a path through the structure against a damage index along at least one different path in the structure.

27. The method of claim 26, wherein determining a diagnosis of the structure based on the second acoustic signal received at the first location includes:

testing a second damage index along a second path through the structure against a damage index along at least one different path in the structure.

28. The method of claim 25, wherein determining a diagnosis of the structure based on the second acoustic signal received at the first location includes:

determining a plurality of damage indexes from a plurality of paths through the structure; and testing each of the plurality of damage indexes along the plurality of paths through the structure against each other damage index in the structure.

29. A system for autonomous baseline-free diagnosis of a structure, comprising:
- a first piezoelectric device at a first location on the structure;
- a second piezoelectric device at a second location on the structure;
- a signal generator connected to the first piezoelectric device;
- a processor connected to the signal generator and connected to the first and second (20) piezoelectric devices; and
- computer readable memory connected to the processor, wherein the memory includes computer-readable instructions which, when executed by the processor, cause
  - generating a first acoustic signal from a first location on the structure, wherein the first acoustic signal has a main frequency and a bandwidth, and wherein the bandwidth is not more than ten percent of the main frequency;
  - receiving the first acoustic signal at a second location on the structure, wherein the first location and the second location are different;
  - reversing, in the time domain, the first acoustic signal received at the second location;
  - truncating the first acoustic signal received at the second location;
  - generating a second acoustic signal from the second location on the structure, wherein the second acoustic signal is the truncated, time domain reversed first acoustic signal received at the second location;
  - receiving the second acoustic signal at the first location on the structure (30); and
  - determining a diagnosis of the structure (30) based on the second acoustic signal received at the first location;
  - wherein truncating the first acoustic signal occurs before reversing, in the time domain, the first acoustic signal.

30. The system of claim 29, wherein:
the first piezoelectric device includes a first excitation piezoelectric transducer for generating the first acoustic signal and a first sensing piezoelectric transducer for receiving the second acoustic signal; and
a second piezoelectric device includes a second sensing piezoelectric transducer for receiving the first acoustic signal and a second excitation piezoelectric transducer for generating the second acoustic signal.

31. The system of claim 30, wherein:
the first excitation piezoelectric transducer is larger than the first sensing piezoelectric transducer; and
the second excitation piezoelectric transducer is larger then the second sensing piezoelectric transducer.

32. The system of claim 31, wherein:
the first excitation piezoelectric transducer is ring-shaped and the first sensing piezoelectric transducer is circular-shaped, and wherein the first excitation piezoelectric transducer and the first sensing piezoelectric transducer are concentric; and
the second excitation piezoelectric transducer is ring-shaped and the second sensing piezoelectric transducer is circular-shaped, and wherein the second excitation piezoelectric transducer and the second sensing piezoelectric transducer are concentric.

* * * * *